United States Patent
Oost et al.

(10) Patent No.: US 8,791,272 B2
(45) Date of Patent: Jul. 29, 2014

(54) PYRAZOLE COMPOUNDS AS CRTH2 ANTAGONISTS

(75) Inventors: Thorsten Oost, Biberach (DE); Ralf Anderskewitz, Laupheim (DE); Dieter Wolfgang Hamprecht, Pozzolengo (IT); Christoph Hoenke, Ingelheim (DE); Domnic Martyres, Biberach (DE); Wolfgang Rist, Mittelbiberach (DE); Peter Seither, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 171 days.

(21) Appl. No.: 13/012,244

(22) Filed: Jan. 24, 2011

(65) Prior Publication Data
US 2012/0028938 A1 Feb. 2, 2012

(51) Int. Cl.
*C07D 231/12* (2006.01)
*A61K 31/415* (2006.01)
*C07D 405/12* (2006.01)
*C07D 401/06* (2006.01)

(52) U.S. Cl.
CPC ............ *C07D 231/12* (2013.01); *C07D 405/12* (2013.01); *C07D 401/06* (2013.01)
USPC ......................................... 548/375.1; 514/406

(58) Field of Classification Search
CPC .................................................... C07D 231/12
USPC ........................................ 548/375.1; 514/406
See application file for complete search history.

(56) References Cited

U.S. PATENT DOCUMENTS

2006/0106061 A1* 5/2006 Ghosh et al. .................. 514/312
2010/0016368 A1   1/2010 Chen et al.

FOREIGN PATENT DOCUMENTS

WO   0138325 A1   5/2001
WO   2011092140 A1   8/2011

OTHER PUBLICATIONS

STN results (2 pages) JP 48028914 (1973) and US 3704241 (1972).*
International Search Report for PCT/EP2011/050910 mailed Mar. 21, 2011.

* cited by examiner

*Primary Examiner* — Yong Chu
*Assistant Examiner* — Sonya Wright
(74) *Attorney, Agent, or Firm* — Michael P. Morris; Timothy X. Witkowski

(57) ABSTRACT

The present invention relates to pyrazole compounds of formula (I) and pharmaceutically acceptable salts thereof having CRTH2-activity,

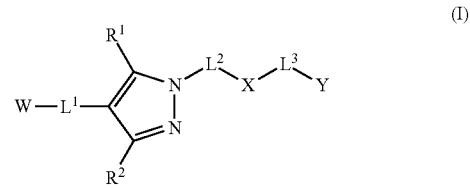

wherein W, $L^1$, $L^2$, X, $L^3$, Y, $R^1$ and $R^2$ are as defined in the specification and claims, to their use as medicaments and to pharmaceutical formulations, containing said compounds or containing a combination of said compounds with one or more active substances.

51 Claims, No Drawings

PYRAZOLE COMPOUNDS AS CRTH2 ANTAGONISTS

The present invention relates to pyrazole compounds of formula (I) and pharmaceutically acceptable salts thereof having CRTH2 antagonistic activity,

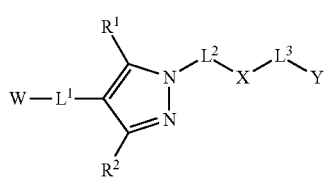

wherein W, $L^1$, $L^2$, $L^3$, Y, $R^1$ and $R^2$ have one of the meanings given in the specification, to the use of said compounds as medicaments; to pharmaceutical formulations, containing said compounds, and to pharmaceutical formulations, containing said compounds in combination with one or more active substances.

BACKGROUND OF THE INVENTION

Prostaglandin D2 (PGD2) is an eicosanoid generated by the metabolism of arachidonic acids upon stimulation of inflammatory cells with allergens, inflammatory stimuli or by tissue damage. PGD2 is primarily released by mast cells with Th2 cells, dendritic cells, and macrophages being secondary sources. PGD2 is the major arachidonic acid metabolite produced by mast cells upon allergen challenge (Lewis et al., J. Immunol. 1982, 129:1627-1631) and has been detected in high concentrations in the airways of asthmatic patients (Murray et al, N Engl J Med, 1986, 315:800-804; Liu et al., Am Rev Respir Dis, 1990, 142 126-132; Zehr et al., Chest, 1989, 95:1059-63; Wenzel et al., J Allergy Clin Immunol, 1991, 87540-548). PGD2 production is also increased in patients with systemic mastocytosis (Roberts N. Engl. J. Med. 1980, 303, 1400-1404; Butterfield et al., Int Arch Allergy Immunol, 2008, 147:338-343) allergic rhinitis (Naclerio et al., Am Rev Respir Dis, 1983, 128:597-602; Brown et al., Arch Otolaryngol Head Neck Surg, 1987, 113:179-183; Lebel et al., J Allergy Clin Immunol, 1988, 82:869-877), urticaria (Heavy et al., J Allergy Clin Immunol, 1986, 78:458-461), chronic rhinosinusitis (Yoshimura et al., Allergol Int, 2008, 57:429-436), chronic obstructive pulmonary disease (Csanky et al., Electrophoresis, 2009, 30:1228-1234) and during anaphylaxis (Ono et al., Clin Exp Allergy, 2009, 39:72-80).

Instillation of PGD2 into airways can provoke features of asthmatic response including bronchoconstriction (Hardy et al., 1984, N Engl J. Med 311:209-213; Sampson et al 1997, Thorax 52: 513-518) and eosinophil accumulation (Emery et al., 1989, J. Applied Physiol 67: 959-962). The potential of PGD2 to trigger inflammatory responses has been confirmed by the overexpression of human PGD2 synthase in mice resulting in elevated eosinophil lung inflammation and Th2 cytokine production in response to allergen (Fujitani et al, 2002 J. Immunol. 168:443-449).

PGD2 is an agonist of two 7-transmembrane type G protein-coupled receptors, the PGD2 receptor DP1 (Boie et al., J Biol Chem, 1995, 270:18910-6) and the recently identified CRTH2 (chemoattractant receptor-homologous molecule expressed on Th2 cells) receptor (also referred to as DP2 receptor) (Nagata et al., J. Immunol., 1999, 162:1278-86).

CRTH2 is expressed on Th2 cells, eosinophils, basophils and mast cells (Nagata et al., FEBS Lett, 1999, 459: 195-199; Nagata et al., J Immunol, 1999, 162: 1278-1286; Cosmi et al., Eur J Immunol, 2000, 30:2972-2979; Boehme et al., Int Immunol, 2009, 21: 621-32). Using selective CRTH2 agonists like 13,14 dihydro-15-keto-PGD2 (DK-PGD2) and 15R-methyl-PGD2, it has been shown that CRTH2 activation initiates cellular processes that lead to the recruitment and activation of inflammatory cells (Spik et al., J. Immunol., 2005; 174:3703-8; Shiraishi, J. Pharmacol. Exp. Ther., 2005, 312:954-60; Monneret et al., J. Pharmacol. Exp. Ther., 2003, 304:349-355). Using CRTH2 selective antagonists it has been shown that inflammatory responses and pathophysiological changes in animal models of diseases like asthma, allergic rhinitis, atopic dermatitis and COPD can be diminished (Uller et al., Respir Res. 2007, 8:16; Lukacs et al., Am J Physiol Lung Cell Mol Physiol. 2008, 295:L767-79; Stearns, Bioorg. Med Chem Lett. 2009, 19:4647-51; Nomiya, J Immunol, 2008, 180:5680-5688; Boehme et al., Int Immunol, 2009, 21:1-17; Boehme et al., Int Immunol, 2009, 21:81-93; Takeshita et al., Int Immunol, 2004, 16:947-59; Stebbins et al., J Pharmacol Exp Ther. 2009). Moreover, genetic deletion of CRTH2 in mice diminished inflammatory responses in animal models of allergy (Shiraishi et al., J. Immunol. 2008; 180:541-549; Oiwa, Clin Exp Allergy, 2008, 38:1357-66; Satoh et al., J Immunol, 2006, 177:2621-9). In contrast, the selective DP1 agonist BW245C does not promote inflammatory responses, like migration or activation of Th2 lymphocytes, basophils or eosinophils (Yoshimura-Uchiyama et al., Clin Exp Allergy, 2004, 34:1283-90; Xue et al., Immunol, 2005, 175:6531-6; Gervais et al., J Allergy Clin Immunol, 2001, 108:982-8). Therefore, agents that antagonize the effects of PGD2 at the CRTH2 receptor should be useful for the treatment of respiratory or gastrointestinal complaints, as well as inflammatory diseases of the joints and allergic diseases of the nasopharynx, eyes and skin.

WO 2004/096777 teaches pyrimidine derivatives of formula (a), and salts thereof,

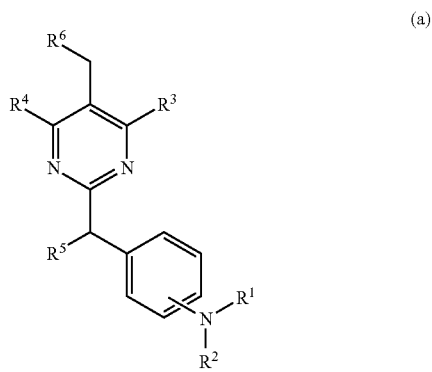

wherein $R^6$ is carboxy, carboxamide, nitrile or tetrazolyl, said derivatives having CRTH2 antagonistic activity and can be used for the prophylaxis and treatment of diseases associated with CRTH2 activity.

WO 2009/042138 claims alkylthio substituted pyrimidine compounds of formula (b),

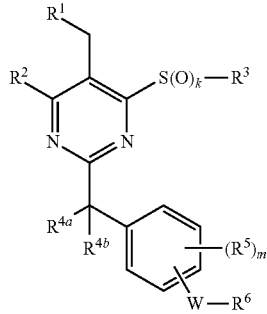

said compounds having CRTH2 antagonistic activity.

WO 2009/042139 claims 2-S-benzyl pyrimidine compounds of formula (c),

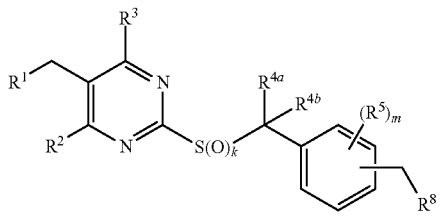

said compounds having CRTH2 antagonistic activity.

EP 0 480 659 claims compounds of general formula (d),

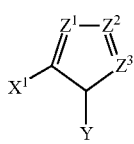

wherein $Z^2$ inter alia may be carboxyl-$C_1$-$C_{10}$-alkyl-C= and Y may be substituted benzyl, said compounds being useful for the treatment of hyperuricemia.

WO 2005/040128 claims compounds of general formula (e),

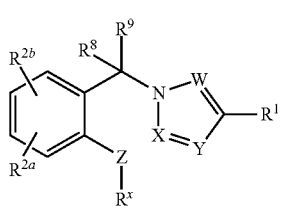

said compounds being useful for the treatment of conditions such as pain, or an inflammatory, immunological, bone, neurodegenerative or renal disorder.

WO 01/38325 claims compounds of general formula (f),

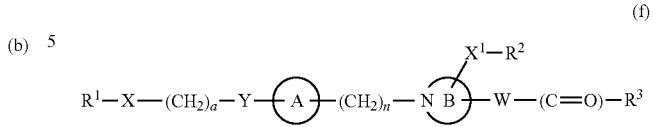

wherein A is an aromatic ring and B is a nitrogen-containing 5-membered hetero ring which may further be substituted, said compounds having hypoglycemic and hypolipidemic activity.

It is an objective of the present invention to provide further compounds having CRTH2 antagonistic activity.

Preferably the compounds of the present invention have enhanced chemical stability, enhanced pharmacokinetic properties (PK) and/or enhanced activity in a whole cell assay.

DETAILED DESCRIPTION OF THE INVENTION

The present invention relates to pyrazole compounds of formula (I) and pharmaceutically acceptable salts thereof,

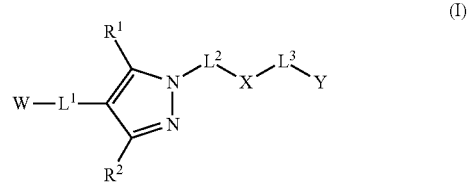

wherein

W is selected from hydroxycarbonyl, —C(O)—NH—S(O)$_2$—$R^a$, tetrazol-5-yl, 1,2,4-oxadiazol-5(4H)-on-3-yl and 1,3,4-oxadiazol-2(3H)-on-5-yl, wherein $R^a$ is selected from $C_1$-$C_6$-alkyl, $C_1$-$C_6$-haloalkyl, cyclopropyl, phenyl and tolyl;

$L^1$ is methylene; ethylene, ethenylene or acetylene, wherein each carbon atom in methylene or ethylene is unsubstituted or carries 1 or 2 radicals selected independently from each other from hydroxy, halogen, $C_1$-$C_6$-alkyl, $C_1$-$C_6$-haloalkyl, $C_1$-$C_6$-alkoxy, $C_1$-$C_6$-haloalkoxy and $C_3$-$C_6$-cycloalkyl and wherein two radicals bound to the same carbon atom of methylene or ethylene together with said carbon atom may form a 3- to 8-membered ring, wherein said ring may contain 1 or 2 heteroatoms selected from O, N and S as ring member and wherein the ring members of said ring may optionally be independently substituted by hydroxy, halogen, $C_1$-$C_6$-alkyl, $C_1$-$C_6$-haloalkyl, $C_1$-$C_6$-alkoxy, $C_1$-$C_6$-haloalkoxy and $C_3$-$C_6$-cycloalkyl, and/or wherein two radicals bound to the same carbon atom of methylene or ethylene together with said carbon atom may form a carbonyl group;

$L^2$ is methylene or ethylene, wherein each carbon atom in methylene or ethylene is unsubstituted or carries 1 or 2 radicals selected independently from each other from hydroxy, halogen, $C_1$-$C_6$-alkyl, $C_1$-$C_6$-haloalkyl and $C_3$-$C_6$-cycloalkyl and wherein two radicals bound to the same carbon atom of methylene or ethylene together with said carbon atom may form a carbonyl group and wherein two radicals bound to the same carbon atom of methylene or ethylene together with said carbon atom may form a 3- to 8-membered ring, wherein said ring may contain 1 or 2 heteroatoms selected from O, N and S as ring member and wherein the ring members of said ring may optionally be independently substituted by hydroxy, halogen, $C_1$-$C_6$-alkyl, $C_1$-$C_6$-haloalkyl, $C_1$-$C_6$-alkoxy, $C_1$-$C_6$-haloalkoxy and $C_3$-$C_8$-cycloalkyl;

X is a 6-membered carbocyclic or heterocyclic moiety selected from phen-1,4-ylene, pyridin-2,5-ylene, pyridazin-3,6-ylene, pyrimidin-2,5-ylene and pyrazin-2,5-ylene, wherein the aforementioned moieties X are unsubstituted or may carry 1, 2 or 3 radicals selected independently from each other from hydroxy, halogen, $C_1$-$C_6$-alkyl, $C_1$-$C_6$-haloalkyl, $C_1$-$C_6$-alkoxy, $C_1$-$C_6$-haloalkoxy and $C_3$-$C_8$-cycloalkyl;

$L^3$ is selected from —CH=CH—, —C≡C—, —$CR^bR^c$—CH(OH)—, —$CR^bR^c$—C(O)—, —$CR^bR^c$—O—, —$CR^b$ $R^c$—$NR^d$—, —$CR^bR^c$—$S(O)_m$—, —CH(OH)—, —C(O)—, —C(O)—$NR^d$—, —O—, —$NR^d$—, —$NR^d$—C(O)—, —$NR^dC(O)$—O—, —$NR^d$—C(O)—$NR^e$—, —$NR^d$—$S(O)_n$—, —$S(O)_p$— and —$S(O)_q$—$NR^d$—, wherein m, n and p are 0, 1 or 2 and q is 1, or 2, and wherein $R^b$ and $R^c$ are independently from each other selected from H, $C_1$-$C_6$-alkyl, $C_3$-$C_8$-cycloalkyl and wherein two radicals $R^b$ and $R^c$ bound to the same carbon atom together with said carbon atom may form a 3- to 8-membered ring, wherein said ring may contain 1 or 2 heteroatoms selected from O, N and S as ring member and wherein the ring members of said ring may optionally be independently substituted by hydroxy, halogen, $C_1$-$C_6$-alkyl, $C_1$-$C_6$-haloalkyl, $C_1$-$C_6$-alkoxy, $C_1$-$C_6$-haloalkoxy and $C_3$-$C_8$-cycloalkyl, and wherein $R^d$ and $R^e$ independently from each other are H or $C_1$-$C_6$-alkyl;

Y is selected from H, $C_1$-$C_6$-alkyl, $C_3$-$C_8$-cycloalkyl, $C_3$-$C_8$-cycloalkyl-$C_1$-$C_6$-alkyl, $C_3$-$C_8$-cycloalkyl-$C_2$-$C_6$-alkenyl, phenyl, phenyl-$C_1$-$C_6$-alkyl, phenyl-$C_2$-$C_6$-alkenyl, naphthyl, naphthyl-$C_1$-$C_6$-alkyl, naphthyl-$C_2$-$C_6$-alkenyl, heterocyclyl, heterocyclyl-$C_1$-$C_6$-alkyl and heterocyclyl-$C_2$-$C_6$-alkenyl, wherein the $C_1$-$C_6$-alkyl and $C_2$-$C_6$-alkenyl moieties in the aforementioned radicals Y are unsubstituted or carry at least one substituent selected from hydroxy, halogen, cyano, nitro, $C_1$-$C_6$-alkoxy, $C_1$-$C_6$-haloalkoxy, $C_1$-$C_6$-alkylamino, di-$C_1$-$C_6$-alkylamino and $C_1$-$C_6$-alkylsulfonyl and wherein two of said substituents bound to the same carbon atom of the $C_1$-$C_6$-alkyl moieties together with said carbon atom may form a 3- to 8-membered ring, wherein said ring may contain 1 or 2 heteroatoms selected from O, N and S as ring member, and wherein the $C_3$-$C_8$-cycloalkyl, phenyl, naphthyl or heterocyclyl moieties in the aforementioned radicals Y are unsubstituted or carry at least one substituent selected from hydroxy, halogen, cyano, nitro, $SF_5$, —C(O)$NR^f$ $R^g$, $C_1$-$C_6$ alkyl, hydroxy-$C_1$-$C_5$-alkyl, $C_1$-$C_6$-alkoxy-$C_1$-$C_6$-alkyl, $C_3$-$C_8$-cycloalkyl, $C_1$-$C_6$ haloalkyl, $C_1$-$C_6$-alkoxy, $C_1$-$C_6$-alkoxy-$C_1$-$C_6$-alkoxy, $C_1$-$C_6$-haloalkoxy, $C_3$-$C_8$-cycloalkoxy, $C_1$-$C_6$-alkylamino, di-$C_1$-$C_6$-alkylamino, $C_1$-$C_6$-alkylsulfonyl, phenyl, phenoxy, 5- or 6-membered heterocyclyl and 5- or 6-membered heterocyclyloxy, wherein $R^f$ and $R^g$ are independently from each other selected from H, $C_1$-$C_6$ alkyl, $C_1$-$C_6$-haloalkyl, $C_3$-$C_8$-cycloalkyl, $C_3$-$C_8$-cycloalkenyl and heterocyclyl or $R^f$ and $R^g$ together with the nitrogen atom to which they are bound form a cyclic amine, which may comprise a further heteroatom selected from O, N and S as a ring member and/or wherein two radicals bound to the same carbon atom of the $C_3$-$C_8$-cycloalkyl or heterocyclyl moieties in the aforementioned radicals Y together with said carbon atom may form a carbonyl group and/or wherein the $C_3$-$C_8$-cycloalkyl, phenyl, naphthyl or heterocyclyl moieties in the aforementioned radicals Y may carry a fused carbocyclic or heterocyclic moiety, wherein said fused carbocyclic or heterocyclic moiety is unsubstituted or carries at least one substituent selected from hydroxy, halogen, cyano, nitro, $C_1$-$C_6$-alkyl, $C_3$-$C_8$-cycloalkyl, $C_1$-$C_6$-haloalkyl, $C_1$-$C_6$-alkoxy, $C_1$-$C_6$-haloalkoxy, $C_1$-$C_6$-alkylamino, di-$C_1$-$C_6$-alkylamino, $C_1$-$C_6$-alkylsulfonyl, phenyl and 5- or 6-membered hetaryl and/or wherein two radicals bound to the same carbon atom of the fused carbocyclic or heterocyclic moiety together with said carbon atom may form a carbonyl group; and wherein $R^1$ and $R^2$ independently from each other are selected from H, halogen, $C_1$-$C_6$-alkyl, $C_2$-$C_6$-alkenyl, $C_2$-$C_6$-alkynyl, $C_1$-$C_6$-alkoxy, $C_3$-$C_8$-cycloalkyl, $C_3$-$C_8$-cycloalkyl-$C_1$-$C_6$-alkyl, $C_3$-$C_8$-cycloalkyl-$C_2$-$C_6$-alkenyl, $C_3$-$C_8$-cycloalkenyl, $C_3$-$C_8$-cycloalkenyl-$C_1$-$C_6$-alkyl, $C_3$-$C_8$-cycloalkenyl-$C_2$-$C_6$-alkenyl, phenyl, phenyl-$C_1$-$C_6$-alkyl, phenyl-$C_2$-$C_6$-alkenyl, naphthyl, naphthyl-$C_1$-$C_6$-alkyl, naphthyl-$C_2$-$C_6$-alkenyl, heterocyclyl, heterocyclyl-$C_1$-$C_6$-alkyl, and heterocyclyl-$C_2$-$C_6$-alkenyl, wherein the $C_1$-$C_6$-alkyl, $C_2$-$C_6$-alkenyl and $C_2$-$C_6$-alkynyl moieties in the aforementioned radicals $R^1$ and $R^2$ are unsubstituted or carry at least one substituent selected from hydroxy, halogen, cyano, nitro, $C_1$-$C_6$-alkoxy, $C_1$-$C_6$-haloalkoxy, $C_1$-$C_6$-alkylamino, di-$C_1$-$C_6$-alkylamino and $C_1$-$C_6$-alkylsulfonyl and/or wherein two radicals bound to the same carbon atom of said $C_1$-$C_6$-alkyl, $C_2$-$C_6$-alkenyl and $C_2$-$C_6$-alkynyl moieties in the aforementioned radicals $R^1$ and $R^2$ together with said carbon atom may form a carbonyl group, and wherein the $C_3$-$C_8$-cycloalkyl, cycloalkenyl, phenyl, naphthyl and heterocyclyl moieties in the aforementioned radicals $R^1$ and $R^2$ are unsubstituted or carry at least one substituent selected from hydroxy, halogen, cyano, nitro, $C_1$-$C_6$-alkyl, $C_3$-$C_8$-cycloalkyl, $C_1$-$C_6$-haloalkyl, $C_1$-$C_6$-alkoxy, $C_1$-$C_6$-haloalkoxy, $C_1$-$C_6$-alkylamino, di-$C_1$-$C_6$-alkylamino, $C_1$-$C_6$-alkylsulfonyl, phenyl and 5- or 6-membered hetaryl and/or wherein two radicals bound to the same carbon atom of said $C_3$-$C_8$-cycloalkyl, $C_3$-$C_8$-cycloalkenyl and heterocyclyl moieties of the radicals $R^1$ and $R^2$ together with said carbon atom may form a carbonyl group, and wherein $R^f$ and $R^g$ are independently from each other selected from H, $C_1$-$C_6$-alkyl, $C_1$-$C_6$-haloalkyl, $C_3$-$C_8$-cycloalkyl, $C_3$-$C_3$-cycloalkenyl and heterocyclyl or $R^f$ and $R^g$ together with the nitrogen atom to which they are bound form a cyclic amine, which may comprise a further heteroatom selected from O, N and S as a ring member.

Surprisingly it has been found that the compounds of formula (I) according to the present invention have significant CRTH2 antagonistic activity. Further it has been found that said compounds generally have enhanced chemical stability, enhanced pharmacokinetic properties (PK) and/or enhanced activity in a whole cell assay.

Thus the pyrazole compounds of formula I according to the present invention are suitable for the treatment of diseases related to CRTH2-activity.

Accordingly the present invention further relates to the use of pyrazole compounds of formula (I) according to the present invention as medicaments.

Furthermore the present invention relates to the use of compounds of formula (I) for preparing a medicament for the treatment of diseases related to CRTH2-activity. More specifically the present invention relates to the use of pyrazole compounds of formula (I) for preparing a medicament for the prevention and/or treatment of inflammatory, infectious and immunoregulatory disorders, respiratory or gastrointestinal diseases or complaints, inflammatory diseases of the joints and allergic diseases of the nasopharynx, eyes, and skin.

Furthermore the present invention relates to compounds of formula (I) for use as a medicament for the treatment of diseases related to CRTH2-activity. More specifically the present invention relates to pyrazole compounds of formula (I) for use as a medicament for the prevention and/or treatment of inflammatory, infectious and immunoregulatory disorders, respiratory or gastrointestinal diseases or complaints, inflammatory diseases of the joints and allergic diseases of the nasopharynx, eyes, and skin.

Furthermore the present invention relates to pharmaceutical formulations, containing one or more of the pyrazole compounds of formula (I) according to any the present invention as sole active substance or in combination with one or more active substances selected from among betamimetics, anticholinergics, corticosteroids, PDE4 inhibitors, LTD4 antagonists, EGFR inhibitors, CCR3 antagonists, CCR5 antagonists, CCR9 antagonists, 5-LO inhibitors, histamine-receptor antagonists, SYK inhibitors and sulphonamides.

The activity in an whole cell eosinophil shape change assay of the compounds of the invention can be determined, for example, according to the following references: (i) Mathiesen J M, Ulven T, Martini L, Gerlach L O, Heinemann A, Kostenis E. Identification of indol derivatives exclusively interfering with a G protein-independent signalling pathway of the prostaglandin D2 receptor CRTH2. Mol Pharmacol. 2005 August; 68(2):393-402; (ii) Schuligoi R, Schmidt R, Geisslinger G, Kollroser M, Peskar B A, Heinemann A. PGD2 metabolism in plasma: kinetics and relationship with bioactivity on DP1 and CRTH2 receptors. Biochem Pharmacol. 2007 Jun. 30; 74(1): 107-17; (iii) Royer J F, Schratl P, Carrillo J J, Jupp R, Barker J, Weyman-Jones C, Beri R, Sargent C, Schmidt J A, Lang-Loidolt D, Heinemann A. A novel antagonist of prostaglandin D2 blocks the locomotion of eosinophils and basophils. Eur J Clin Invest. 2008 September; 38(9):663-71.

The chemical stability of the compounds of the invention can be determined, for example, under the following conditions: (i) 3 days incubation at 60° C. in 0.1 N HCl (hydrolytic stability under acidc conditions); (ii) 3 days incubation at 60° C. in pH 4.0 buffer solution (hydrolytic stability under weakly acidic conditions); (iii) 3 days incubation at 60° C. in pH 7.4 buffer solution (hydrolytic stability at physiological pH); (iv) 3 days incubation at 20° C. in 0.3 hydrogen peroxide (stability against oxidants); (v) 24 h incubation under UV-radiation (lambda=300-800 nm, P=250 W/m2) in water (stability against light). The kinetics of degradation can, for example, be determined by HPLC analysis.

The pharmacokinetic properties (PK) of the compounds of the invention can be determined in pre-clinical animal species, for example, mouse, rat, dog, guinea pig, mini pig, cynomolgus monkey, rhesus monkey. The pharmacokinetic properties of a compound can be described, for example, by the following parameters: Mean residence time, half-life, volume-of-distribution, AUC (area under the curve), clearance, bioavailability after oral administration.

USED TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals or moieties defined below, the number of carbon atoms is often specified preceding the group. As an example "$C_1$-$C_6$-alkyl" means an alkyl group or radical having 1 to 6 carbon atoms.

In general, for groups comprising two or more subgroups, the last named group is the radical attachment point.

Unless otherwise specified, conventional definitions of terms control and conventional stable atom valences are presumed and achieved in all formulas and groups.

In general, all tautomeric forms and isomeric forms and mixtures, whether individual geometric isomers or optical isomers or racemic or non-racemic mixtures of isomers, of a chemical structure or compound are comprised, unless the specific stereochemistry or isomeric form is specifically indicated in the compound name or structure.

The term "substituted" as used herein, means that any one or more hydrogens on the designated atom, moiety or radical is replaced with a selection from the indicated group of radicals, provided that the designated atom's normal valence is not exceeded, and that the substitution results in a stable compound.

The compounds disclosed herein can exist as pharmaceutically acceptable salts. The present invention includes compounds in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCH, Zurich, Switzerland, 2002).

The term "pharmaceutically acceptable salt," as used herein, represents salts or zwitterionic forms of the compounds disclosed herein which are water or oil-soluble or dispersible and pharmaceutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphor sulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylene sulfonate, methane sulfonate, naphthylene sulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric acid, hydrobromic acid, sulfuric acid and phosphoric acid, and organic acids such as oxalic acid, maleic acid, succinic acid and citric acid. Salts can also be formed by coordination of the compounds with an alkali metal or alkaline earth ion. Hence, the present invention comprises sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine and piperazine.

While it may be possible for the compounds of the present invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carrier and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers and excipients may be used as suitable and as understood in the art; e.g. in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The term "halogen" as used herein denotes a halogen substituent selected from fluoro, chloro, bromo or iodo.

The term "$C_1$-$C_6$-alkyl" as used herein (including the alkyl moieties of $C_1$-$C_6$-alkoxy, $C_1$-$C_6$-alkylamino, di-$C_1$-$C_6$-alkylamino, $C_1$-$C_6$-alkylthio and the like) denotes branched and unbranched alkyl moieties with 1 to 6 carbon atoms attached to the remaining compound at any position of the alkyl chain. The term "$C_1$-$C_4$-alkyl" accordingly denotes a branched or unbranched alkyl moiety with 1 to 4 carbon atoms. "$C_1$-$C_4$-alkyl" is generally preferred. Examples of "$C_1$-$C_6$-alkyl" include: methyl, ethyl, n-propyl, iso-propyl, n-butyl, iso-butyl, sec-, butyl, tert-butyl, n-pentyl, iso-pentyl, neo-pentyl or hexyl. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

The term "$C_1$-$C_6$-haloalkyl" as used herein (including the alkyl moieties of $C_1$-$C_6$-haloalkoxy, $C_1$-$C_6$-haloalkylamino, di-$C_1$-$C_6$-haloalkylamino, $C_1$-$C_6$-haloalkylthio and the like) denotes branched and unbranched alkyl moieties with 1 to 6 carbon atoms wherein one or more hydrogen atoms are replaced by a halogen atom selected from among fluorine, chlorine or bromine, preferably fluorine and chlorine, particularly preferably fluorine. The term "$C_1$-$C_4$-haloalkyl" accordingly denotes branched and unbranched alkyl moieties with 1 to 4 carbon atoms, wherein one or more hydrogen atoms are replaced analogously to what was stated above. $C_1$-$C_4$-haloalkyl is generally preferred. Preferred examples include: $CH_2F$, $CHF_2$ and $CF_3$.

The term "$C_2$-$C_6$-alkenyl" as used herein (including the alkenyl moieties of other radicals) denotes branched and unbranched alkenyl groups with 2 to 6 carbon atoms attached to the remaining compound at any position of the alkenyl chain and having at least one double bond. The term "$C_2$-$C_4$-alkenyl" accordingly denotes branched and unbranched alkenyl moieties with 2 to 4 carbon atoms. Preferred are alkenyl moieties with 2 to 4 carbon atoms. Examples include: ethenyl or vinyl, propenyl, butenyl, pentenyl or hexenyl. Unless otherwise stated, the definitions propenyl, butenyl, pentenyl and hexenyl include all possible isomeric forms of the moieties in question. Thus, for example, propenyl includes 1-propenyl and 2-propenyl, butenyl includes 1-, 2- and 3-butenyl, 1-methyl-1-propenyl, 1-methyl-2-propenyl etc.

The term "$C_2$-$C_6$-alkynyl" as used herein (including the alkynyl moieties of other radicals) denotes branched and unbranched alkynyl groups with 2 to 6 carbon atoms attached to the remaining compound at any position of the alkynyl chain and having at least one triple bond. The term "$C_2$-$C_4$-alkynyl" accordingly denotes branched and unbranched alkynyl moieties with 2 to 4 carbon atoms. Alkynyl moieties with 2 to 4 carbon atoms are preferred. Examples include: ethynyl, propynyl, butynyl, pentynyl, or hexynyl. Unless stated otherwise, the definitions propynyl, butynyl, pentynyl and hexynyl include all the possible isomeric forms of the respective moieties. Thus, for example, propynyl includes 1-propynyl and 2-propynyl, butynyl includes 1-, 2- and 3-butynyl, 1-methyl-1-propynyl, 1-methyl-2-propynyl etc.

The term "$C_3$-$C_8$-cycloalkyl" as used herein (including the cycloalkyl moieties of other radicals) denotes cyclopropyl, cyclobutyl, cyclopentyl, cyclohexyl, cycloheptyl and cyclooctyl. Preferred are cyclic alkyl groups with 3 to 6 carbon atoms, such as cyclopropyl, cyclopentyl and cyclohexyl.

The term "$C_3$-$C_8$-cycloalkenyl" as used herein (including the cycloalkenyl moieties of other radicals) denotes carbocyclic radicals having 3 to 8 carbon atoms and containing at least one, preferably one or two, non-conjugated double bonds. Examples are cyclopentenyl, cyclopantadienyl, cyclohexenyl and cyclohexadienyl.

The term "heterocyclyl" as used herein (including the heterocyclyl moieties of other radicals) denotes 5- to 7-membered heterocyclic radicals and 5- to 10-membered, bicyclic heterocyclic radicals, containing one, two or three heteroatoms, selected from O, N and S as ring members. The heterocyclyl may be linked to the molecule by a carbon atom or, if present, by a nitrogen atom. The term "heterocyclyl" as used herein encompasses saturated or partially unsaturated heterocyclyl as well as hetaryl.

The term "saturated or partially unsaturated heterocyclyl" as used herein (including the heterocyclyl moieties of other radicals) denotes 5- to 7-membered monocyclic heterocyclic radicals as defined above containing a number of double bonds such that no aromatic system is formed as well as 5- to 10-membered bicyclic heterocyclic radicals as defined above containing a number of double bonds such that no aromatic system is formed in at least one of the cycles.

Examples of monocyclic saturated or partially unsaturated heterocyclyl include pyrrolidine, tetrahydrofurane, tetrahydrothiophene, thiazolidine, dioxolane, piperidine, tetrahydropyrane, tetrahydrothiopyrane, piperazine, morpholine, thiomorpholine, oxazepane, and the like.

Examples of bicyclic saturated or partially unsaturated heterocyclyl include dihydropyrrolizine, pyrrolizine, tetrahydroquinoline, tetrahydroisoquinoline, tetrahydroimidazopyridine, tetrahydropyrazolopyridine, benzopyrane, benzodiazepine, and the like.

The term "hetaryl" as used herein (including the heterocyclyl moieties of other radicals) denotes 5- to 7-membered monocyclic heterocyclic radicals as defined above containing a number of double bonds such that an aromatic system is formed as well as 5- to 10-membered bicyclic heterocyclic radicals as defined above containing a number of double bonds such that an aromatic system is formed in both cycles.

Examples of monocyclic aromatic heterocyclyl include furan, thiazole, pyrrole, thiophene, pyrazole, imidazole, thiadiazole, 1,2,3-triazole, 1,2,4-triazole, tetrazole, oxazole, oxadiazole, pyridine, pyridazine, pyrimidine, pyrazine, and the like.

Examples of bicyclic aromatic heterocyclyl include pyrrolizine, indol, indolizine, isoindol, indazol, purine, quinoline, isoquinoline, benzimidazol, benzofuran, benzothiazol, benzoisothiazol, pyridopyrimidine, pteridine, pyrimidopyrimidine, imidazopyridine, pyrazolopyridine, and the like.

The term "fused carbocyclic or heterocyclic moiety" as used herein denotes $C_3$-$C_8$-cycloalkyl, $C_3$-$C_8$-cycloalkenyl, benzene and heterocyclyl moieties as defined above, wherein said moieties share at least one bond with the cyclic moiety they are bound to. As an example benzene fused to benzene is naphthalene. Preferred are fused cyclic moieties sharing one bond with the cyclic moiety they are fused to. Further preferred the fused moiety is benzene.

The term "3- to 8-membered ring formed by two radicals together with the carbon atom they are bound, wherein said ring may contain 1 or 2 heteroatoms selected from O, N and S as ring member" as used herein denotes $C_3$-$C_8$-cycloalkyl, $C_3$-$C_8$-cycloalkenyl and heterocyclyl moieties as defined above.

The term "cyclic amine formed by two radicals together with the nitrogen atom to which they are bound, wherein said ring may comprise a further heteroatom selected from O, N and S as a ring member" as used herein denotes cyclic amines having 3 to 8, preferably 5 or 6, ring members. Examples of such formed amines are pyrrolidine, piperidine, piperazine, morpholine, pyrrol, imidazole, and the like.

The terms "heterocyclyl-$C_1$-$C_6$-alkyl", "$C_3$-$C_8$-cycloalkyl-$C_1$-$C_6$-alkyl", "phenyl-$C_1$-$C_6$-alkyl" and "naphthyl-$C_1$-$C_6$-alkyl" as used herein denote alkyl moieties as defined above having 1 to 6 carbon atoms, wherein any one of the hydrogen atoms is replaced by a cyclic moiety as defined above. In these terms the alkyl moiety preferably has 1 to 4 carbon atoms ($C_1$-$C_4$-alkyl). More preferably the alkyl moiety is methyl or ethyl, and most preferred methyl. Preferred examples of phenyl-$C_1$-$C_6$-alkyl are benzyl or phenethyl.

The terms "heterocyclyl-$C_2$-$C_6$-alkenyl", "$C_3$-$C_8$-cycloalkyl-$C_2$-$C_6$-alkenyl", "phenyl-$C_2$-$C_6$-alkenyl" and "naphthyl-$C_2$-$C_6$-alkenyl" as used herein denote alkenyl moieties as defined above having 2 to 6 carbon atoms, wherein any one of the hydrogen atoms is replaced by a cyclic moiety as defined above. In these terms the alkenyl moiety preferably has 2 to 4 carbon atoms ($C_2$-$C_4$-alkenyl). More preferably the alkenyl moiety is ethenyl. A preferred example of phenyl-$C_2$-$C_6$-alkenyl is phenethenyl.

The specific and preferred definitions given for the individual radicals and moieties W, $L^1$, $L^2$, X, $L^3$, Y, $R^1$ and $R^2$ herein below are valuable on their own as well as in combination. As will be understood preferred are compounds of formula (I) wherein one or more of the individual radicals and moieties W, $L^1$, $L^2$, X, $L^3$, Y, $R^1$ and $R^2$ have one of the meanings indicated as preferred herein-below and wherein the remaining radicals and moities are as specified hereinbefore. Most preferred are compounds of formula (I) wherein all of the individual radicals and moieties W, $L^2$, X, $L^3$, Y, $R^1$ and $R^2$ have one of the meanings indicated as preferred hereinbelow.

Preferred are pyrazole compounds of formula (I) according to the invention, wherein W is hydroxycarbonyl and —C(O)—NH—S(O)$_2$—$R^a$. In the radical W the radical $R^a$ preferably is selected from $C_1$-$C_4$-alkyl, $C_1$-$C_2$-haloalkyl, cyclopropyl, phenyl and tolyl. More specifically the radical $R^a$ is selected from methyl, ethyl, trifluoromethyl, cyclopropyl, phenyl and tolyl.

More preferred according to the present invention are compounds of formula (I) wherein W is hydroxycarbonyl.

Preferred as well are pyrazole compounds of formula (I) according to the invention, wherein $L^1$ is methylene which is unsubstituted or carries 1 or 2 radicals as defined above.

Radicals carried by the moiety $L^1$ if present preferably are selected from $C_1$-$C_4$-alkyl and $C_3$-$C_6$-cycloalkyl or two of said radicals bound to the same carbon atom of $L^1$ together with said carbon atom form a 3- to 6-membered ring. More preferably said radicals if present are selected from $C_1$-$C_4$-alkyl.

More preferred are pyrazole compounds of formula (I), wherein $L^1$ is unsubstituted, especially wherein $L^1$ is unsubstituted methylene.

Preferred as well are pyrazole compounds of formula (I) according to the invention, wherein $L^2$ is methylene which is unsubstituted or carries 1 or 2 radicals as defined above.

Radicals carried by the moiety $L^2$ if present preferably are selected from $C_1$-$C_4$-alkyl and $C_3$-$C_6$-cycloalkyl or two of said radicals bound to the same carbon atom of $L^2$ together with said carbon atom form a 3- to 6-membered ring. More preferably said radicals if present are selected from $C_1$-$C_4$-alkyl.

More preferred are pyrazole compounds of formula (I) according to the invention, wherein $L^2$ is unsubstituted, especially wherein $L^2$ is unsubstituted methylene.

Preferred as well are pyrazole compounds of formula (I) according to the present invention, wherein X is phen-1,4-ylene or pyridin-2,5-ylene, which are unsubstituted or carry 1, 2 or 3 radicals as defined above.

Radicals carried by the moiety X if present preferably are selected from halogen, $C_1$-$C_6$-alkyl, $C_1$-$C_6$-haloalkyl and $C_3$-$C_8$-cycloalkyl. More preferably radicals carried by X are $C_1$-$C_4$-alkyl, $C_1$-$C_2$-haloalkyl or $C_3$-$C_6$-cycloalkyl.

More preferred are pyrazole compounds of formula (I) according to the invention, wherein X is phen-1,4-ylene which is unsubstituted or carries 1, 2 or 3 radicals as defined above. In particular X is unsubstituted phen-1,4-ylen.

Preferred as well are pyrazole compounds of formula (I) according to the present invention, wherein $L^3$ is selected from —CH=CH—, —C≡C—, —CR$^b$R$^c$—O—, —CR$^b$R$^c$—S(O)$_m$—, —CH(OH)—, —C(O)—, —C(O)—NR$^d$—, —O—, —NR$^d$—, —NR$^d$—C(O)—, —NR$^d$C(O)

—O—, —NR$^d$—C(O)—NR$^e$—, —NR$^d$—S(O)$_n$—, —S(O)$_p$— and —S(O)$_q$—NR$^d$—, wherein m, n, p, q, R$^b$, R$^d$ and R$^e$ are as defined above.

More preferred are pyrazole compounds of formula (I), wherein L$^3$ is selected from —CR$^b$R$^c$—O—, —C(O)—NR$^d$—, —O—, —NR$^d$—C(O)—, —NR$^d$C(O)O—, —NR$^d$C(O)—NR$^e$—, —NR$^d$—S(O)$_n$— and —S(O)$_q$—NR$^d$—, wherein n, q, and R$^b$, R$^c$, R$^d$ and R$^e$ are as defined above.

Particularly preferred are pyrazole compounds of formula (I) according to the present invention, wherein L$^3$ is —C(O)—NR$^d$—, —NR$^d$—C(O)—, —NR$^d$C(O)O— or —S(O)$_2$—NR$^d$—, wherein R$^d$ is as defined above.

In the above mentioned moieties L$^3$ the radicals R$^b$, R$^c$ preferably are H or C$_1$-C$_6$-alkyl. More preferably R$^b$ and R$^c$ are H or C$_1$-C$_4$-alkyl. In particular R$^b$ and R$^c$ are H.

In the above mentioned moieties L$^3$ the radicals R$^d$, R$^e$ preferably are H or C$_1$-C$_6$-alkyl. More preferably R$^d$ and R$^e$ are H or C$_1$-C$_4$-alkyl. In particular R$^d$ and R$^e$ are H.

One specific embodiment of the invention relates to pyrazole compounds of formula (I) according to the invention, wherein L$^3$ is —C(O)—NR$^d$—, wherein R$^d$ is as defined above.

Another specific embodiment of the invention relates to pyrazole compounds of formula (I) according to the invention, wherein L$^3$ is —NR$^d$—C(O)—, wherein R$^d$ is as defined above.

Another specific embodiment of the invention relates to pyrazole compounds of formula (I) according to the invention, wherein L$^3$ is —NR$^d$C(O)O—, wherein R$^d$ is as defined above.

Another specific embodiment of the invention relates to pyrazole compounds of formula (I) according to the invention, wherein L$^3$ is —S(O)$_2$—NR$^d$—, wherein R$^d$ is as defined above.

Preferred as well are pyrazole compounds of formula (I) according to the invention, wherein Y is selected from phenyl, phenyl-C$_1$-C$_6$-alkyl, phenyl-C$_2$-C$_6$-alkenyl, naphthyl, naphthyl-C$_1$-C$_6$-alkyl, naphthyl-C$_2$-C$_6$-alkenyl, wherein the phenyl or naphthyl moieties in the aforementioned radicals Y are unsubstituted or carry at least one substituent as defined above and/or wherein the phenyl or naphthyl moieties in the aforementioned radicals Y may carry a fused carbocyclic or heterocyclic moiety, wherein said fused carbocyclic or heterocyclic moiety is unsubstituted or carries at least one substituent selected from hydroxy, halogen, cyano, nitro, C$_1$-C$_6$-alkyl, C$_3$-C$_8$-cycloalkyl, C$_1$-C$_6$-haloalkyl, C$_1$-C$_6$-alkoxy, C$_1$-C$_6$-haloalkoxy, C$_1$-C$_6$-alkylamino, di-C$_1$-C$_6$-alkylamino, C$_1$-C$_6$-alkylsulfonyl, phenyl and 5- or 6-membered hetaryl and/or wherein two radicals bound to the same carbon atom of the fused carbocyclic or heterocyclic moiety together with said carbon atom may form a carbonyl group.

More preferred are pyrazole compounds of formula (I) according to the invention, wherein Y is selected from phenyl, benzyl, phenethyl, phenethenyl, naphthyl, naphthylmethyl, naphthylethyl, naphthylethenyl, wherein the phenyl and naphthyl moieties in the aforementioned radicals Y are unsubstituted or carry at least one substituent selected from as defined above.

Particularly preferred are pyrazole compounds of formula (I) according to the invention, wherein Y is selected from phenyl and naphthyl, wherein the phenyl and naphthyl moieties in the aforementioned radicals Y are unsubstituted or carry at least one substituent as defined above.

Radicals carried by the moiety Y if present preferably are selected from hydroxy, halogen, cyano, nitro, C$_1$-C$_6$-alkyl, C$_3$-C$_8$-cycloalkyl, C$_1$-C$_6$-haloalkyl, C$_1$-C$_6$-alkoxy, C$_1$-C$_6$-haloalkoxy, C$_1$-C$_6$-alkylamino, di-C$_1$-C$_6$-alkylamino, C$_1$-C$_6$-alkylsulfonyl, phenyl and 5- or 6-membered heterocyclyl.

More preferably radicals carried by the moiety Y if present are selected from halogen, C$_1$-C$_4$-alkyl, C$_3$-C$_6$-cycloalkyl, C$_1$-C$_2$-haloalkyl, C$_1$-C$_4$-alkoxy, C$_1$-C$_2$-haloalkoxy, C$_1$-C$_4$-alkylamino and di-C$_1$-C$_4$-alkylamino.

Preferred as well are pyrazole compounds of formula (I) according to the invention, wherein R$^1$ and R$^2$ independently from each other are selected from C$_1$-C$_6$-alkyl, C$_3$-C$_8$-cycloalkyl, phenyl and naphthyl.

More preferred are pyrazole compounds of formula (I) according to the invention, wherein R$^1$ and R$^2$ independently from each other are selected from C$_1$-C$_4$-alkyl, C$_3$-C$_6$-cycloalkyl and phenyl.

Particularly preferred are pyrazole compounds of formula (I) according to the invention, wherein at least one of the radicals R$^1$ and R$^2$ is C$_1$-C$_4$-alkyl. More particularly at least one of the radicals R$^1$ and R$^2$ is methyl One particular embodiment of the invention relates to pyrazole compounds of formula (I), wherein l2 denotes methylene, X is 1,4-phenylene and L$^2$, L$^3$, W, Y, R$^1$, R$^2$ have one of the meanings indicated above (pyrazole compounds of formula (I.A)).

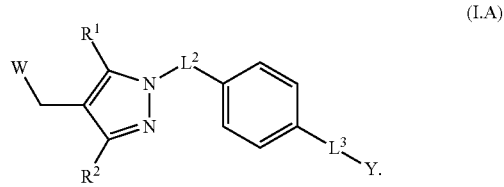

(I.A)

One particular embodiment of the invention relates to pyrazole compounds of formula (I), wherein L$^1$ and L$^2$ are unsubstituted methylene, X is 1,4-phenylene and L$^3$ is —C(O)—NR$^d$—, wherein R$^d$ is H or C$_1$-C$_6$-alkyl, and W, Y, R$^1$, R$^2$ have one of the meanings indicated above (pyrazole compounds of formula (I.A1)).

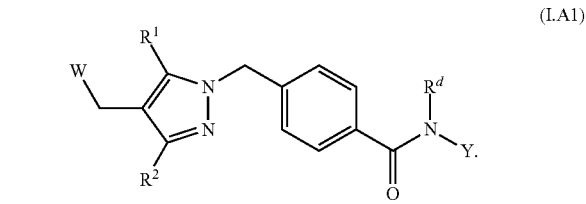

(I.A1)

Another particular embodiment of the invention relates to pyrazole compounds of formula (I), wherein L$^1$ and L$^2$ are unsubstituted methylene, X is 1,4-phenylene, L$^3$ is —NR$^d$—C(O)—, wherein R$^d$ is H or C$_1$-C$_6$-alkyl, and W, Y, R$^1$ and R$^2$ have one of the meanings indicated above (pyrazole compounds of formula (I.A2)).

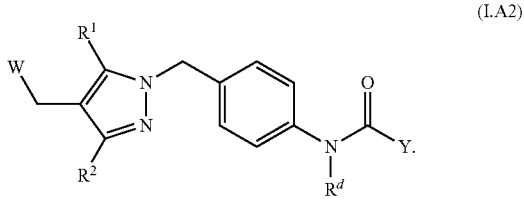

(I.A2)

Another particular embodiment of the invention relates to pyrazole compounds of formula (I), wherein $L^1$ and $L^2$ are unsubstituted methylene, X is 1,4-phenylene, $L^3$ is —$NR^d$—C(O)O—, wherein $R^d$ is H or $C_1$-$C_6$-alkyl, and W, Y, $R^1$ and $R^2$ have one of the meanings indicated above (pyrazole compounds of formula (I.A3)).

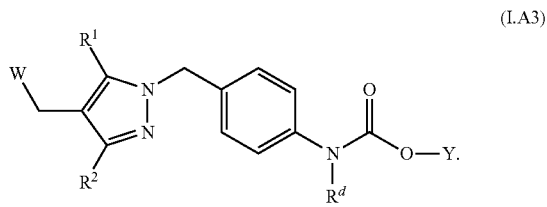

(I.A3)

Another particular embodiment of the invention relates to pyrazole compounds of formula (I), wherein $L^1$ and $L^2$ are unsubstituted methylene, X is 1,4-phenylene, $L^3$ is —$S(O)_2$—$NR^d$—, wherein $R^d$ is H or $C_1$-$C_6$-alkyl, and W, Y, $R^1$ and $R^2$ have one of the meanings indicated above (pyrazole compounds of formula (I.A4)).

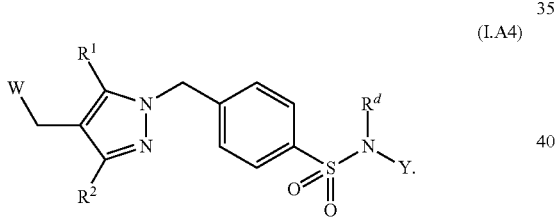

(I.A4)

Preferred are pyrazole compounds of formulae (I.A1), (I.A2), (I.A3) or (I.A4), wherein Y is selected from phenyl and naphthyl, wherein the phenyl and naphthyl moieties in the aforementioned radicals Y are unsubstituted or carry at least one substituent as defined above.

Also preferred are pyrazole compounds of formulae (I.A1), (I.A2), (I.A3) or (I.A4), wherein W is hydroxycarbonyl.

Also preferred are pyrazole compounds of formulae (I.A1), (I.A2), (I.A3) or (I.A4), wherein $R^1$ and $R^2$ independently from each other are selected from $C_1$-$C_4$-alkyl, $C_3$-$C_6$-cycloalkyl and phenyl.

Also preferred are pyrazole compounds of formulae (I.A1), (I.A2), (I.A3) or (I.A4), wherein at least one of the radicals $R^1$ and $R^2$ is $C_1$-$C_4$-alkyl.

Particularly preferred are pyrazole compounds of formulae (I.A1), (I.A2), (I.A3) or (I.A4), wherein Y is selected from phenyl and naphthyl, wherein the phenyl and naphthyl moieties in the aforementioned radicals Y are unsubstituted or carry at least one substituent as defined above, W is hydroxycarbonyl, $R^1$ and $R^2$ independently from each other are selected from $C_1$-$C_4$-alkyl, $C_3$-$C_6$-cycloalkyl and phenyl and wherein at least one of the radicals $R^1$ and $R^2$ is $C_1$-$C_4$-alkyl.

A further embodiment of the present invention relates to compounds of formula (I), wherein the compounds of formula (I) are present in the form of the individual optical isomers, mixtures of the individual enantiomers or racemates, preferably in the form of the enantiomerically pure compounds.

A further embodiment of the present invention relates to compounds of formula (I), wherein the compounds of formula (I) are present in the form of the acid addition salts thereof with pharmacologically acceptable acids as well as optionally in the form of the solvates and/or hydrates.

Preparation

The compounds according to the invention may be obtained using methods of synthesis which are known to a person skilled in the art and described in the literature of organic synthesis. Preferably the compounds are obtained analogously to the methods of preparation explained more fully hereinafter, in particular as described in the experimental section.

Compounds of the invention wherein $L^3$ is —$NR^d$—C(O)— can be prepared according to scheme 1, Scheme 1

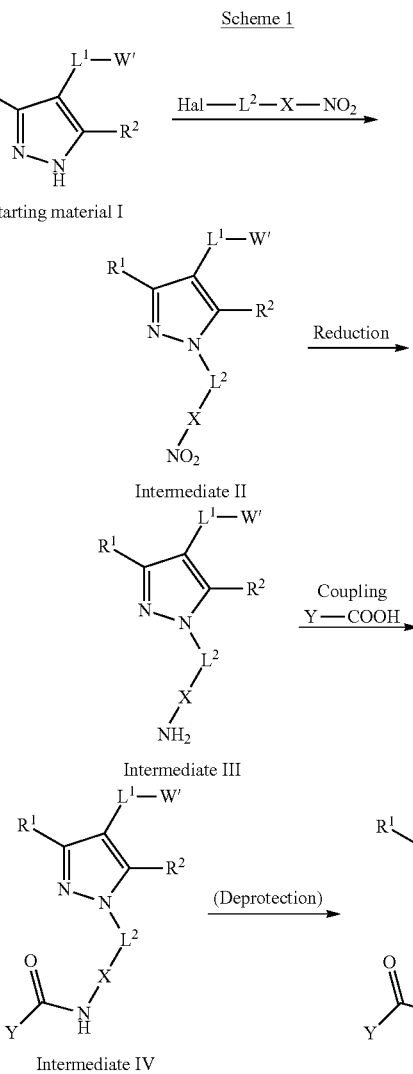

According to scheme 1 the compounds of the invention can be prepared employing as starting materials (1H-pyrazol-4- yl) derivatives, which are substituted with substituents $R^1$, $R^2$ and with a group $L^1$-W', wherein W' is a suitably protected derivative of W. These compounds can, in some cases, be obtained from commercial vendors or can be prepared according to literature procedures, for example WO 2007/141267. Suitable protecting groups can be selected from T. W. Greene, Protective Groups in Organic Synthesis, Wiley, $3^{rd}$ edition, 1999. Preferred protecting groups for W being hydroxycarbonyl are methyl, ethyl, tert-butyl. Intermediate II can be obtained by alkylation of starting material I with nitro substituted halogenides, e.g. 4-nitrobenzyl halogenides, more specifically 4-nitrobenzyl bromide, in the presence of a base. Suitable bases are inorganic bases such as carbonates, especially potassium carbonate. The reaction is preferably carried out in an organic solvent such as dimethylformamide, dimethylsulfoxid, acetonitrile, tetrahydrofuran, dichloromethane or a mixture of solvents. The reaction usually takes place within 1 to 48 hours. Preferred reaction temperatures are between 0° C. and the boiling point of the reaction mixture. When $R^1$ is different from $R^2$, the alkylation reaction may yield a mixture of regioisomers. The individual isomers may be separated by methods which are known to a person skilled in the art, for example, chromatography over silica gel employing a suitable solvent or solvent mixtures, or preparative reversed phase chromatography, employing a suitable gradient of solvents, or trituration or crystallization from suitable solvents or solvent mixtures.

Amine intermediate III can be prepared from intermediate II by reduction of the nitro group, for instance by hydrogenolysis in the presence of a catalyst, such as palladium on carbon. The reaction is preferably carried out in an inert organic solvent, such as methanol, ethanol, acetic acid, ethyl acetate or a mixture of solvents. The reaction usually takes place within 1 to 48 hours. Preferred reaction temperatures are between 0° C. and 50° C. Preferred reaction pressures are between atmospheric pressure and 100 bar. The reduction of the nitro group in intermediate II can also be carried out according to alternative methods described in J. March, Advanced Organic Chemistry, Wiley, $4^{th}$ edition, 1992, p. 1216-1217.

Amide intermediate IV can be prepared from amine intermediate III by coupling with a carboxylic acid Y—COOH in the presence of a coupling reagent, such as 2-(1H-benzotriazole-1-yl)-1,1,3,3-tetramethyluronium tetrafluoroborate (TBTU), and a base, such as diisopropylethylamine. The reaction is preferably carried out in an inert organic solvent, such as dimethylformamide, tetrahydrofuran, dichloromethane or a mixture of solvents. The reaction usually takes place within 1 to 48 hours. Preferred reaction temperatures are between 0° C. and 30° C. The coupling of a carboxylic acid to the amino group of intermediate III can also be carried out according to alternative methods described in J. March, Advanced Organic Chemistry, Wiley, $4^{th}$ edition, 1992, p. 419-421. Alternatively, instead of carboxylic acid Y—COOH and a coupling reagent, the corresponding acyl chloride Y—CO—Cl or anhydride Y—CO—O—CO—Y may be employed.

Compounds of formula (I) bearing a carbamate linker instead of an amide linker can be prepared from intermediate III by reaction with a chloroformate Y—O—CO—Cl in the presence of a base, such as diisopropylethylamine. The reaction is preferably carried out in an inert organic solvent, such as tetrahydrofuran, dichloromethane or a mixture of solvents. The reaction usually takes place within 1 to 48 hours. Preferred reaction temperatures are between 0° C. and 30° C.

Compounds of formula (I) bearing an urea linker instead of an amide linker can be prepared from intermediate III by reaction with an isocyanate Y—N=C=O. The reaction is preferably carried out in an inert organic solvent, such as tetrahydrofuran, dichloromethane or a mixture of solvents. The reaction usually takes place within 1 to 48 hours. Preferred reaction temperatures are between 0° C. and 30° C.

Compounds of formula (I) bearing a sulfonamide linker instead of an amide linker can be prepared from intermediate III by reaction with a sulfonyl chloride Y—$SO_2$Cl in the presence of a base, such as diisopropylethylamine or triethylamine. The reaction is preferably carried out in an inert organic solvent, such as tetrahydrofuran, dichloromethane, dimethylformamide or a mixture of solvents. The reaction usually takes place within 1 to 48 hours. Preferred reaction temperatures are between 0° C. and 30° C.

Compounds of formula (I) bearing a aminomethylene linker instead of an amide linker can be prepared from intermediate III by reaction with an aldehyde Y—CHO in the presence of a reducing agent, such as sodium triacetoxyborohydride or sodium cyanoborohydride. The reaction is preferably carried out in an inert organic solvent, such as tetrahydrofuran, dichloromethane, dimethylformamide or a mixture of solvents. The reaction usually takes place within 1 to 48 hours. Preferred reaction temperatures are between 0° C. and 30° C. The reductive amination can also be carried out according to alternative methods described in J. March, Advanced Organic Chemistry, Wiley, $4^{th}$ edition, 1992, p. 898-900.

Compounds of formula (I) can be obtained from intermediate IV by removal of the protecting group. In the case a hydroxycarbonyl group is protected by $CH_3$ or $C_2H_5$, this conversion can be carried out under aqueous conditions in the presence of an inorganic base, such as NaOH or LiOH. The reaction is preferably carried out in water or a mixture of water with $CH_3OH$, $C_2H_5OH$, tetrahydrofuran or dioxane. The reaction usually takes place within 1 to 48 hours. Preferred reaction temperatures are between 0° C. and the boiling point of the reaction mixture. The cleavage of the protecting group may also be carried out according to alternative methods described in J. March, Advanced Organic Chemistry, Wiley, $4^{th}$ edition, 1992, p. 378-383 or in T. W. Greene, Protective Groups in Organic Synthesis, Wiley, $3^{rd}$ edition, 1999.

Compounds of formula (I) bearing a (1H-pyrazol-4-yl)-acetic acid derivative moiety, can be prepared according to the route depicted in scheme 1, starting from the corresponding (1H-pyrazol-4-yl)-acetic acid derivative.

Compounds of formula (I) bearing a (1H-pyrazol-4-yl)-propionic acid derivative moiety, can be prepared according to the route depicted in scheme 1, starting from the corresponding (1H-pyrazol-4-yl)-propionic acid derivative.

Compounds (I) of the invention, wherein $L^3$ is —C(O)$NR^d$— can be prepared according to scheme 2.

Scheme 2

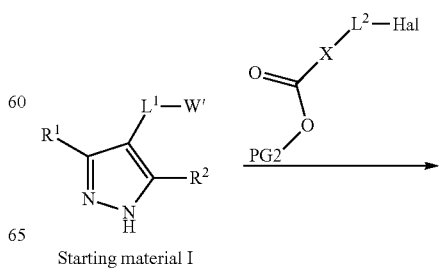

Starting material I

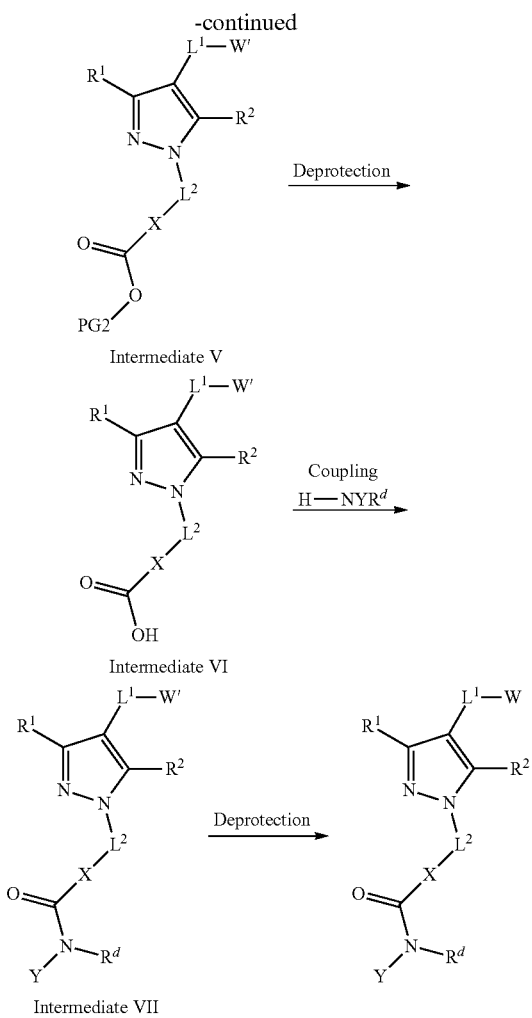

Intermediate V

Intermediate VI

Intermediate VII

Compounds (I) of the invention wherein $L^3$ is —C(O)NR$^d$— can be prepared employing as starting materials 1H-pyrazol-4-yl derivatives, which are substituted with R$^1$, R$^2$ and a moiety -L$^1$-W', wherein W' is a protected form of W.

Intermediate V can be obtained by alkylation of starting material I with a suitable halogenide, e.g. 4-bromomethyl-benzoic acid alkyl esters, in the presence of a base. Suitable bases are inorganic bases such as carbonates, especially potassium carbonate. The reaction is preferably carried out in an organic solvent such as dimethylformamide, dimethylsulfoxid, acetonitrile, tetrahydrofuran, dichloromethane or a mixture of solvents. The reaction usually takes place within 1 to 48 hours. Preferred reaction temperatures are between 0° C. and the boiling point of the reaction mixture. When R$^1$ is different from R$^2$, the alkylation reaction may yield a mixture of regioisomers. The individual isomers may be separated by methods which are known to a person skilled in the art, for example, chromatography over silica gel employing a suitable solvent or solvent mixtures, or preparative reversed phase chromatography, employing a suitable gradient of solvents, or trituration or crystallization from suitable solvents or solvent mixtures.

The protecting group used for W' and PG2 in scheme 2 should be "orthogonal" according to T. W. Greene, Protective Groups in Organic Synthesis, Wiley, 3$^{rd}$ edition, 1999, meaning that one protecting group can be removed under conditions where the other one remains intact (and vice versa).

Intermediate VI can be prepared from intermediate V by selective removal of the protecting group PG2. In the case of PG2=Me or Et, this conversion can be carried out under aqueous conditions in the presence of an inorganic base, such as NaOH or LiOH. The reaction is preferably carried out in water or a mixture of water with MeOH, EtOH, tetrahydrofuran or dioxane. The reaction usually takes place within 1 to 48 hours. Preferred reaction temperatures are between 0° C. and the boiling point of the reaction mixture. In the case of PG2=tert-butyl, the deprotection can be carried out under acidic conditions, for instance with trifluoroacetic acid. The reaction can be carried out in neat trifluoroacetic acid or in an inert solvent, such as dichloromethane. The reaction usually takes place within 1 to 48 hours. Preferred reaction temperatures are between 0° C. and 30° C. The cleavage of the protecting group PG2 may also be carried out according to alternative methods described in J. March, Advanced Organic Chemistry, Wiley, 4$^{th}$ edition, 1992, p. 378-383 or in T. W. Greene, Protective Groups in Organic Synthesis, Wiley, 3$^{rd}$ edition, 1999.

Amide intermediate VII can be prepared from carboxylic acid intermediate VI by coupling with an amine H—NYR$^d$ in the presence of a coupling reagent, such as TBTU, and a base, such as diisopropylethylamine. The reaction is preferably carried out in an inert organic solvent, such as dimethylformamide, tetrahydrofuran, dichloromethane or a mixture of solvents. The reaction usually takes place within 1 to 48 hours. Preferred reaction temperatures are between 0° C. and 30° C. The coupling of an amine with a carboxylic acid can also be carried out according to alternative methods described in J. March, Advanced Organic Chemistry, Wiley, 4$^{th}$ edition, 1992, p. 419-421.

Compounds of the invention can be obtained from intermediate VII by removal of the protecting group of W. The cleavage of the protecting group of W may also be carried out according to alternative methods described in J. March, Advanced Organic Chemistry, Wiley, 4$^{th}$ edition, 1992, p. 378-383 or in T. W. Greene, Protective Groups in Organic Synthesis, Wiley, 3$^{rd}$ edition, 1999.

Indications

The compounds of formula (I) according to the present invention are especially useful for manufacturing a medicament for the prevention and/or treatment of diseases wherein the activity of a CRTH2-receptor is involved.

One embodiment of the present invention relates to the manufacturing of a medicament for the prevention and/or treatment of a wide variety of inflammatory, infectious, and immunoregulatory disorders, respiratory or gastrointestinal diseases or complaints, inflammatory diseases of the joints and allergic diseases of the nasopharynx, eyes, and skin. Such disorders diseases and complaints include asthma and allergic diseases, eosinophilic diseases, chronic obstructive pulmonary disease, infection by pathogenic microbes (which, by definition, includes viruses), as well as autoimmune pathologies, such as the rheumatoid arthritis and atherosclerosis.

Preferred is the manufacturing of a medicament for the prevention and/or treatment of inflammatory or allergic diseases and conditions, including allergic or non-allergic rhinitis or sinusitis, chronic sinusitis or rhinitis, nasal polyposis, chronic rhinosinusitis, acute rhinosinusitis, asthma, pediatric asthma, allergic bronchitis, alveolitis, Farmer's disease, hyperreactive airways, allergic conjunctivitis, bronchitis or pneumonitis caused by infection, e.g. by bacteria or viruses or helminthes or fungi or protozoons or other pathogens, bronchiectasis, adult respiratory distress syndrome, bronchial and pulmonary edema, bronchitis or pneumonitis or interstitial pneumonitis caused by different origins, e.g. aspiration, inhalation of toxic gases, vapors, bronchitis or pneumonitis or interstitial pneumonitis caused by heart failure, X-rays, radiation, chemotherapy, bronchitis or pneumonitis or interstitial pneumonitis associated with collagenosis, e.g. lupus erythematodes, systemic scleroderma, lung fibrosis, idiopathic pulmonary lung fibrosis (IPF), interstitial lung diseases or interstitial pneumonitis of different origin, including asbestosis, silicosis, m. Boeck or sarcoidosis, granulomatosis, cystic fibrosis or mucoviscidosis, or α1-antitrypsin deficiency, eosinophilic cellulites (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, non-allergic asthma; exercise induced bronchoconstriction; chronic obstructive pulmonary disease (COPD), acute bronchitis, chronic bronchitis, cough, pulmonary emphysema; systemic anaphylaxis or hypersensitivity responses, drug allergies (e.g., to penicillin, cephalosporin), eosinophilia-myalgia syndrome due to the ingestion of contaminated tryptophane, insect sting allergies; autoimmune diseases, such as rheumatoid arthritis, psoriatic arthritis, multiple sclerosis, systemic lupus erythematosus, myasthenia gravis, immune thrombocytopenia (adult ITP, neonatal thrombocytopenia, pediatric ITP), immune hemolytic anemia (auto-immune and drug induced), Evans syndrome (platelet and red cell immune cytopaenias), $R^h$ disease of the newborn, Goodpasture's syndrome (anti-GBM disease), Celiac, autoimmune cardio-myopathy juvenile onset diabetes; glomerulonephritis, autoimmune thyroiditis, Behcet's disease; graft rejection (e.g., in transplantation), including allograft rejection or graftversus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); erythema nodosum; eosinophilic myositis, eosinophilic fasciitis, cancers with leukocyte infiltration of the skin or organs.

Method of Treatment

Accordingly, the compounds of formula (I) according to the present invention are useful in the prevention and/or treatment of a wide variety of inflammatory, infectious, and immunoregulatory disorders and diseases. Such disorders and diseases include but are not limited to asthma and allergic diseases, chronic obstructive pulmonary disease, infection by pathogenic microbes (which, by definition, includes viruses), autoimmune pathologies such as the rheumatoid arthritis and atherosclerosis.

As an example, an instant compound of formula (I) which inhibits one or more functions of a mammalian CRTH2 receptor (e.g., a human CRTH2 receptor) may be administered to inhibit (i.e., reduce or prevent) inflammation and bronchoconstriction. As a result, one or more inflammatory processes, such as leukocyte emigration, adhesion, chemotaxis, exocytosis (e.g., of enzymes, growth factors, histamine, cytotoxic proteins), inflammatory mediator release, survival or proliferation of CRTH2 expressing cells is inhibited. For example, activation or recruitment of Th2 cells, mast cells, basophils and eosinophilic to inflammatory sites (e.g., in asthma or allergic rhinitis) can be inhibited according to the present method.

In particular, the compounds of the following examples have activity in blocking the activation and migration of cells expressing the CRTH2 receptor using the appropriate CRTH2 agonists in the aforementioned assays.

Diseases or conditions of humans which can be treated with inhibitors of CRTH2 receptor function, include, but are not limited to inflammatory or allergic diseases and conditions, including allergic or non-allergic rhinitis or sinusitis, chronic sinusitis or rhinitis, nasal polyposis, chronic rhinosinusitis, acute rhinosinusitis, asthma, pediatric asthma, allergic bronchitis, alveolitis, Farmer's disease, hyperreactive airways, allergic conjunctivitis, bronchitis or pneumonitis caused by infection, e.g. by bacteria or viruses or helminthes or fungi or protozoons or other pathogens, bronchiectasis, adult respiratory distress syndrome, bronchial and pulmonary edema, bronchitis or pneumonitis or interstitial pneumonitis caused by different origins, e.g. aspiration, inhalation of toxic gases, vapors, bronchitis or pneumonitis or interstitial pneumonitis caused by heart failure, X-rays, radiation, chemotherapy, bronchitis or pneumonitis or interstitial pneumonitis associated with collagenosis, e.g. lupus erythematodes, systemic scleroderma, lung fibrosis, idiopathic pulmonary lung fibrosis (IPF), interstitial lung diseases or interstitial pneumonitis of different origin, including asbestosis, silicosis, m. Boeck or sarcoidosis, granulomatosis, cystic fibrosis or mucoviscidosis, or α1-antitrypsin deficiency, eosinophilic cellulites (e.g. Well's syndrome), eosinophilic pneumonias (e.g. Loeffler's syndrome, chronic eosinophilic pneumonia), eosinophilic fasciitis (e.g. Shulman's syndrome), delayed-type hypersensitivity, non-allergic asthma, exercise induced bronchoconstriction; chronic obstructive pulmonary disease (COPD), acute bronchitis, chronic bronchitis, cough, pulmonary emphysema; systemic anaphylaxis or hypersensitivity responses, drug allergies (e.g., to penicillin, cephalosporin), eosinophilia-myalgia syndrome due to the ingestion of contaminated tryptophane, insect sting allergies; autoimmune diseases, such as rheumatoid arthritis, psoriatic arthritis, multiple sclerosis, systemic lupus erythematosus, myasthenia gravis, immune thrombocytopenia (adult ITP, neonatal thrombocytopenia, pediatric ITP), immune hemolytic anemia (auto-immune and drug induced), Evans syndrome (platelet and red cell immune cytopaenias), Rh disease of the newborn, Goodpasture's syndrome (anti-GBM disease), Celiac, autoimmune cardio-myopathy juvenile onset diabetes; glomerulonephritis, autoimmune thyroiditis, Behcet's disease; graft rejection (e.g. in transplantation), including allograft rejection or graftversus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g. necrotizing, cutaneous, and hypersensitivity vasculitis); erythema nodosum; eosinophilic myositis, eosinophilic fasciitis; cancers with leukocyte infiltration of the skin or organs.

Combinations

The compounds of formula (I) according to the present invention may be used on their own or in combination with other compounds of formula (I). The compounds of formula (I) may optionally also be combined with other pharmacologically active substances.

Such pharmacologically active substances useable in the pharmaceutical composition containing compounds of formula (I) of the present invention may be selected from but are not limited to the classes consisting of β2-adrenoceptor-agonists (short and long-acting beta mimetics), anti-cholinergics (short and long-acting), anti-inflammatory steroids (oral and topical corticosteroids), dissociated-glucocorticoidmimetics, PDE3 inhibitors, PDE4 inhibitors, PDE7 inhibitors, LTD4 antagonists, EGFR inhibitors, PAF antagonists, Lipoxin A4 derivatives, FPRL1 modulators, LTB4-receptor (BLT1, BLT2) antagonists, histamine-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κB signaling pathway as for example IKK2 kinase inhibitors, iNOS inhibitors, MRP4 inhibitors, leukotriene biosynthesis inhibitors as for example 5-Lipoxygenase (5-LO) inhibitors, cPLA2 inhibitors, Leukotriene A4 hydrolase inhibitors or FLAP inhibitors, non-steroidal anti-inflammatory agents (NSAIDs), DP1-receptor modulators, thromboxane receptor antagonists, CCR1 antagonists, CCR2 antagonists, CCR3 antagonists, CCR4 antagonists, CCR5 antagonists, CCR6 antagonists, CCR7 antagonists, CCR8 antagonists, CCR9 antagonists, CCR10 antagonists, CXCR1 antagonists, CXCR2 antagonists, CXCR3 antagonists, CXCR4 antagonists, CXCR5 antagonists, CXCR6 antagonists, CX3CR1 antagonists, neurokinin (NK1, NK2) antagonists, sphingosine 1-phosphate receptor modulators, sphingosine 1-phosphate-lyase inhibitors, Adenosine receptor modulators as for example A2a-agonists, modulators of purinergic receptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-like receptor (TLR) modulators, HMG-CoA reductase inhibitors, VLA-4 antagonists, ICAM-1 inhibitors, SHIP agonists, GABAa receptor antagonist, ENaC-inhibitors, Melanocortin receptor (MC1R, MC2R, MC3R, MC4R, MC5R) modulators, CGRP antagonists, Endothelin antagonists, mucoregulators, immunotherapeutic agents, compounds against swelling of the airways, compounds against cough, CB2 agonists, retinoids, immunosuppressants, mast cell stabilizers, methylxanthine, opioid receptor agonists, laxatives, anti-foaming agents, antispasmodic agents, 5-HT4 agonists but also combinations of two or three active substances.

Preferred are combinations of two or three active substances, i.e.: CRTH2 antagonists according to the present invention with betamimetics, anticholinergics, corticosteroids, PDE4 inhibitors, LTD4 antagonists, EGFR inhibitors, CCR3 antagonists, CCR5 antagonists, CCR9 antagonists, 5-LO inhibitors, histamine receptor antagonists, SYK inhibitors and sulfonamides, or i.e.:

CRTH2 antagonists with betamimetics and corticosteroids, PDE4 inhibitors, CCR3 antagonists or LTD4 antagonists, CRTH2 antagonists with anticholinergics and betamimetics, corticosteroids, PDE4 inhibitors, CCR3 antagonists or LTD4 antagonists, CRTH2 antagonists with corticosteroids and PDE4 inhibitors, CCR3 antagonists or LTD4 antagonists CRTH2 antagonists with PDE4 inhibitors and CCR3 antagonists or LTD4 antagonists In the pharmaceutical compositions according to the present invention the CRTH2 antagonists of formula (I) may be contained in a form selected from tautomers, optical isomers, enantiomers, racemates, diastereomers, pharmacologically acceptable acid addition salts, solvates or hydrates, as far as such forms exist, depending on the individual compound. Pharmaceutical compositions comprising one or more, preferably one, compound 1 in form of a substantially pure enantiomer are preferred.

In the pharmaceutical compositions according to the present invention more than one CRTH2 antagonist of formula (I) and more than one further pharmacologically active compound can be present.

Pharmaceutical Forms

Suitable preparations for administering the compounds of formula (I) include for example tablets, capsules, suppositories, solutions and powders etc. The content of the pharmaceutically active compound(s) should be in the range from 0.05 to 90 wt.-%, preferably 0.1 to 50 wt.-% of the composition as a whole.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavor enhancer, e.g. a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilizers such as alkali metal salts of ethylenediaminetetraacetic acid, optionally using emulsifiers and/or dispersants, while if water is used as diluent, for example, organic solvents may optionally be used as solubilisers or dissolving aids, and the solutions may be transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include but are not limited to water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, preferably potato starch, gelatine and the like. Lubricants such as magnesium stearate, sodium laurylsulphate and talc may also be used to produce the tablets. In the case of aqueous suspensions the active substances may be combined with various flavor enhancers or colorings in addition to the above-mentioned excipients.

The compounds of formula (I) may also be administered as preparations or pharmaceutical formulations suitable for inhalation. Inhalable preparations include inhalable powders, propellant-containing metered-dose aerosols or propellant-free inhalable solutions. Within the scope of the present invention, the term propellant-free inhalable solutions also include concentrates or sterile inhalable solutions ready for use. The formulations which may be used within the scope of the present invention are described in more detail in the next part of the specification.

The inhalable powders which may be used according to the invention may contain (I) either on its own or in admixture with suitable physiologically acceptable excipients.

If the active substances (I) are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the present invention the excipients have a maximum average particle size of up to 250 µm, preferably between 10 and 150 µm, most preferably between 15 and 80 µm. It may sometimes seem appropriate to add finer excipient fractions with an average particle size of 1 to 9 µm to the excipient mentioned above. These finer excipients are also selected from the group of possible excipients listed hereinbefore. Finally, in order to prepare the inhalable powders according to the invention, micronised active substance 1, preferably with an average particle size of 0.5 to 10 µm, more preferably from 1 to 5 µm, is added to the excipient mixture. Processes for producing the inhalable powders according to the invention by grinding and micronising and finally mixing the ingredients together are known from the prior art.

The inhalable powders according to the invention may be administered using inhalers known from the prior art.

The inhalation aerosols containing propellant gas according to the invention may contain the compounds of formula (I) dissolved in the propellant gas or in dispersed form. The compounds of formula (I) may be contained in separate formulations or in a common formulation, in which the compounds of formula (I) are either both dissolved, both dispersed or in each case only one component is dissolved and the other is dispersed. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The abovementioned propellant gases may be used on their own or mixed together. Particularly preferred propellant gases are halogenated alkane derivatives selected from TG134a and TG227 and mixtures thereof.

The propellant-driven inhalation aerosols may also contain other ingredients such as co-solvents, stabilizers, surfactants, antioxidants, lubricants and pH adjusters. All these ingredients are known in the art.

The propellant-driven inhalation aerosols according to the invention mentioned above may be administered using inhalers known in the art (MDIs=metered dose inhalers).

Moreover, the active substances of formula (I) according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is preferably up to 70 percent by volume, more particularly up to 60 percent by volume and most preferably up to 30 percent by volume. The remainder of the volume is made up of water. The solutions or suspensions containing compounds of formula (I) are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavorings, antioxidants or complexing agents, such as citric acid or ascorbic acid, for example. According to the invention, it is particularly preferred to use hydrochloric acid to adjust the pH.

If desired, the addition of editic acid (EDTA) or one of the known salts thereof, sodium edetate, as stabilizer or complexing agent may be omitted in these formulations. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred.

Co-solvents and/or other excipients may be added to the propellant-free inhalable solutions. Preferred co-solvents are those which contain hydroxyl, groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilizers, complexing agents, antioxidants and/or preservatives which guarantee or prolong the shelf life of the finished pharmaceutical formulation, flavorings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

The dosage of the compounds according to the invention is naturally highly dependent on the method of administration and the complaint which is being treated. When administered by inhalation the compounds of formula (I) are characterized by a high potency even at doses in the μg range. The compounds of formula (I) may also be used effectively above the μg range. The dosage may then be in the gram range, for example.

In another aspect the present invention relates to the above-mentioned pharmaceutical formulations as such which are characterized in that they contain a compound of formula (I), particularly the above-mentioned pharmaceutical formulations which can be administered by inhalation.

The following examples of formulations illustrate the present invention without restricting its scope:

Examples of pharmaceutical formulations:

| A) | Tablets | per tablet |
|---|---|---|
| | active substance (I) | 100 mg |
| | lactose | 140 mg |
| | maize starch | 240 mg |
| | polyvinylpyrrolidone | 15 mg |
| | magnesium stearate | 5 mg |
| | Σ | 500 mg |

The finely ground active substance, lactose and some of the maize starch are mixed together. The mixture is screened, then moistened with a solution of polyvinylpyrrolidone in water, kneaded, wet granulated and dried. The granules, the remaining maize starch and the magnesium stearate are screened and mixed together. The mixture is pressed into tablets of suitable shape and size.

| B) | Tablets | per tablet |
|---|---|---|
| | active substance (I) | 80 mg |
| | lactose | 55 mg |
| | maize starch | 190 mg |
| | microcrystalline cellulose | 35 mg |
| | polyvinylpyrrolidone | 15 mg |
| | sodium carboxymethyl starch | 23 mg |
| | magnesium stearate | 2 mg |
| | Σ | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) | Ampoule solution | |
|---|---|---|
| | active substance (I) | 50 mg |
| | sodium chloride | 50 mg |
| | water for inj. | 5 ml |

The active substance is dissolved in water at its own pH or optionally at pH 5.5 to 6.5 and sodium chloride is added to make the solution isotonic. The resulting solution is filtered to remove pyrogens and the filtrate is transferred under aseptic conditions into ampoules which are then sterilized and heat-sealed. The ampoules contain 5 mg, 25 mg and 50 mg of active substance.

| D) | Metering aerosol | |
|---|---|---|
| | active substance (I) | 0.005 |
| | sorbitan trioleate | 0.1 |
| | monofluorotrichloromethane | ad 100 |
| | and TG134a:TG227 2:1 | |

The suspension is transferred into a conventional aerosol container with metering valve. Preferably 50 μl suspension are released on each actuation. The active substance may also be released in higher doses if desired (e.g. 0.02 wt.-%).

| E) | Solutions (in mg/100 ml) | |
|---|---|---|
| | active substance (I) | 333.3 mg |
| | benzalkonium chloride | 10.0 mg |
| | EDTA | 50.0 mg |
| | HCl (1N) | ad pH 2.4 |

This solution can be prepared in the usual way.

| F) | Inhalable powder | |
|---|---|---|
| | active substance (I) | 12 μg |
| | lactose monohydrate | ad 25 mg |

The inhalable powder is prepared in the usual way by mixing the individual ingredients.

The following examples serve to further illustrate the present invention without restricting its scope.

EXAMPLES

Synthesis Examples

Example 1.1

{3,5-Dimethyl-1-[4-(4-trifluoromethyl-benzoylamino)-benzyl]-1H-pyrazol-4-yl}-acetic acid

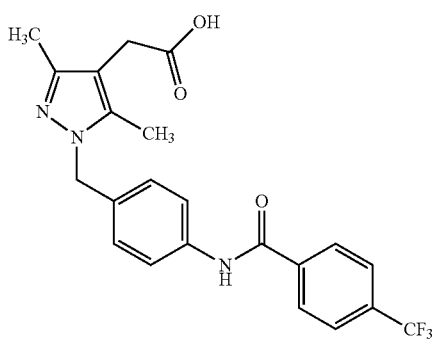 [SMILES: Cc1nn(Cc2ccc(NC(=O)c3ccc(C(F)(F)F)cc3)cc2)c(C)c1CC(=O)O]

Intermediate 1.1.1

(1-Benzyl-3,5-dimethyl-1H-pyrazol-4-yl)-acetic acid methyl ester (1-Benzyl-3,5-dimethyl-1H-pyrazol-4-yl)-acetic acid (1.00 g, 4.1 mmol) was dissolved in 3N methanolic HCl (7.5 mL) and stirred at room temperature for 18 h. The reaction mixture was neutralized with aqueous NaHCO$_3$ solution and extracted with dichloromethane. The organic layer was dried over MgSO$_4$ and concentrated under reduced pressure.

Yield: 963 mg
ESI mass spectrum: [M+H]$^+$=259
Retention time HPLC: 2.05 min (method A)

Intermediate 1.1.2 (Via Nitration)

[3,5-Dimethyl-1-(4-nitro-benzyl)-1H-pyrazol-4-yl]-acetic acid methyl ester

Under cooling, (1-benzyl-3,5-dimethyl-1H-pyrazol-4-yl)-acetic acid methyl ester (intermediate 1.1.1, 3.10 g, 12.0 mmol) was dissolved in conc. H$_2$SO$_4$ (7 mL). The mixture was cooled to −7° C. and HNO$_3$ (65%, 0.77 mL) was added dropwise under stirring, keeping the temperature below 0° C. The reaction mixture was allowed to come to room temperature and stirred for 20 min at room temperature. The reaction mixture was poured into ice water, extracted with dichloromethane and the organic layer was concentrated under reduced pressure. The resulting product is a mixture of regioisomers, with the 4-nitro isomer as the main product.

Yield: 3.90 g
ESI mass spectrum: [M+H]$^+$=304
Retention time HPLC: 2.08 min (method A)

Alternatively, intermediate 1.1.2 can be prepared according to the following procedure:

Intermediate 1.1.2 (Via Alkylation)

[3,5-Dimethyl-1-(4-nitro-benzyl)-1H-pyrazol-4-yl]-acetic acid methyl ester

To a solution of (3,5-dimethyl-1H-pyrazol-4-yl)-acetic acid methyl ester (3.90 g, 23 mmol, Enamine EN300-15247) and 4-nitrobenzyl bromide (4.60 g, 20.7 mmol) in acetonitrile was added K$_2$CO$_3$ (2.76 g, 19.9 mmol) and the mixture was stirred for one hour at room temperature. The reaction mixture was poured into water and extracted twice with ethyl acetate. The organic phase was dried over MgSO$_4$ and evaporated under reduced pressure.

Yield: 7.50 g (quantitative)
ESI mass spectrum: [M+H]$^+$=304

Intermediate 1.1.3

[1-(4-Amino-benzyl)-3,5-dimethyl-1H-pyrazol-4-yl]-acetic acid methyl ester

To a solution of [3,5-dimethyl-1-(4-nitro-benzyl)-1H-pyrazol-4-yl]-acetic acid methyl ester (intermediate 1.1.2, 3.90 g, 10.3 mmol) in methanol (10 mL) was added 10% palladium on charcoal (500 mg) and the mixture was hydrogenated. The catalyst was filtered off and the filtrate was concentrated under reduced pressure. The mixture was purified via preparative reversed phase HPLC (gradient of methanol in water+0.1% NH$_3$).

Yield: 1.18 g
ESI mass spectrum: [M+H]$^+$=274
Retention time HPLC: 2.13 min (method B)

Example 1.1

{3,5-Dimethyl-1-[4-(4-trifluoromethyl-benzoylamino)-benzyl]-1H-pyrazol-4-yl}-acetic acid Coupling: To a solution of [1-(4-amino-benzyl)-3,5-dimethyl-1H-pyrazol-4-yl]-acetic acid methyl ester (intermediate 1.1.3, 85 mg, 0.26 mmol) in dimethylformamide (1 mL) was added 4-(trifluoromethyl)benzoic acid (62 mg, 0.32 mmol), diisopropylethylamin (90 µL, 0.53 mmol) and TBTU (94 mg, 0.29 mmol). The reaction mixture was stirred for 18 h at room temperature. The reaction mixture was treated with aqueous K$_2$CO$_3$ solution (2 M, 0.15 mL) and filtered over Alox B, eluting with 10% methanol in dichloromethane. Saponification: The volatiles were removed under reduced pressure and the remaining residue was treated with aqueous NaOH solution (4 M, 0.2 mL). The mixture was purified via preparative reversed phase HPLC (gradient of methanol in water+0.1% NH$_3$).

Yield: 44 mg
ESI mass spectrum: [M+H]$^+$=432
Retention time HPLC: 1.94 min (method A)

The following examples were prepared according to the method described for example 1.1, employing the corresponding carboxylic acids as coupling partners.

| Example | Structure | m/z (ESI-MS) | Rt (HPLC) (method) |
| --- | --- | --- | --- |
| 1.2 | ![structure] | 412/414 (Cl) (M + H)⁺ | 1.86 min method A |
| 1.3 | ![structure] | 364 (M + H)⁺ | 1.63 min method A |
| 1.4 | ![structure] | 378 (M + H)⁺ | 1.75 min method A |
| 1.5 | ![structure] | 394 (M + H)⁺ | 1.68 min method A |
| 1.6 | ![structure] | 398/400 (Cl) (M + H)⁺ | 1.82 min method A |
| 1.7 | ![structure] | 414 (M + H)⁺ | 1.90 min method A |

-continued

| Example | Structure | m/z (ESI-MS) | Rt (HPLC) (method) |
|---|---|---|---|
| 1.8 | 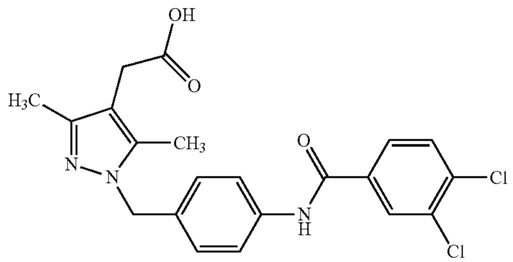 [SMILES: Cc1nn(Cc2ccc(NC(=O)c3ccc(Cl)c(Cl)c3)cc2)c(C)c1CC(=O)O] | 432/434/436 (Cl2) (M + H)+ | 1.99 min method A |
| 1.9 | 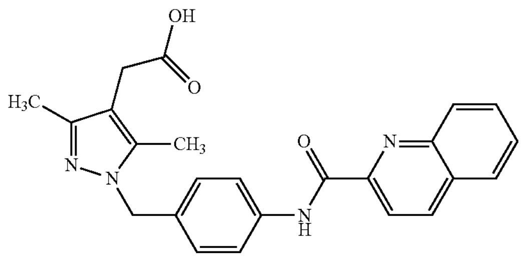 [SMILES: Cc1nn(Cc2ccc(NC(=O)c3ccc4ccccc4n3)cc2)c(C)c1CC(=O)O] | 415 (M + H)+ | 1.94 min method A |
| 1.10 | 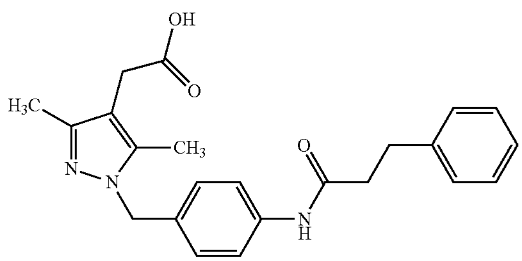 [SMILES: Cc1nn(Cc2ccc(NC(=O)CCc3ccccc3)cc2)c(C)c1CC(=O)O] | 392 (M + H)+ | 1.76 min method A |
| 1.11 | 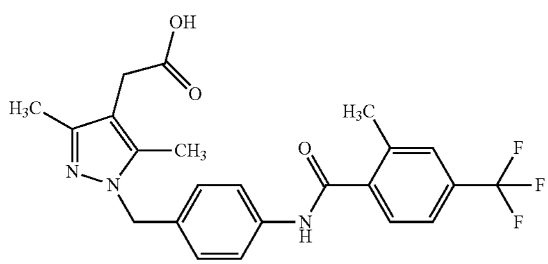 [SMILES: Cc1cc(C(F)(F)F)ccc1C(=O)Nc1ccc(Cn2nc(C)c(CC(=O)O)c2C)cc1] | 446 (M + H)+ | 2.12 min method A |
| 1.12 | 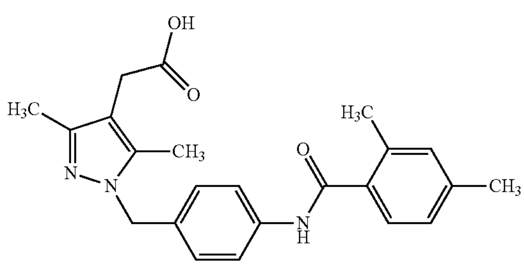 | 392 (M + H)+ | 1.78 min method B |
| 1.13 | 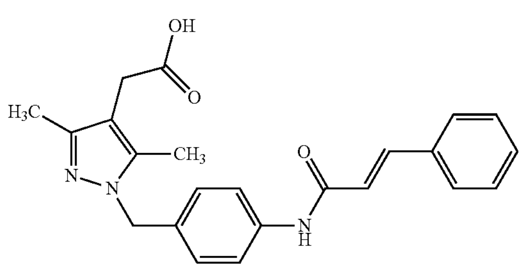 [SMILES: Cc1nn(Cc2ccc(NC(=O)/C=C/c3ccccc3)cc2)c(C)c1CC(=O)O] | 390 (M + H)+ | 1.84 min method A |

-continued

| Example | Structure | m/z (ESI-MS) | Rt (HPLC) (method) |
|---|---|---|---|
| 1.14 | 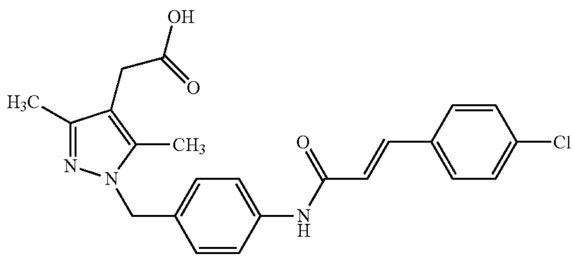 [SMILES: Cc1nn(Cc2ccc(NC(=O)/C=C/c3ccc(Cl)cc3)cc2)c(C)c1CC(=O)O] | 424/426 (Cl) (M + H)+ | 1.97 min method A |
| 1.15 | 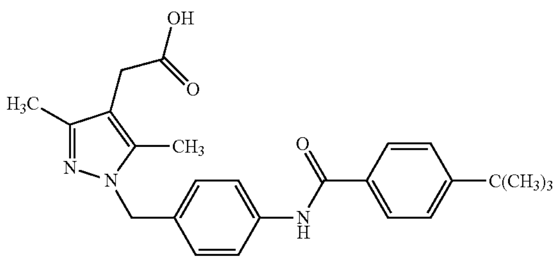 [SMILES: Cc1nn(Cc2ccc(NC(=O)c3ccc(C(C)(C)C)cc3)cc2)c(C)c1CC(=O)O] | 420 (M + H)+ | 2.04 min method B |
| 1.16 | 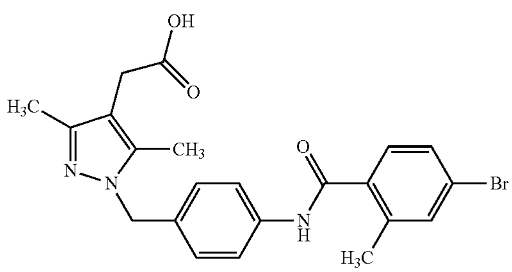 [SMILES: Cc1cc(Br)ccc1C(=O)Nc1ccc(Cn2nc(C)c(CC(=O)O)c2C)cc1] | 456/458 (Br) (M + H)+ | 1.87 min method B |
| 1.17 | 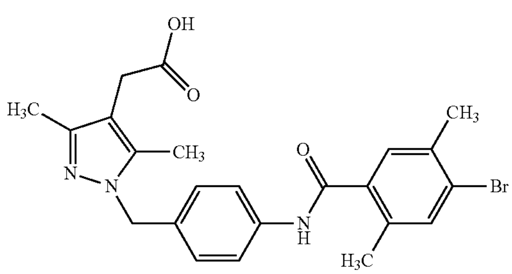 [SMILES: Cc1cc(C(=O)Nc2ccc(Cn3nc(C)c(CC(=O)O)c3C)cc2)c(C)cc1Br] | 470/472 (Br) (M + H)+ | 1.99 min method B |
| 1.18 | 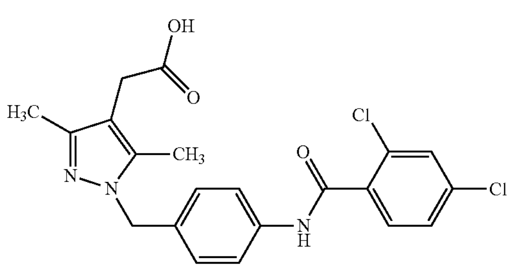 [SMILES: Cc1nn(Cc2ccc(NC(=O)c3ccc(Cl)cc3Cl)cc2)c(C)c1CC(=O)O] | 432/434/436 (Cl2) (M + H)+ | 1.80 min method B |
| 1.19 | 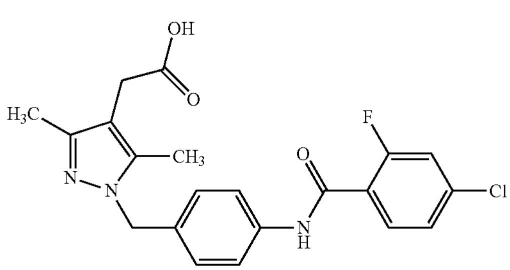 [SMILES: Cc1nn(Cc2ccc(NC(=O)c3ccc(Cl)cc3F)cc2)c(C)c1CC(=O)O] | 416/418 (Cl) (M + H)+ | 1.81 min method B |

-continued

| Example | Structure | m/z (ESI-MS) | Rt (HPLC) (method) |
|---------|-----------|--------------|---------------------|
| 1.20 | 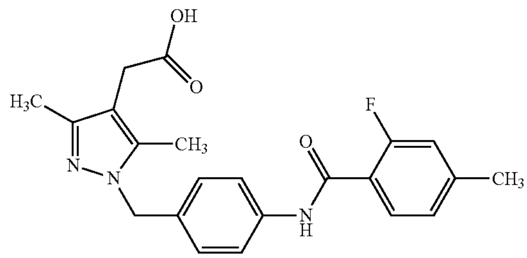 | 396 (M + H)+ | 1.78 min method B |
| 1.21 | 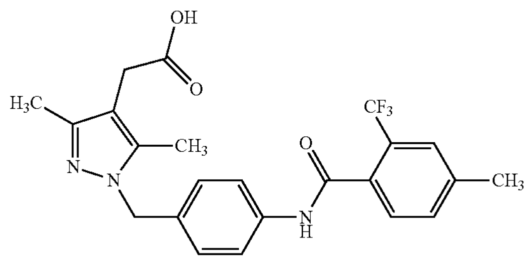 | 446 (M + H)+ | 1.79 min method B |
| 1.22 | 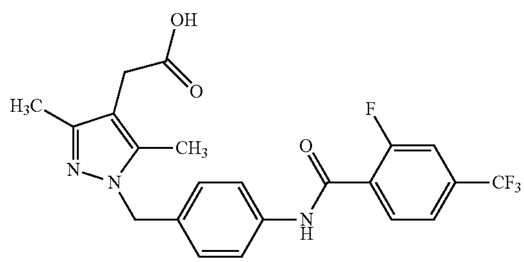 [SMILES: Cc1nn(Cc2ccc(NC(=O)c3ccc(C(F)(F)F)cc3F)cc2)c(C)c1CC(=O)O] | 450 (M + H)+ | 1.68 min method B |
| 1.23 | 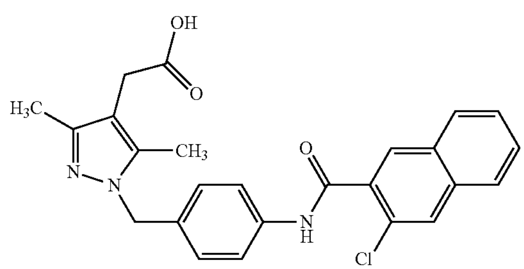 [SMILES: Cc1nn(Cc2ccc(NC(=O)c3cc4ccccc4cc3Cl)cc2)c(C)c1CC(=O)O] | 448/450 (Cl) (M + H)+ | 1.88 min method B |
| 1.24 | 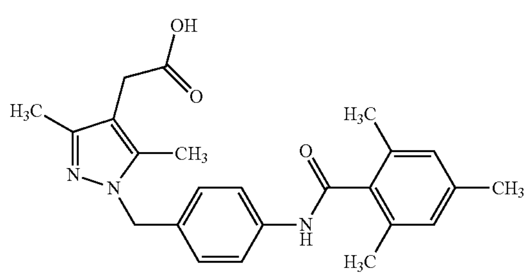 | 406 (M + H)+ | 1.80 min method B |
| 1.25 | 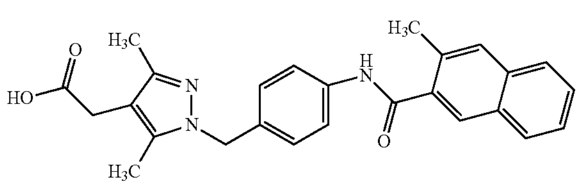 [SMILES: Cc1cc2ccccc2cc1C(=O)Nc1ccc(Cn2nc(C)c(CC(=O)O)c2C)cc1] | 428 | 0.99 min method J |

-continued

| Example | Structure | m/z (ESI-MS) | Rt (HPLC) (method) |
|---|---|---|---|
| 1.26 | 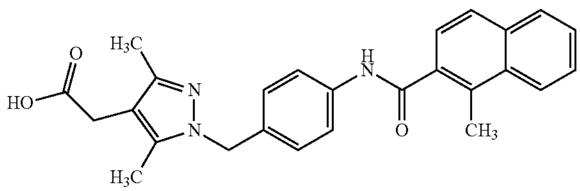 [SMILES: Cc1nn(Cc2ccc(NC(=O)c3ccc4ccccc4c3C)cc2)c(C)c1CC(=O)O] | 428 | 0.98 min method J |
| 1.27 | 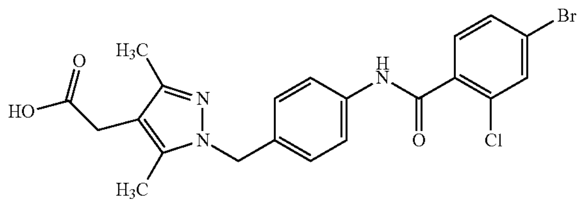 [SMILES: Cc1nn(Cc2ccc(NC(=O)c3ccc(Br)cc3Cl)cc2)c(C)c1CC(=O)O] | 476 | 0.97 min method J |
| 1.28 | 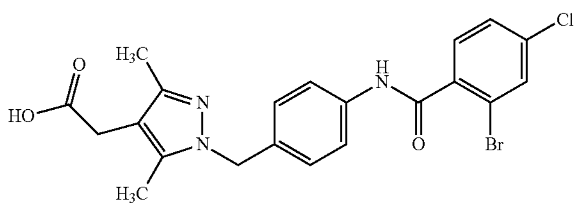 [SMILES: Cc1nn(Cc2ccc(NC(=O)c3ccc(Cl)cc3Br)cc2)c(C)c1CC(=O)O] | 476 | 0.95 min method J |
| 1.29 | 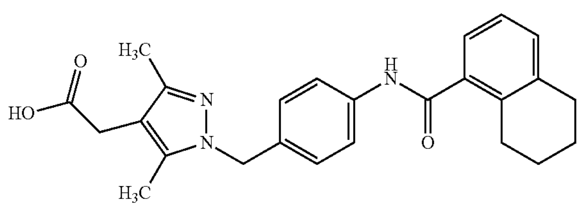 [SMILES: Cc1nn(Cc2ccc(NC(=O)c3cccc4c3CCCC4)cc2)c(C)c1CC(=O)O] | 418 | 0.98 min method J |
| 1.30 | 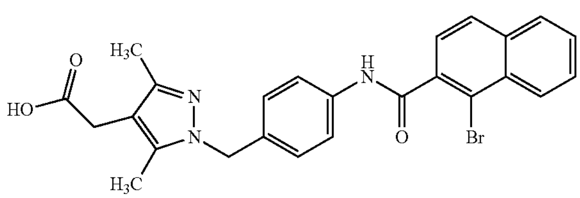 | 492 | 0.99 min method J |
| 1.31 | 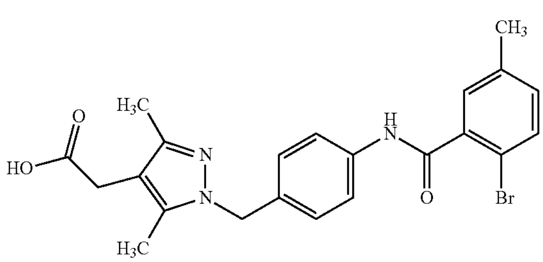 [SMILES: Cc1ccc(Br)c(C(=O)Nc2ccc(Cn3nc(C)c(CC(=O)O)c3C)cc2)c1] | 456 | 0.92 min method J |
| 1.32 | 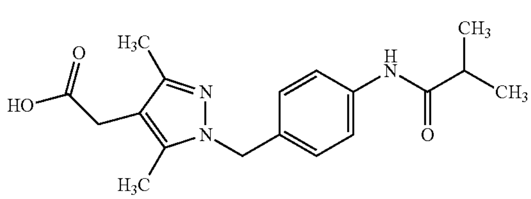 [SMILES: Cc1nn(Cc2ccc(NC(=O)C(C)C)cc2)c(C)c1CC(=O)O] | 330 | 0.73 min method J |

| Example | Structure | m/z (ESI-MS) | Rt (HPLC) (method) |
|---|---|---|---|
| 1.33 | 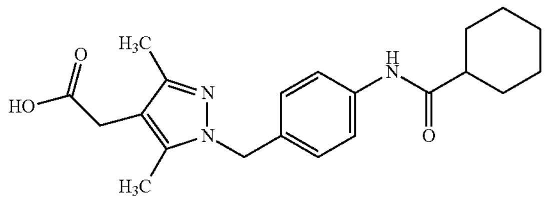 [SMILES: Cc1nn(Cc2ccc(NC(=O)C3CCCCC3)cc2)c(C)c1CC(=O)O] | 370 | 0.88 min method J |
| 1.34 | 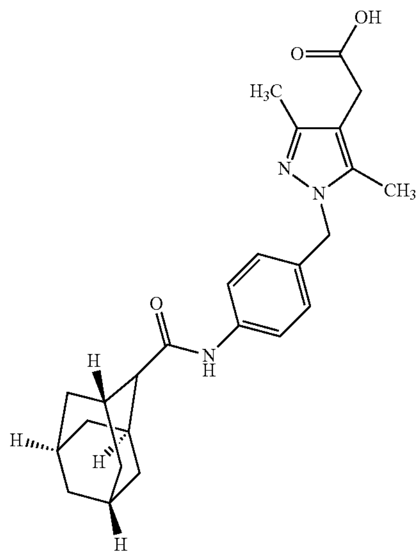 [SMILES: Cc1nn(Cc2ccc(NC(=O)C3[C@H]4C[C@@H]5C[C@@H](C[C@H]3C5)C4)cc2)c(C)c1CC(=O)O] | 422 | 1.44 min method D |
| 1.35 | 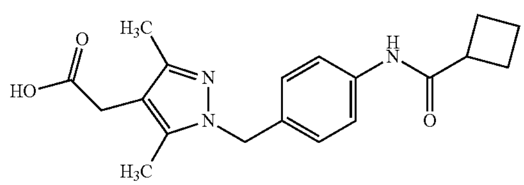 [SMILES: Cc1nn(Cc2ccc(NC(=O)C3CCC3)cc2)c(C)c1CC(=O)O] | 342 | 0.77 min method J |

Example 2.1

{3,5-Diethyl-1-[4-(4-trifluoromethyl-benzoylamino)-benzyl]-1H-pyrazol-4-yl}-acetic acid

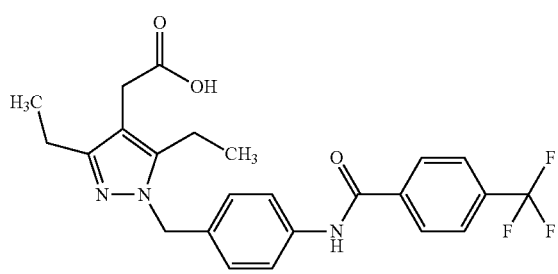 [SMILES: CCc1nn(Cc2ccc(NC(=O)c3ccc(C(F)(F)F)cc3)cc2)c(CC)c1CC(=O)O]

Intermediate 2.1.1

[3,5-Diethyl-1-(4-nitro-benzyl)-1H-pyrazol-4-yl]-acetic acid tert-butyl ester

[3,5-Diethyl-1-(4-nitro-benzyl)-1H-pyrazol-4-yl]-acetic acid tert-butyl ester was prepared according to the preparation of intermediate 1.1.2, using in the alkylation reaction (3,5-diethyl-1H-pyrazol-4-yl)-acetic acid tert-butyl ester (preparation according to WO2007/141267) instead of (3,5-dimethyl-1H-pyrazol-4-yl)-acetic acid methyl ester.

Intermediate 2.1.2

[1-(4-Amino-benzyl)-3,5-diethyl-1H-pyrazol-4-yl]-acetic acid tert-butyl ester

[1-(4-Amino-benzyl)-3,5-diethyl-1H-pyrazol-4-yl]-acetic acid tert-butyl ester was prepared according to the preparation of intermediate 1.1.3 using in the hydrogenation reaction intermediate 2.1.1 instead of intermediate 1.1.2.
ESI mass spectrum: [M+H]⁺=344
Retention time HPLC: 1.90 min (method A)

Example 2.1

{3,5-Diethyl-1-[4-(4-trifluoromethyl-benzoylamino)-benzyl]-1H-pyrazol-4-yl}-acetic acid Coupling: To a solution of [1-(4-amino-benzyl)-3,5-diethyl-1H-pyrazol-4-yl]-acetic acid tert-butyl ester (intermediate 2.1.2, 99 mg, 0.29 mmol) in dimethylformamide (1.5 mL) was added 4-(trifluoromethyl)benzoic acid (67 mg, 0.34 mmol), diisopropylethylamine (90 µL, 0.53 mmol) and TBTU (82 mg, 0.25 mmol). The reaction mixture was stirred for 18 h at room temperature. The reaction mixture was treated with aqueous $K_2CO_3$ solution (2 M, 0.15 mL) and filtered over Alox B, eluting with 10% methanol in dichloromethane. Cleavage of tert-butyl ester: The volatiles were removed under reduced pressure and the residue was treated with trifluoroacetic acid (2 mL). After 42 h, the mixture was concentrated under reduced pressure and purified via preparative reversed phase HPLC (gradient of methanol in water+0.1% $NH_3$).

Yield: 39 mg

ESI mass spectrum: $[M+H]^+$=460

Retention time HPLC: 2.03 min (method B)

The following examples were prepared according to the method described for example 2.1, employing the corresponding carboxylic acids as coupling partners.

| Example | Structure | m/z (ESI-MS) | Rt (HPLC) (method) |
|---|---|---|---|
| 2.2 | 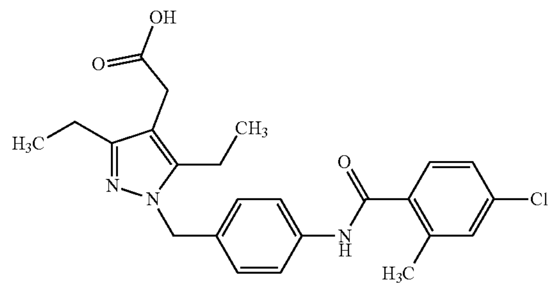 [SMILES: CCc1nn(Cc2ccc(NC(=O)c3ccc(Cl)cc3C)cc2)c(CC)c1CC(=O)O] | 440/442 (Cl) $(M + H)^+$ | 1.95 min method B |
| 2.3 | 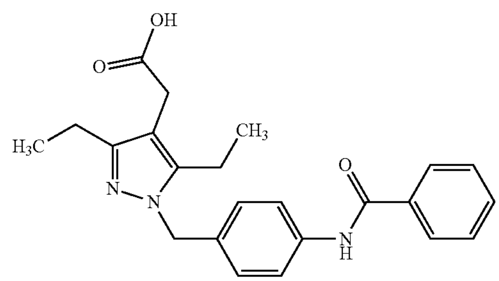 [SMILES: CCc1nn(Cc2ccc(NC(=O)c3ccccc3)cc2)c(CC)c1CC(=O)O] | 392 $(M + H)^+$ | 1.76 min method B |
| 2.4 | 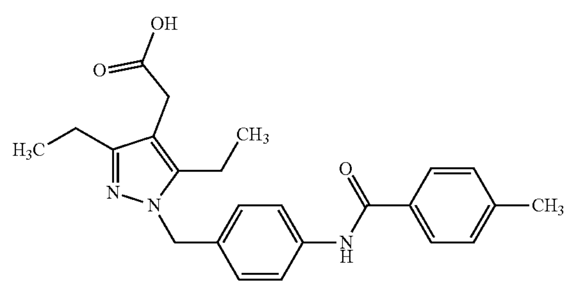 [SMILES: CCc1nn(Cc2ccc(NC(=O)c3ccc(C)cc3)cc2)c(CC)c1CC(=O)O] | 406 $(M + H)^+$ | 1.87 min method B |
| 2.5 | 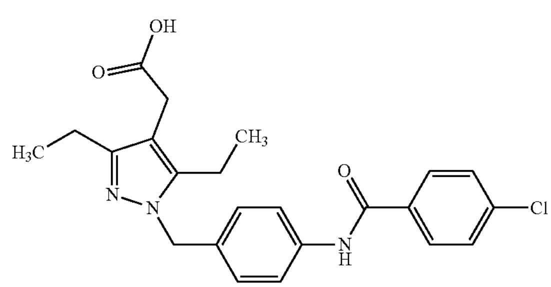 [SMILES: CCc1nn(Cc2ccc(NC(=O)c3ccc(Cl)cc3)cc2)c(CC)c1CC(=O)O] | 426/428 (Cl) $(M + H)^+$ | 1.92 min method B |

-continued

| Example | Structure | m/z (ESI-MS) | Rt (HPLC) (method) |
|---|---|---|---|
| 2.6 | 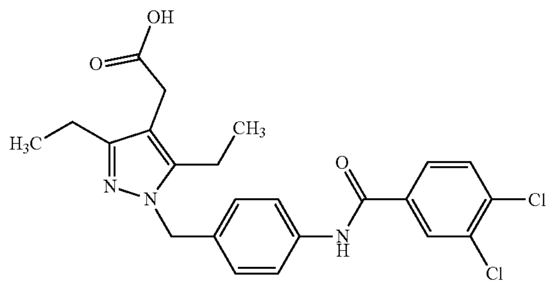 [SMILES: CCc1nn(Cc2ccc(NC(=O)c3ccc(Cl)c(Cl)c3)cc2)c(CC)c1CC(=O)O] | 460/462/464 (Cl2) (M + H)+ | 2.06 min method B |
| 2.14 | 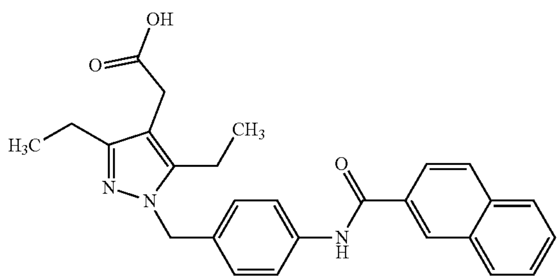 [SMILES: CCc1nn(Cc2ccc(NC(=O)c3ccc4ccccc4c3)cc2)c(CC)c1CC(=O)O] | 442 | 1.04 min method J |
| 2.15 | 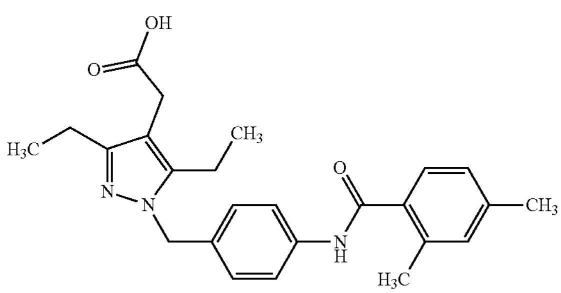 [SMILES: CCc1nn(Cc2ccc(NC(=O)c3ccc(C)cc3C)cc2)c(CC)c1CC(=O)O] | 420 | 0.99 min method J |
| 2.16 | 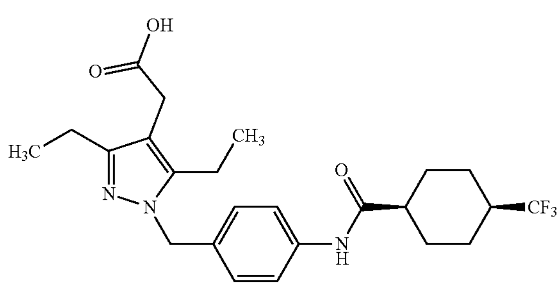 [SMILES: CCc1nn(Cc2ccc(NC(=O)[C@H]3CC[C@@H](C(F)(F)F)CC3)cc2)c(CC)c1CC(=O)O] | 466 | 1.3 min method J |
| 2.17 | 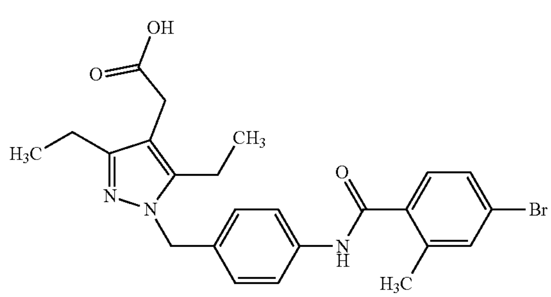 [SMILES: CCc1nn(Cc2ccc(NC(=O)c3ccc(Br)cc3C)cc2)c(CC)c1CC(=O)O] | 484 | 1.04 min method J |

-continued

| Example | Structure | m/z (ESI-MS) | Rt (HPLC) (method) |
|---|---|---|---|
| 2.18 | 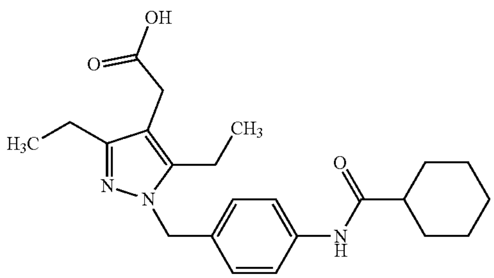 [SMILES: CCc1nn(Cc2ccc(NC(=O)C3CCCCC3)cc2)c(CC)c1CC(=O)O] | 398 | 0.95 min method J |
| 2.19 | 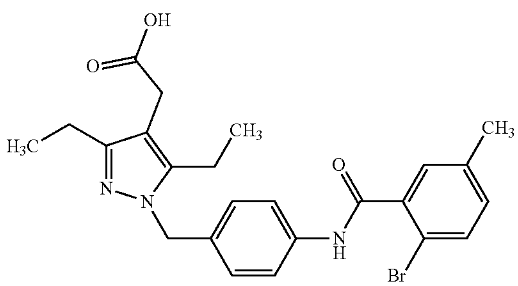 [SMILES: CCc1nn(Cc2ccc(NC(=O)c3cc(C)ccc3Br)cc2)c(CC)c1CC(=O)O] | 484 | 1.00 min method J |
| 2.20 | 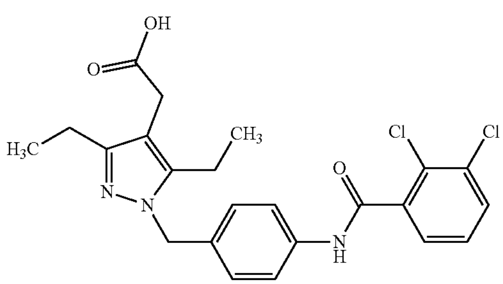 [SMILES: CCc1nn(Cc2ccc(NC(=O)c3cccc(Cl)c3Cl)cc2)c(CC)c1CC(=O)O] | 460 | 1.01 min method J |
| 2.21 | 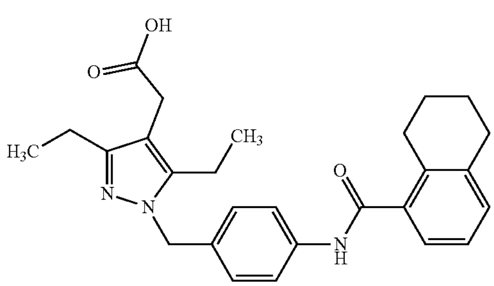 [SMILES: CCc1nn(Cc2ccc(NC(=O)c3cccc4c3CCCC4)cc2)c(CC)c1CC(=O)O] | 446 | 1.04 min method J |
| 2.22 | 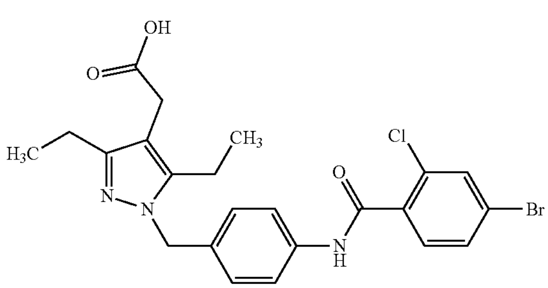 [SMILES: CCc1nn(Cc2ccc(NC(=O)c3ccc(Br)cc3Cl)cc2)c(CC)c1CC(=O)O] | 504 | 1.03 min method J |

-continued

| Example | Structure | m/z (ESI-MS) | Rt (HPLC) (method) |
|---|---|---|---|
| 2.23 | (structure) | 420 | 0.98 min method J |
| 2.24 | (structure) | 504 | 1.02 min method J |
| 2.25 | (structure) | 484 | 0.99 min method J |
| 2.26 | (structure) | 520 | 1.05 min method J |
| 2.27 | (structure) | 448 | 1.09 min method J |

-continued
| Example | Structure | m/z (ESI-MS) | Rt (HPLC) (method) |
|---|---|---|---|
| 2.28 | 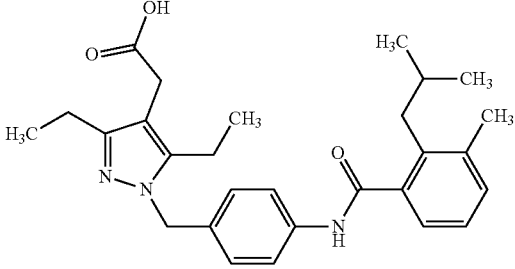 [SMILES: CCc1nn(Cc2ccc(NC(=O)c3cccc(C)c3CC(C)C)cc2)c(CC)c1CC(=O)O] | 462 | 1.12 min method J |
| 2.29 | 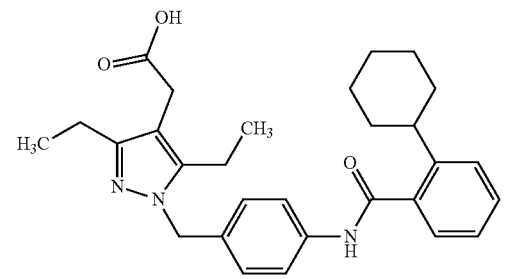 [SMILES: CCc1nn(Cc2ccc(NC(=O)c3ccccc3C3CCCCC3)cc2)c(CC)c1CC(=O)O] | 474 | 1.16 min method J |
| 2.30 | 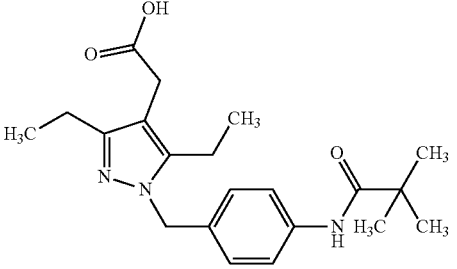 [SMILES: CCc1nn(Cc2ccc(NC(=O)C(C)(C)C)cc2)c(CC)c1CC(=O)O] | 372 | 0.88 min method J |
| 2.31 | 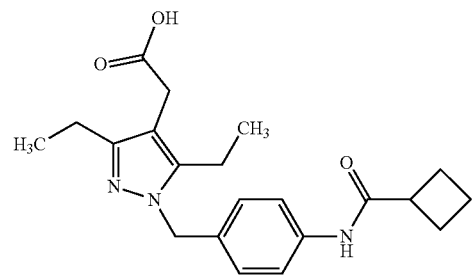 [SMILES: CCc1nn(Cc2ccc(NC(=O)C3CCC3)cc2)c(CC)c1CC(=O)O] | 370 | 0.85 min method J |
| 2.32 | 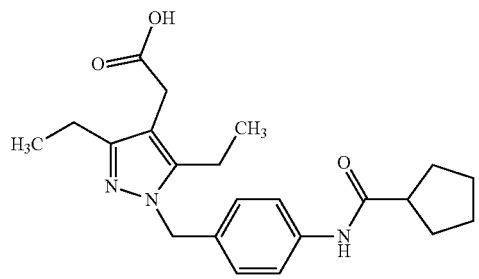 [SMILES: CCc1nn(Cc2ccc(NC(=O)C3CCCC3)cc2)c(CC)c1CC(=O)O] | 384 | 0.9 min method J |

-continued

| Example | Structure | m/z (ESI-MS) | Rt (HPLC) (method) |
|---|---|---|---|
| 2.33 | 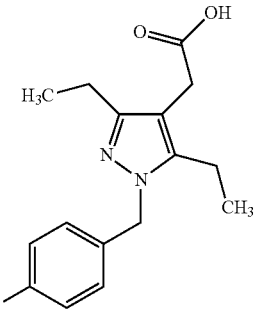 | 450 | 1.12 min method J |
| 2.34 | 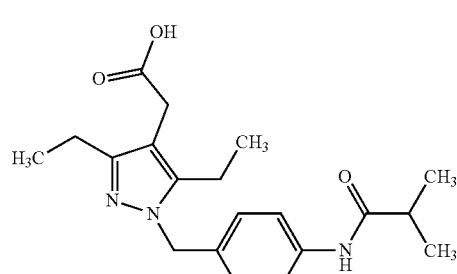 | 358 | 0.81 min method J |
| 2.35 | 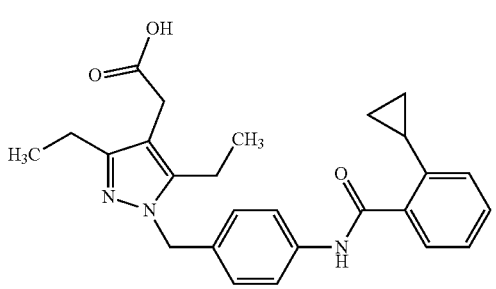 [SMILES: CCc1nn(Cc2ccc(NC(=O)c3ccccc3C3CC3)cc2)c(CC)c1CC(=O)O] | 432 | 0.99 min method J |

Example 2.7

{3-Cyclohexyl-5-methyl-1-[4-(4-trifluoromethyl-benzoylamino)-benzyl]-1H-pyrazol-4-yl}-acetic acid

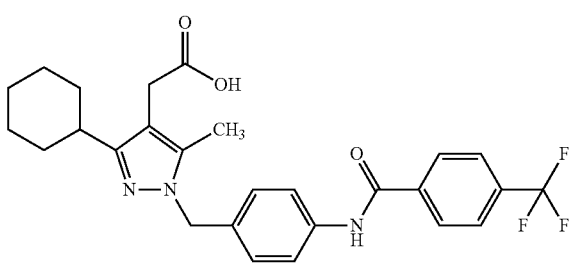 [SMILES: Cc1c(CC(=O)O)c(C2CCCCC2)nn1Cc1ccc(NC(=O)c2ccc(C(F)(F)F)cc2)cc1]

Intermediate 2.7.1

[3-Cyclohexyl-5-methyl-1-(4-nitro-benzyl)-1H-pyrazol-4-yl]-acetic acid tert-butyl ester

[3-Cyclohexyl-5-methyl-1-(4-nitro-benzyl)-1H-pyrazol-4-yl]-acetic acid tert-butyl ester was prepared according to the preparation of intermediate 1.1.2, using in the alkylation reaction (3-cyclohexyl-5-methyl-1H-pyrazol-4-yl)-acetic acid tert-butyl ester (preparation according to the preparation of (3,5-diethyl-1H-pyrazol-4-yl)-acetic acid tert-butyl ester, WO2007/141267, employing 1-cyclohexyl-butane-1,3-dione instead of heptane-3,5-dione) instead of (3,5-dimethyl-1H-pyrazol-4-yl)-acetic acid methyl ester.

Intermediate 2.7.2

[1-(4-Amino-benzyl)-3-cyclohexyl-5-methyl-1H-pyrazol-4-yl]-acetic acid tert-butyl ester

[1-(4-Amino-benzyl)-3-cyclohexyl-5-methyl-1H-pyrazol-4-yl]-acetic acid tert-butyl ester was prepared according to the preparation of intermediate 1.1.3 using in the hydrogenation reaction intermediate 2.7.1 instead of intermediate 1.1.2.

ESI mass spectrum: $[M+H]^+=384$

Example 2.7

{3-Cyclohexyl-5-methyl-1-[4-(4-trifluoromethyl-benzoylamino)-benzyl]-1H-pyrazol-4-yl}-acetic acid Example 2.7 was prepared according to the procedure for example 2.1, employing intermediate 2.7.2 instead of intermediate 2.1.2 in the coupling reaction.

Yield: 35 mg (30% of theory)
ESI mass spectrum: $[M+H]^+=500$
Retention time HPLC: 1.50 min (method D)

The following examples can be prepared in analogous fashion to example 2.7, employing in the alkylation step (3-methyl-5-phenyl-1H-pyrazol-4-yl)-acetic acid tert-butyl ester (preparation according to the preparation of (3,5-diethyl-1H-pyrazol-4-yl)-acetic acid tert-butyl ester, WO2007/141267, employing 1-phenyl-butane-1,3-dione instead of heptane-3,5-dione) instead of (3-cyclohexyl-5-methyl-1H-pyrazol-4-yl)-acetic acid tert-butyl ester and employing in the amide coupling the corresponding carboxylic acids as coupling partners.

| Example | Structure | m/z (ESI-MS) | Rt (HPLC) (method) |
|---------|-----------|--------------|--------------------|
| 2.8 | 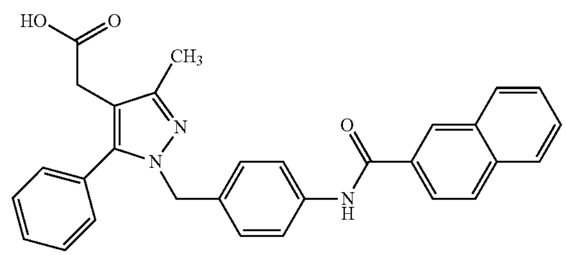 [SMILES: Cc1nn(Cc2ccc(NC(=O)c3ccc4ccccc4c3)cc2)c(-c2ccccc2)c1CC(=O)O] | 476 | 1.47 Method D |
| 2.9 | 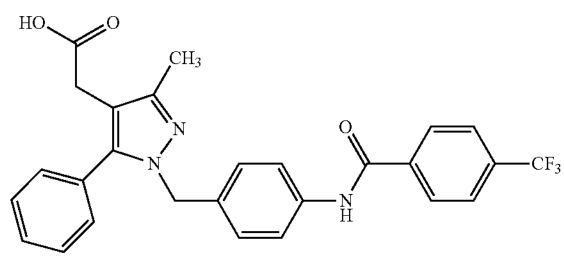 [SMILES: Cc1nn(Cc2ccc(NC(=O)c3ccc(C(F)(F)F)cc3)cc2)c(-c2ccccc2)c1CC(=O)O] | 494 | 1.47 Method D |
| 2.10 | 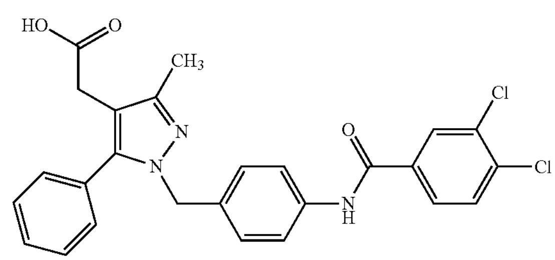 [SMILES: Cc1nn(Cc2ccc(NC(=O)c3ccc(Cl)c(Cl)c3)cc2)c(-c2ccccc2)c1CC(=O)O] | 494 | 1.53 min Method D |
| 2.11 | 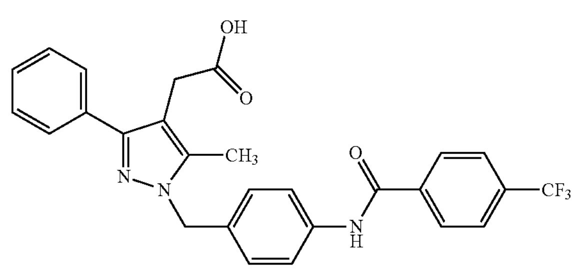 [SMILES: Cc1c(CC(=O)O)c(-c2ccccc2)nn1Cc1ccc(NC(=O)c2ccc(C(F)(F)F)cc2)cc1] | 494 | 1.46 min Method D |

| Example | Structure | m/z (ESI-MS) | Rt (HPLC) (method) |
|---------|-----------|--------------|--------------------|
| 2.12 | 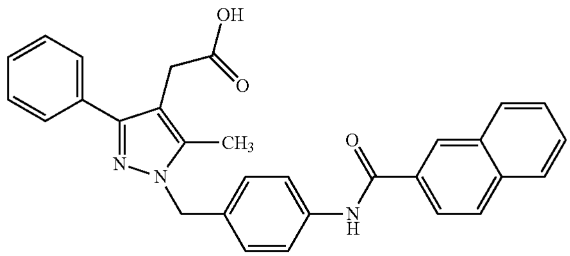 [SMILES: Cc1c(CC(=O)O)c(-c2ccccc2)nn1Cc1ccc(NC(=O)c2ccc3ccccc3c2)cc1] | 476 | 1.48 min Method D |
| 2.13 | 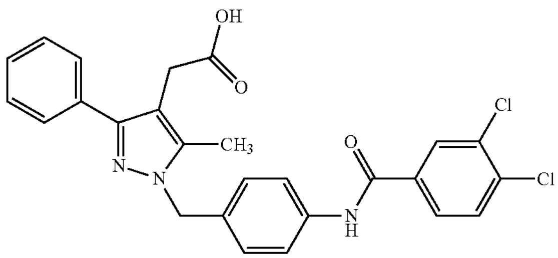 [SMILES: Cc1c(CC(=O)O)c(-c2ccccc2)nn1Cc1ccc(NC(=O)c2ccc(Cl)c(Cl)c2)cc1] | 494 | Method D |

Synthesis Examples 2.36-2.42

The following examples can be prepared in analogous fashion to example 2.7, employing in the alkylation step (3,5-diisopropyl-1H-pyrazol-4-yl)-acetic acid tert-butyl ester (preparation according to the preparation of (3,5-diethyl-1H-pyrazol-4-yl)-acetic acid tert-butyl ester, WO2007/141267, employing 2,6-dimethyl-heptane-3,5-dione instead of heptane-3,5-dione) instead of (3-cyclohexyl-5-methyl-1H-pyrazol-4-yl)-acetic acid tert-butyl ester and employing in the amide coupling the corresponding carboxylic acids as coupling partners.

| Example | Structure | m/z (ESI-MS) | Rt (HPLC) (method) |
|---------|-----------|--------------|--------------------|
| 2.36 | 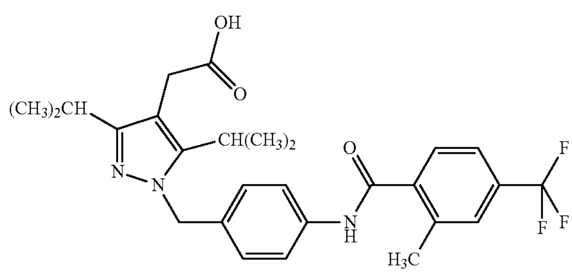 | 502 | 1.13 min Method J |
| 2.37 | 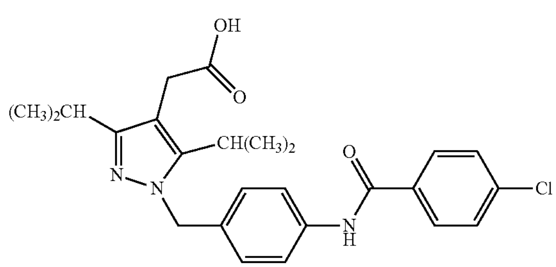 | 454 | 1.06 min Method J |

-continued

| Example | Structure | m/z (ESI-MS) | Rt (HPLC) (method) |
|---|---|---|---|
| 2.38 | 3,5-diisopropyl-1-[4-(4-chloro-2-methylbenzoylamino)benzyl]-1H-pyrazol-4-yl acetic acid | 468 | 1.09 min Method J |
| 2.39 | 3,5-diisopropyl-1-[4-(benzoylamino)benzyl]-1H-pyrazol-4-yl acetic acid | 420 | 0.97 min Method J |
| 2.40 | 3,5-diisopropyl-1-[4-(3,4-dichlorobenzoylamino)benzyl]-1H-pyrazol-4-yl acetic acid | 488 | 1.15 min Method J |
| 2.41 | 3,5-diisopropyl-1-[4-(4-trifluoromethylbenzoylamino)benzyl]-1H-pyrazol-4-yl acetic acid | 488 | 1.11 min Method J |
| 2.42 | 3,5-diisopropyl-1-[4-(naphthalene-2-carbonylamino)benzyl]-1H-pyrazol-4-yl acetic acid | 470 | 1.1 min Method J |

Synthesis Examples 2.43-2.45

The following examples can be prepared in analogous fashion to example 2.7, employing in the alkylation step (3,5-diphenyl-1H-pyrazol-4-yl)-acetic acid ethyl ester (preparation according to the preparation of (3,5-diethyl-1H-pyrazol-4-yl)-acetic acid tert-butyl ester, WO2007/141267, employing 2,6-diphenyl-heptane-3,5-dione instead of heptane-3,5-dione and bromoacetic acid ethyl ester instead of bromoacetic acid tert-butyl ester) instead of (3-cyclohexyl-5-methyl-1H-pyrazol-4-yl)-acetic acid tert-butyl ester and employing in the amide coupling the corresponding carboxylic acids as coupling partners.

Synthesis Examples 2.46-2.51

The following examples can be prepared in analogous fashion to example 2.7, employing in the alkylation step (3-cyclopropyl-5-ethyl-1H-pyrazol-4-yl)-acetic acid ethyl ester (preparation according to the preparation of (3,5-diethyl-1H-pyrazol-4-yl)-acetic acid tert-butyl ester, WO2007/141267, employing 2-cyclopropyl-6-ethyl-3,5-dione instead of heptane-3,5-dione) instead of (3-cyclohexyl-5-methyl-1H-pyrazol-4-yl)-acetic acid tert-butyl ester and employing in the amide coupling the corresponding carboxylic acids as coupling partners. Each example is a single regioisomer; the required intermediates [1-(4-amino-benzyl)-3-cyclopropyl-5-ethyl-1H-pyrazol-4-yl]-acetic acid and [1-(4-amino-benzyl)-5-cyclopropyl-3-ethyl-1H-pyrazol-4-yl]-acetic acid are obtained in a single reaction and are separable by MPLC.-

| Example | Structure | m/z (ESI-MS) | Rt (HPLC) (method) |
|---|---|---|---|
| 2.43 | 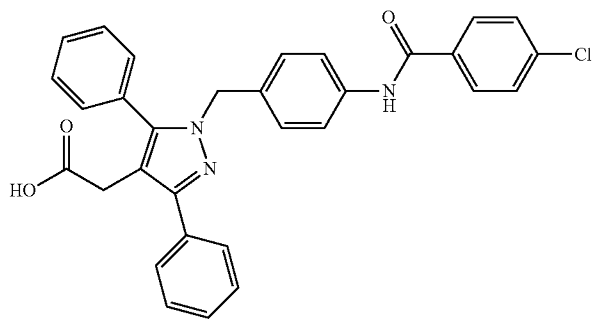 [SMILES: O=C(O)Cc1c(-c2ccccc2)nn(Cc2ccc(NC(=O)c3ccc(Cl)cc3)cc2)c1-c1ccccc1] | 522 | 1.27 min Method J |
| 2.44 | 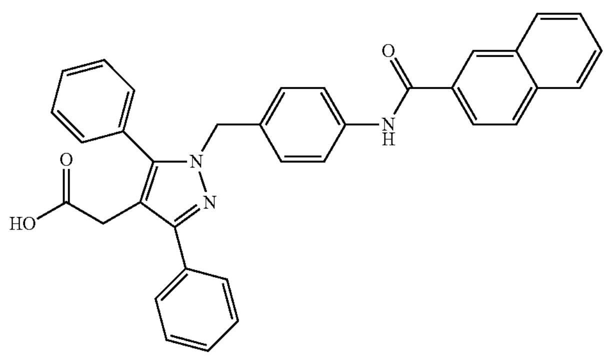 [SMILES: O=C(O)Cc1c(-c2ccccc2)nn(Cc2ccc(NC(=O)c3ccc4ccccc4c3)cc2)c1-c1ccccc1] | 538 | 1.31 min Method J |
| 2.45 | 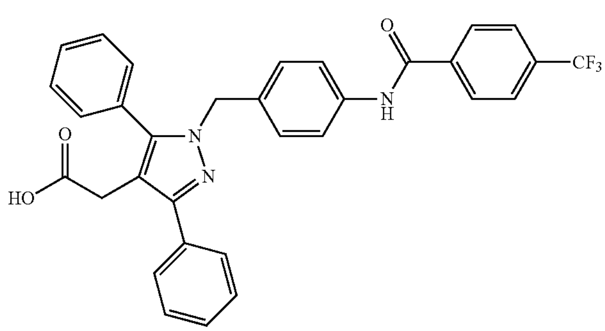 [SMILES: O=C(O)Cc1c(-c2ccccc2)nn(Cc2ccc(NC(=O)c3ccc(C(F)(F)F)cc3)cc2)c1-c1ccccc1] | 556 | 1.31 min Method J |

| Example | Structure | m/z (ESI-MS) | Rt (HPLC) (method) |
|---|---|---|---|
| 2.46 | 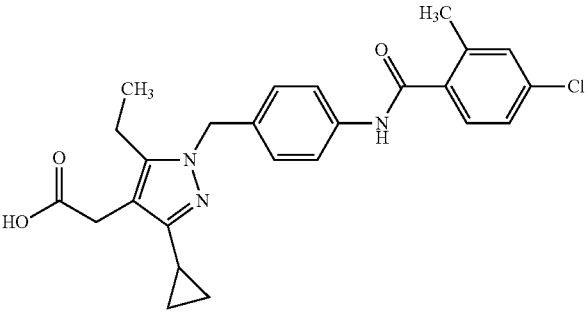 [SMILES: CCc1c(CC(=O)O)c(C2CC2)nn1Cc1ccc(NC(=O)c2ccc(Cl)cc2C)cc1] | 452 | 1.06 min Method J |
| 2.47 | 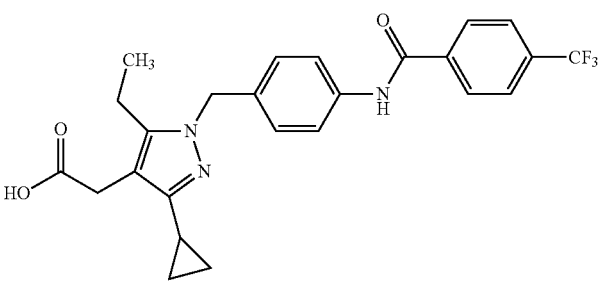 [SMILES: CCc1c(CC(=O)O)c(C2CC2)nn1Cc1ccc(NC(=O)c2ccc(C(F)(F)F)cc2)cc1] | 472 | 1.08 min Method J |
| 2.48 | 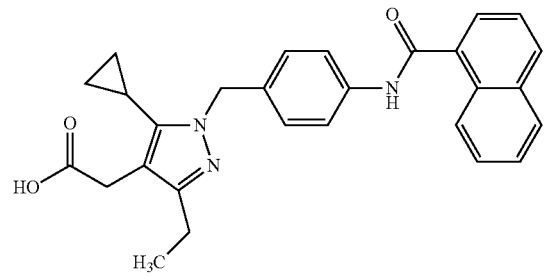 [SMILES: CCc1nn(Cc2ccc(NC(=O)c3cccc4ccccc34)cc2)c(C2CC2)c1CC(=O)O] | 454 | 1.03 min Method J |
| 2.49 | 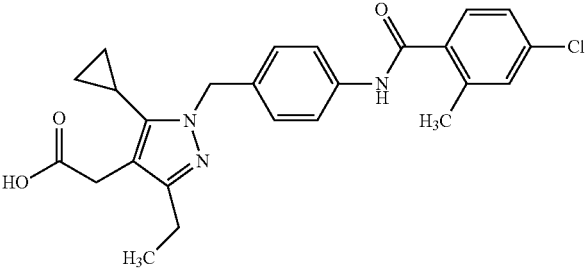 [SMILES: CCc1nn(Cc2ccc(NC(=O)c3ccc(Cl)cc3C)cc2)c(C2CC2)c1CC(=O)O] | 452 | 1.05 min Method J |
| 2.50 | 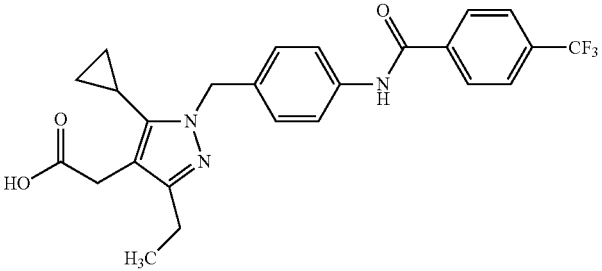 [SMILES: CCc1nn(Cc2ccc(NC(=O)c3ccc(C(F)(F)F)cc3)cc2)c(C2CC2)c1CC(=O)O] | 472 | 1.08 min Method J |

| Example | Structure | m/z (ESI-MS) | Rt (HPLC) (method) |
|---------|-----------|--------------|---------------------|
| 2.51 | 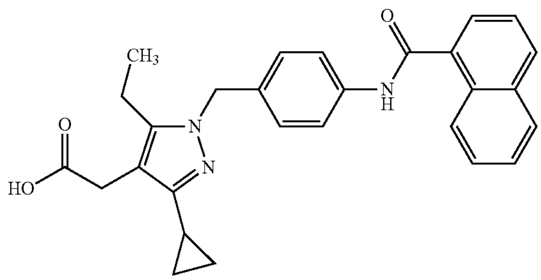 [SMILES: CCc1c(CC(=O)O)c(C2CC2)nn1Cc1ccc(NC(=O)c2cccc3ccccc23)cc1] | 454 | 1.04 min Method J |

Synthesis Examples 2.52-2.53

The following examples can be prepared in analogous fashion to example 2.7, employing in the alkylation step (3-methyl-5-ethyl-1H-pyrazol-4-yl)-acetic acid tert-butyl ester (preparation according to the preparation of (3,5-diethyl-1H-pyrazol-4-yl)-acetic acid tert-butyl ester, WO2007/141267, employing hexane-2,4-dione instead of heptane-3,5-dione) instead of (3-cyclohexyl-5-methyl-1H-pyrazol-4-yl)-acetic acid tert-butyl ester and employing in the amide coupling the corresponding carboxylic acids as coupling partners. Each example is a single regioisomer which is obtained.

| Example | Structure | m/z (ESI-MS) | Rt (HPLC) (method) |
|---------|-----------|--------------|---------------------|
| 2.52 | 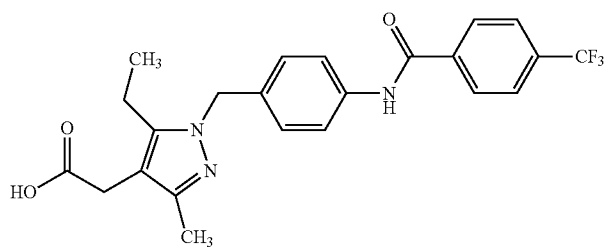 [SMILES: CCc1c(CC(=O)O)c(C)nn1Cc1ccc(NC(=O)c2ccc(C(F)(F)F)cc2)cc1] | 446 | 1.01 min Method J |
| 2.53 | 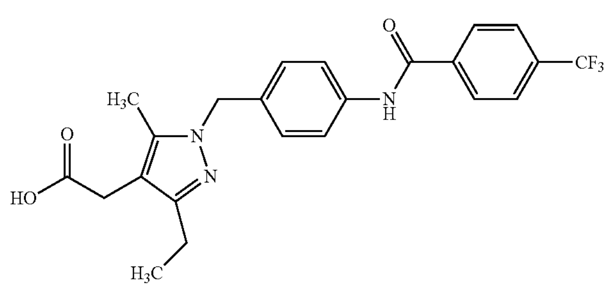 [SMILES: CCc1nn(Cc2ccc(NC(=O)c3ccc(C(F)(F)F)cc3)cc2)c(C)c1CC(=O)O] | 446 | 1.01 min Method J |

Synthesis Examples 2.55-2.59

The following examples can be prepared in analogous fashion to example 1.1, employing in the reduction step [5-methyl-1-(4-nitro-benzyl)-1H-pyrazol-4-yl]-acetic acid tert-butyl ester or in the case of example 2.59 [5-ethyl-1-(4-nitro-benzyl)-1H-pyrazol-4-yl]-acetic acid tert-butyl ester (preparation according to WO2008/138876) instead of [3,5-dimethyl-1-(nitrobenzyl)-1H-pyrazol-4-yl-acetic acid methyl ester and employing in the amide coupling the corresponding carboxylic acids as coupling partners. Each example except for example 2.59 is a single regioisomer; the required intermediates [1-(4-amino-benzyl)-3-methyl-1H-pyrazol-4-yl]-acetic acid tert-butyl ester and [1-(4-amino-benzyl)-5-methyl-1H-pyrazol-4-yl]-acetic acid tert-butyl ester are obtained in a single reaction and are separable by MPLC.

| Example | Structure | m/z (ESI-MS) | Rt (HPLC) (method) |
|---|---|---|---|
| 2.55 | 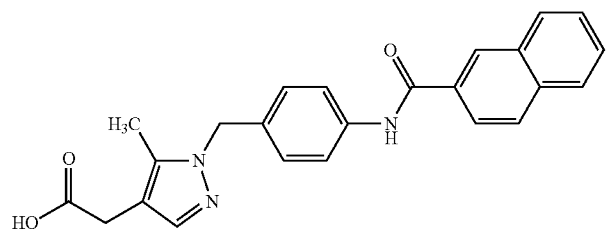 [SMILES: Cc1c(CC(=O)O)cnn1Cc1ccc(NC(=O)c2ccc3ccccc3c2)cc1] | 400 | 1.01 min Method J |
| 2.56 | 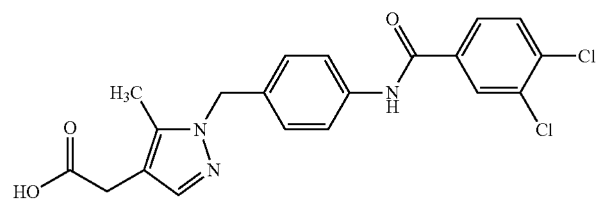 [SMILES: Cc1c(CC(=O)O)cnn1Cc1ccc(NC(=O)c2ccc(Cl)c(Cl)c2)cc1] | 418 | 1.05 min Method J |
| 2.57 | 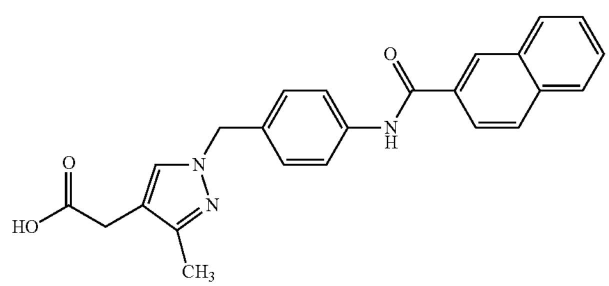 [SMILES: Cc1nn(Cc2ccc(NC(=O)c3ccc4ccccc4c3)cc2)cc1CC(=O)O] | 400 | 1.00 min Method J |
| 2.58 | 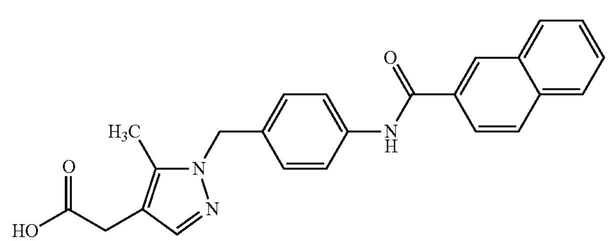 [SMILES: Cc1c(CC(=O)O)cnn1Cc1ccc(NC(=O)c2ccc3ccccc3c2)cc1] | 400 | 1.01 min Method J |
| 2.59 | 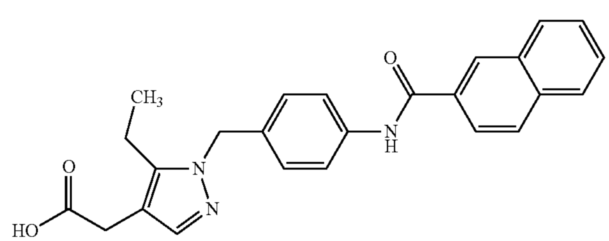 [SMILES: CCc1c(CC(=O)O)cnn1Cc1ccc(NC(=O)c2ccc3ccccc3c2)cc1] | 414 | 1.05 min Method J |

Synthesis Example 2.60

The following example can be prepared in analogous fashion to example 2.7, employing in the alkylation step (3-Methoxy-5-methyl-1H-pyrazol-4-yl)-acetic acid methyl ester (preparation according to the preparation of (3,5-diethyl-1H-pyrazol-4-yl)-acetic acid tert-butyl ester, WO2007/141267, employing 3-oxo-butyric acid methyl ester instead of heptane-3,5-dione) instead of (3-cyclohexyl-5-methyl-1H-pyrazol-4-yl)-acetic acid tert-butyl ester and employing in the amide coupling the corresponding carboxylic acids as coupling partners. The example was obtained a mixture of regioisomers.

mixture was stirred for 18 h at room temperature. The reaction mixture was filtered over Alox B, eluting with 10% methanol in dichloromethane. Saponification: After removing the volatiles under reduced pressure, the remaining residue was dissolved, in methanol (1 mL) and treated with aqueous NaOH solution (4 M, 0.2 mL). The mixture was neutralized with aqueous HCl and purified via preparative reversed phase HPLC (gradient of methanol in water+0.1% $NH_3$).

Yield: 34 mg
ESI mass spectrum: $[M+H]^+$=394
Retention time HPLC: 1.84 min (method B)

| Example | Structure | m/z (ESI-MS) | Rt (HPLC) (method) |
|---|---|---|---|
| 2.60 | 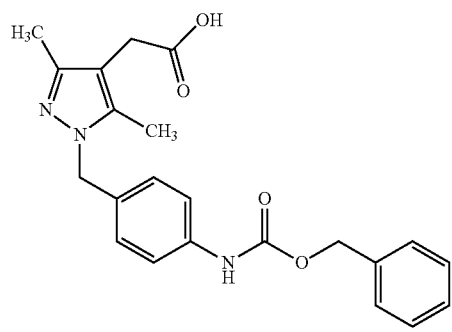 [SMILES: Cc1nn(Cc2ccc(NC(=O)OCc3ccccc3)cc2)c(C)c1CC(=O)O] | 430 | 1.06 min Method J |

Example 3.1

[1-(4-Benzyloxycarbonylamino-benzyl)-3,5-dimethyl-1H-pyrazol-4-yl]-acetic acid

Example 3.2

3-[1-(4-Benzyloxycarbonylamino-benzyl)-3,5-dimethyl-1H-pyrazol-4-yl]-propionic acid

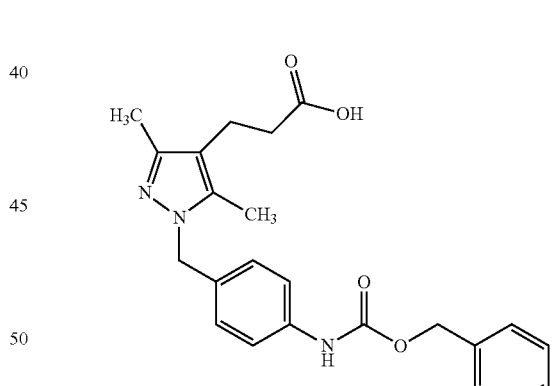

Example 3.2 was prepared according to the method described for method 3.1, employing intermediate 8.1.2 instead of intermediate 1.1.3.

Yield: 100 mg (45% of theory)

ESI mass spectrum: $[M+H]^+$=408
Retention time HPLC: 1.27 min (method D)

Carbamate formation: To a solution of [1-(4-amino-benzyl)-3,5-dimethyl-1H-pyrazol-4-yl]-acetic acid methyl ester (intermediate 1.1.3, 70 mg, 0.26 mmol) in dichloromethane (1 mL) was added diisopropylethylamine (55 μL, 0.32 mmol) and benzyl chloroformate (55 μL, 0.39 mmol). The reaction

Example 3.3

[1-(4-Benzyloxycarbonylamino-benzyl)-3,5-diethyl-1H-pyrazol-4-yl]-acetic acid

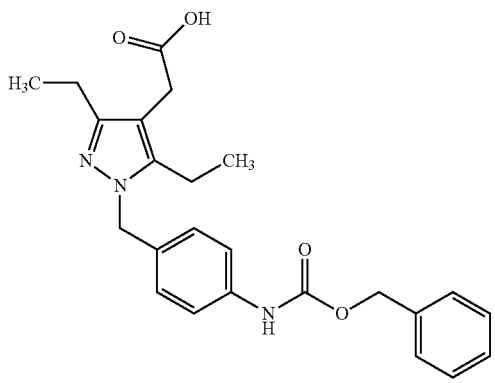 [SMILES: CCc1nn(Cc2ccc(NC(=O)OCc3ccccc3)cc2)c(CC)c1CC(=O)O]

Example 3.3 was prepared according to the method described for method 3.1, employing intermediate 2.1.2 instead of intermediate 1.1.3 in the carbamate formation step. The subsequent cleavage of the tert-butyl ester was performed under acidic conditions as described for example 2.1.

ESI mass spectrum: [M+H]$^+$=422

Retention time HPLC: 1.93 min (method B)

The following examples can be prepared in analogous fashion to example 3.1, employing in the carbamate formation step the corresponding chloroformates as coupling partners.

| Example | Structure | m/z (ESI-MS) | Rt (HPLC) (method) |
|---|---|---|---|
| 3.4 | 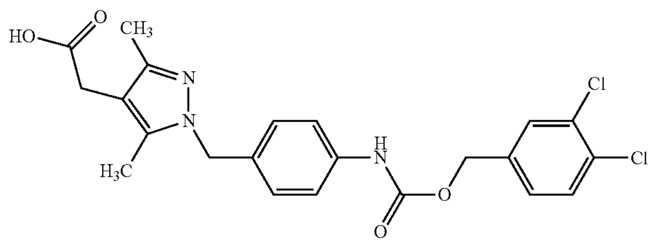 [SMILES: Cc1nn(Cc2ccc(NC(=O)OCc3ccc(Cl)c(Cl)c3)cc2)c(C)c1CC(=O)O] | 462 | 1.06 min Method J |
| 3.5 | 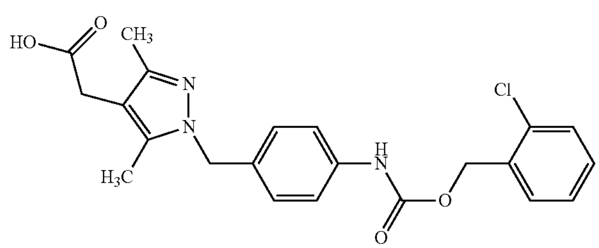 [SMILES: Cc1nn(Cc2ccc(NC(=O)OCc3ccccc3Cl)cc2)c(C)c1CC(=O)O] | 428 | 1.00 Method J |
| 3.6 | 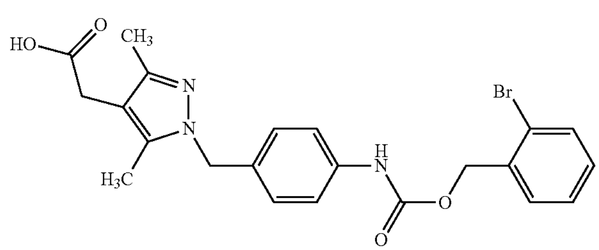 [SMILES: Cc1nn(Cc2ccc(NC(=O)OCc3ccccc3Br)cc2)c(C)c1CC(=O)O] | 472 | 1.02 min Method J |

| Example | Structure | m/z (ESI-MS) | Rt (HPLC) (method) |
|---|---|---|---|
| 3.7 | (structure) | 444 | 1.04 min Method J |

Synthesis Example 3.8

The following example can be prepared in analogous fashion to example 3.1, in which [1-(4-amino-benzyl)-3,5-dimethyl-1H-pyrazol-4-0]-acetic acid tert-butyl ester is Boc-protected.

| Example | Structure | m/z (ESI-MS) | Rt (HPLC) (method) |
|---|---|---|---|
| 3.8 | (structure) | 360 | 0.89 min Method J |

Synthesis Examples 3.9-3.12

The following examples can be prepared in analogous fashion to example 3.3, employing in the carbamate formation step the corresponding chloroformates as coupling partners.

| Example | Structure | m/z (ESI-MS) | Rt (HPLC) (method) |
|---|---|---|---|
| 3.9 | (structure) | 490 | 1.14 min Method J |
| 3.10 | (structure) | 456 | 1.07 min Method J |

| Example | Structure | m/z (ESI-MS) | Rt (HPLC) (method) |
|---|---|---|---|
| 3.11 | (pyrazole with 3,5-diethyl substituents and CH₂COOH; N-CH₂-phenyl-NH-C(O)-O-CH₂-(2-bromophenyl)) | 500 | 1.08 min Method J |
| 3.12 | (pyrazole with 3,5-diethyl substituents and CH₂COOH; N-CH₂-phenyl-NH-C(O)-O-CH₂-(2-naphthyl)) | 472 | 1.11 min Method J |

Synthesis Example 3.13-3.14

Example 3.13 was prepared according to the method described for method 3.1, employing intermediate 7.6.2 instead of intermediate 1.1.3 in the carbamate formation step. Example 3.14 was prepared according to the method described for method 3.1, employing intermediate 7.16.2 instead of intermediate 1.1.3 in the carbamate formation step.

| Example | Structure | m/z (ESI-MS) | Rt (HPLC) (method) |
|---|---|---|---|
| 3.13 | (3,5-dimethylpyrazole-CH₂COOH; N-CH₂-(2-chlorophenyl)-NH-C(O)-O-CH₂-phenyl) | 428 | 1.03 min Method J |
| 3.14 | (3,5-dimethylpyrazole-CH₂COOH; N-CH₂-(2-fluorophenyl)-NH-C(O)-O-CH₂-phenyl) | 412 | 0.98 min Method J |

Example 4.1

{1-[4-(3-Benzyl-ureido)-benzyl]-3,5-dimethyl-1H-pyrazol-4-yl}-acetic acid

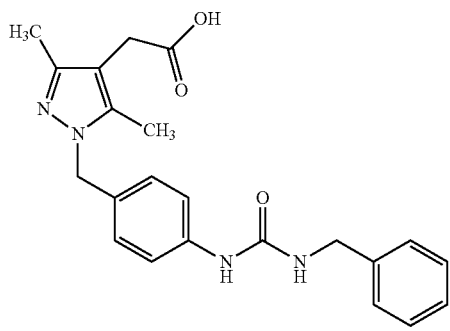 [SMILES: Cc1nn(Cc2ccc(NC(=O)NCc3ccccc3)cc2)c(C)c1CC(=O)O]

Urea formation: To a solution of [1-(4-amino-benzyl)-3,5-dimethyl-1H-pyrazol-4-yl]-acetic acid methyl ester (intermediate 1.1.3, 160 mg, 0.59 mmol) in dichloromethane (2 mL) was added benzyl isocyanate (94 µL, 0.76 mmol). The reaction mixture was stirred for 1 h at room temperature. Saponification: After removing the volatiles under reduced pressure, the remaining residue was dissolved in methanol (1 mL) and treated with aqueous LiOH solution (1 M, 1.5 mL). After 18 h, the mixture was neutralized and purified via preparative reversed phase HPLC (gradient of methanol in water+0.1% NH$_3$).

Yield: 39 mg
ESI mass spectrum: [M+H]$^+$=393
Retention time HPLC: 1.95 min (method A)

Example 5.1

[1-(4-Benzenesulfonylamino-benzyl)-3,5-dimethyl-1H-pyrazol-4-yl]-acetic acid

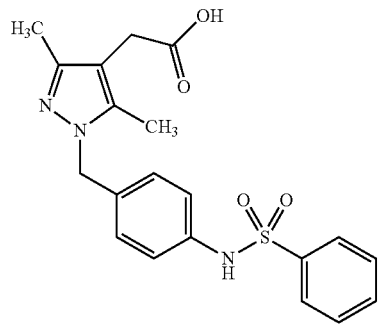 [SMILES: Cc1nn(Cc2ccc(NS(=O)(=O)c3ccccc3)cc2)c(C)c1CC(=O)O]

Sulfonamide formation: To a solution of [1-(4-amino-benzyl)-3,5-dimethyl-1H-pyrazol-4-yl]-acetic acid methyl ester (intermediate 1.1.3, 54 mg, 0.20 mmol) in dichloromethane (1 mL) was added triethylamine (72 µL, 0.51 mmol) and phenylsulfonyl chloride (36 µL, 0.25 mmol). The reaction mixture was stirred for 1 h at room temperature. The reaction mixture was filtered over Alox B, eluting with 10% methanol in dichloromethane. Saponification: After removing the volatiles under reduced pressure, the remaining residue was dissolved in methanol (0.5 mL) and treated with aqueous LiOH solution (1 M, 0.4 mL). After 1.5 h, the mixture was neutralized and purified via preparative reversed phase HPLC (gradient of methanol in water+0.1% trifluoroacetic acid).

Yield: 16 mg
ESI mass spectrum: [M+H]$^+$=400
Retention time HPLC: 1.92 min (method A)

The following examples were prepared according to the method described for example 5.1, employing the corresponding sulfonyl chlorides.

| Example | Structure | m/z (ESI-MS) | Rt (HPLC) (method) |
|---|---|---|---|
| 5.2 | ![structure] | 434/436 (Cl) (M + H)$^+$ | 1.41 min method B |
| 5.3 | ![structure] | 468/470/472 (Cl2) (M + H)$^+$ | 2.16 min method A |

| Example | Structure | m/z (ESI-MS) | Rt (HPLC) (method) |
|---|---|---|---|
| 5.4 | 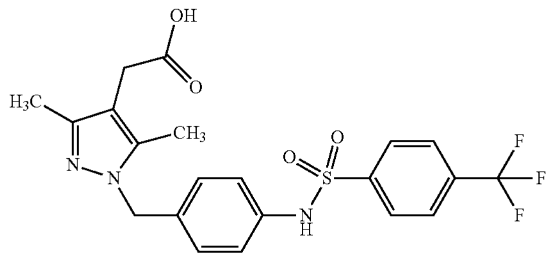 [SMILES: Cc1nn(Cc2ccc(NS(=O)(=O)c3ccc(C(F)(F)F)cc3)cc2)c(C)c1CC(=O)O] | 468 (M + H)+ | 1.48 min method B |

Example 6.1

{1-[4-(4-Chloro-benzylamino)-benzyl]-3,5-dimethyl-1H-pyrazol-4-yl}-acetic acid

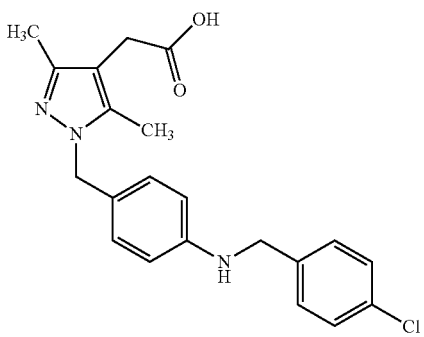 [SMILES: Cc1nn(Cc2ccc(NCc3ccc(Cl)cc3)cc2)c(C)c1CC(=O)O]

Reductive amination: To a solution of [1-(4-amino-benzyl)-3,5-dimethyl-1H-pyrazol-4-yl]-acetic acid methyl ester (intermediate 1.1.3, 100 mg, 0.37 mmol) in tetrahydrofurane (1 mL) was added 4-chlorobenzaldehyde (185 mg, 1.32 mmol) and sodium triacetoxyborohydride (240 mg, 1.13 mmol). The reaction mixture was stirred for 18 h at room temperature. The reaction mixture was filtered over Alox B, eluting with 10% methanol in dichloromethane. Saponification: After removing the volatiles under reduced pressure, the remaining residue was dissolved in methanol (1 mL) and treated with aqueous NaOH solution (4 M, 0.6 mL). After 4 h, the mixture was neutralized and purified via preparative reversed phase HPLC (gradient of methanol in water+0.1% $NH_3$).

Yield: 48 mg

ESI mass spectrum: $[M+H]^+$=384/386 (Cl)

Retention time HPLC: 2.00 min (method B)

The following examples were prepared according to the method described for example 6.1, employing the corresponding aldehydes in the reductive amination reaction.

| Example | Structure | m/z (ESI-MS) | Rt (HPLC) (method) |
|---|---|---|---|
| 6.2 | 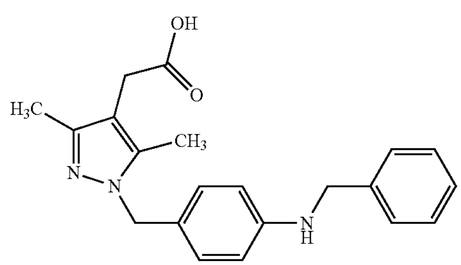 [SMILES: Cc1nn(Cc2ccc(NCc3ccccc3)cc2)c(C)c1CC(=O)O] | 350 (M + H)+ | 1.86 min method B |
| 6.3 | 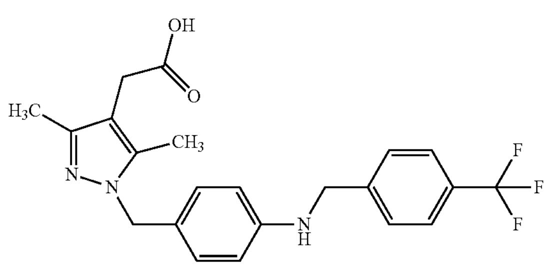 [SMILES: Cc1nn(Cc2ccc(NCc3ccc(C(F)(F)F)cc3)cc2)c(C)c1CC(=O)O] | 418 (M + H)+ | 2.05 min method B |

Example 7.1

[1-(4-Benzoylamino-3-methyl-benzyl)-3,5-dimethyl-1H-pyrazol-4-yl]-acetic acid

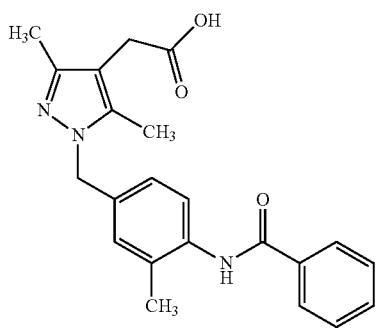 [SMILES: Cc1cc(Cn2nc(C)c(CC(=O)O)c2C)ccc1NC(=O)c1ccccc1]

Intermediate 7.1.1

[3,5-Dimethyl-1-(3-methyl-4-nitro-benzyl)-1H-pyrazol-4-yl]-acetic acid methyl ester Intermediate 7.1.1 was prepared according to the procedure for intermediate 1.1.2, employing in the alkylation reaction 3-methyl-4-nitrobenzyl bromide instead of 4-nitrobenzyl bromide.

Yield: 0.33 g (35% of theory)
ESI mass spectrum: $[M+H]^+$=318

Intermediate 7.1.2

[1-(4-Amino-3-methyl-benzyl)-3,5-dimethyl-1H-pyrazol-4-yl]-acetic acid methyl ester Intermediate 7.1.2 was prepared according to the procedure for intermediate 1.1.3, employing intermediate 7.1.1 instead of intermediate 1.1.2 in the hydrogenation reaction.

Yield: 0.33 g (quantitative)
ESI mass spectrum: $[M+H]^+$=288
Retention time HPLC: 0.85 min (method D)

Example 7.1

[1-(4-Benzoylamino-3-methyl-benzyl)-3,5-dimethyl-1H-pyrazol-4-yl]-acetic acid

Example 7.1 was prepared according to the procedure for example 1.1, employing intermediate 7.1.2 instead of intermediate 1.1.3 and benzoic acid instead of (trifluoromethyl)benzoic acid.

Yield: 47 mg (39% of theory)
ESI mass spectrum: $[M+H]^+$=378
Retention time HPLC: 0.91 min (method C)

The following examples were prepared according to the method described for example 7.1, employing the corresponding carboxylic acids as coupling partners.

| Example | Structure | m/z (ESI-MS) | Rt (HPLC) (method) |
|---|---|---|---|
| 7.2 | 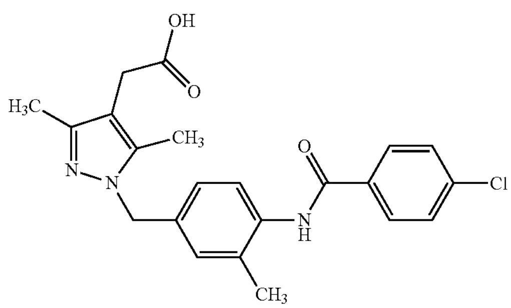 | 412/414 (Cl) $(M + H)^+$ | 1.04 min method C |
| 7.3 | 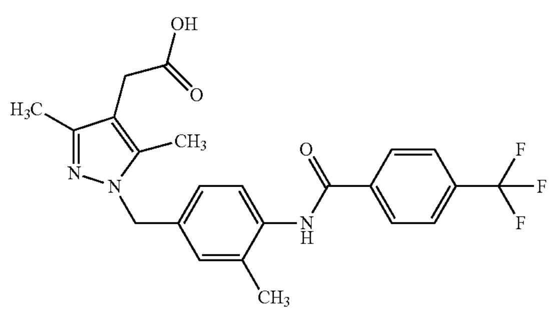 [SMILES: Cc1cc(Cn2nc(C)c(CC(=O)O)c2C)ccc1NC(=O)c1ccc(C(F)(F)F)cc1] | 446 $(M + H)^+$ | 1.09 min method C |

| Example | Structure | m/z (ESI-MS) | Rt (HPLC) (method) |
|---|---|---|---|
| 7.4 | (structure) | 446/448/450 (Cl2) (M + H)⁺ | 1.13 min method C |

Synthesis Example 7.5

Intermediate 7.5.1

4-Amino-2-methyl-benzoic acid

To a stirred solution of 4-acetylamino-2-methyl-benzoic acid (25.5 g) in methanol (250 ml) was added conc. $H_2SO_4$ (19 ml) dropwise and the reaction heated to reflux. After 2.5 h, the reaction was cooled to rt. $NaHCO_3$ (aq) was added until alkaline and the obtained mixture was extracted with EtOAc. The organic extracts were washed with NaOH(aq) (2 M) 3 times, then dried and concentrated affording 17.6 g of the title compound.

ESI mass spectrum: $[M+H]^+$=166

Intermediate 7.5.2

4-tert-Butoxycarbonylamino-2-methyl-benzoic acid methyl ester

To a stirred solution of intermediate 7.5.1 (1.5 g) in dioxane (15 ml) at 10° C. was added a solution of Boc anhydride (2.2 g) in dioxane (15 ml) dropwise and the reaction allowed to warm to rt. After 3 h, dimethylaminopyridine (catalytic amount) was added. After overnight stirring, the mixture was concentrated, and the residue was purified by flash chromatography (dichloromethan with ethanol gradient 0 to 4%) affording 0.69 g of the title compound.

ESI mass spectrum: $[M+H]^+$=266

Intermediate 7.5.3

4-tert-Butoxycarbonylamino-2-methylbenzoic acid

To a stirred solution of intermediate 7.5.2 (0.7 g) in methanol (10 ml) at room temperature was added NaOH (1M, 5.1 ml). After 5 h, further NaOH (1M, 5.1 ml) and tetrahydrofurane (3 ml) was added. After overnight stirring, further NaOH (1 M, 5.1 ml) was added. After 5 h, the mixture was concentrated, water was added and with $KHSO_4$ (aq) under ice-cooling brought to an acidic pH. After 0.5 h, the precipitate was filtered, washed with a small amount of ice-water and dried at 50° C. affording 0.55 g of the title compound.

ESI mass spectrum: $[M-H]^-$=250

Intermediate 7.5.4

(4-Hydroxymethyl-3-methyl-phenyl)-carbamic acid tert-butyl ester

To a stirred solution of intermediate 7.5.3 (0.6 g) in tetrahydrofurane (10 ml) at room temperature was added carbonyldiimidazole (0.4 g). After 0.5 h, the solution was added dropwise to a solution of $NaBH_4$ (0.25 g) in water (5 ml). After overnight stirring, the reaction was brought to an acidic pH by addition of $KHSO_4$(aq) and then extracted with diethylether 3 times. The organic layer was washed with NaOH(aq) (1 M) and water, then dried and concentrated to afford 0.28 g of the title compound.

ESI mass spectrum: $[M+H]^+$=238

Intermediate 7.5.5

Methanesulfonic acid 4-tert-butoxycarbonylamino-2-methyl-benzyl ester

To a stirred solution of intermediate 7.5.4 (0.73 g) in tetrahyrofurane (7 ml) at room temperature was added triethylamine (0.52 g). After cooling to 0° C., methanesulfonyl chloride (0.31 ml) was added dropwise. After 2 h, water was added and the mixture extracted with ethyl acetate. The organic layer was separated, dried and concentrated to afford 0.8 g of the title compound which was used without purification.

Intermediate 7.5.6

[1-(4-tert-Butoxycarbonylamino-2-methyl-benzyl)-3,5-dimethyl-1H-pyrazol-4-yl]-acetic acid methyl ester To a stirred solution of intermediate 7.5.5 (0.8 g) in $CH_3CN$ (7 ml) at room temperature was added (3,5-dimethyl-1H-pyrazol-4-yl)-acetic acid methyl ester (0.4 g) and $K_2CO_3$ (0.57 g). After 3 days, the reaction was filtered and the filtrate concentrated and the residue partitioned between dichloromethane and water. The organic layer was separated, dried and concentrated and the residue was purified via preparative reversed phase HPLC (gradient of methanol in water+0.12% TFA).

Yield: 120 mg
ESI mass spectrum: [M+H]$^+$=388
Retention time HPLC: 1.37 min (method D)

Intermediate 7.5.7

[1-(4-Amino-2-methyl-benzyl)-3,5-dimethyl-1H-pyrazol-4-yl]-acetic acid methyl ester To a stirred solution of intermediate 7.5.6 (120 mg) in dichloromethane (1 ml) at room temperature was added TFA (1 ml). After 2 h, the reaction was concentrated affording 80 mg of the title compound which was used without purification.

Example 7.5

Example 7.5 was prepared according to the procedure for example 1.1, employing 2-naphthoic acid instead of (trifluoromethyl)benzoic acid to yield 51 mg.

Intermediate 7.6.2

[1-(4-Amino-2-chloro-benzyl)-3,5-dimethyl-1H-pyrazol-4-yl]-acetic acid ethyl ester Intermediate 7.6.2 was prepared according to the procedure for intermediate 1.1.3, employing intermediate 7.6.1 instead of intermediate 1.1.2 in the hydrogenation reaction.

Yield: 2.1 g

ESI mass spectrum: [M+H]$^+$=322

Retention time HPLC: 1.76 min (method L)

| Example | Structure | m/z (ESI-MS) | Rt (HPLC) (method) |
|---|---|---|---|
| 7.5 | 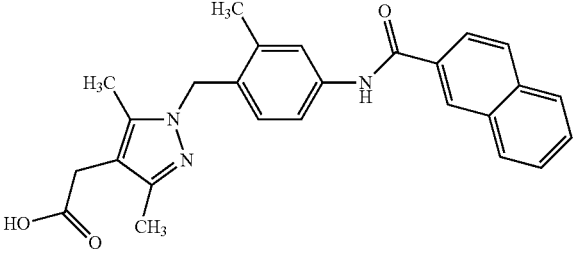 [SMILES: Cc1cc(NC(=O)c2ccc3ccccc3c2)ccc1Cn1nc(C)c(CC(=O)O)c1C] | 428 | 1.00 min<br><br>Method J |

Synthesis Examples 7.6-7.15

Example 7.6

Intermediate 7.6.1

[1-(2-Chloro-4-nitro-benzyl)-3,5-dimethyl-1H-pyrazol-4-yl]-acetic acid ethyl ester Intermediate 7.6.1 was prepared according to the procedure for intermediate 1.1.2, employing in the alkylation reaction 1-bromomethyl-2-chloro-4-nitro-benzene instead of 4-nitrobenzyl bromide.
Yield: 2.8 g
ESI mass spectrum: [M+H]$^+$=352
Retention time HPLC: 1.95 min (method L)

Example 7.6

Example 7.6 was prepared according to the procedure for example 1.1, employing intermediate 7.6.2 instead of intermediate 1.1.3 and 4-chlorobenzoic acid instead of 4-(trifluoromethyl)benzoic acid. Yield: 42 mg The examples 7.7-7.15 were prepared according to the method described for example 7.6, employing the corresponding carboxylic acids as coupling partners.

| Example | Structure | m/z (ESI-MS) | Rt (HPLC) (method) |
|---|---|---|---|
| 7.6 | 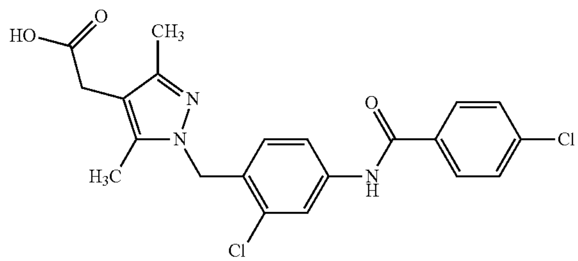 [SMILES: Cc1nn(Cc2ccc(NC(=O)c3ccc(Cl)cc3)cc2Cl)c(C)c1CC(=O)O] | 432 | 1.61 min Method L |
| 7.7 | 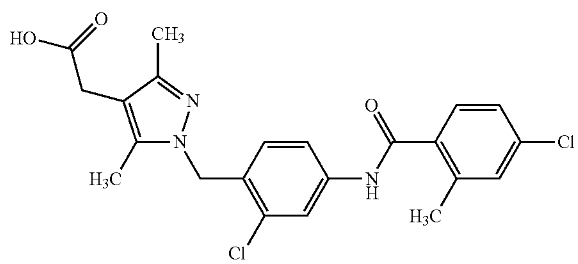 [SMILES: Cc1cc(Cl)ccc1C(=O)Nc1ccc(Cn2nc(C)c(CC(=O)O)c2C)c(Cl)c1] | 446 | 1.05 min Method J |
| 7.8 | 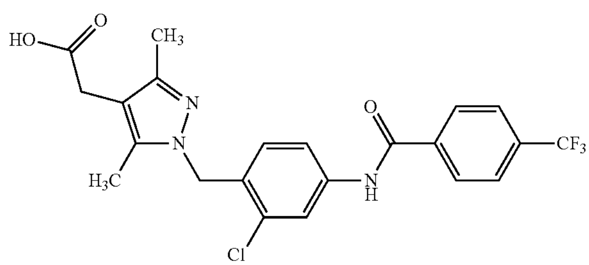 [SMILES: Cc1nn(Cc2ccc(NC(=O)c3ccc(C(F)(F)F)cc3)cc2Cl)c(C)c1CC(=O)O] | 466 | 1.08 min Method J |
| 7.9 | 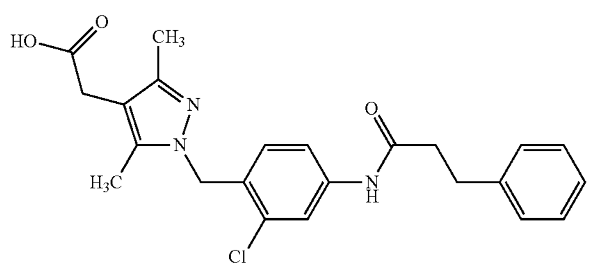 [SMILES: Cc1nn(Cc2ccc(NC(=O)CCc3ccccc3)cc2Cl)c(C)c1CC(=O)O] | 426 | 0.99 min Method J |
| 7.10 | 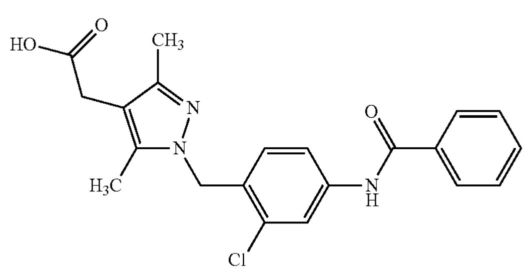 [SMILES: Cc1nn(Cc2ccc(NC(=O)c3ccccc3)cc2Cl)c(C)c1CC(=O)O] | 398 | 1.43 min Method C |
| 7.11 | 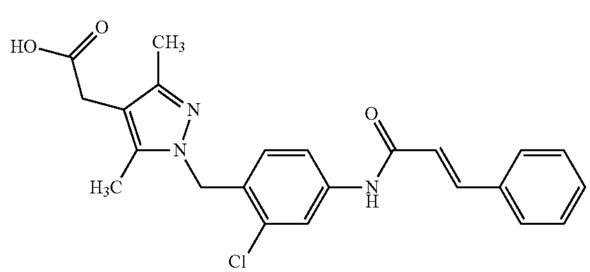 [SMILES: Cc1nn(Cc2ccc(NC(=O)/C=C/c3ccccc3)cc2Cl)c(C)c1CC(=O)O] | 424 | 1.03 min Method J |

| Example | Structure | m/z (ESI-MS) | Rt (HPLC) (method) |
|---|---|---|---|
| 7.12 | 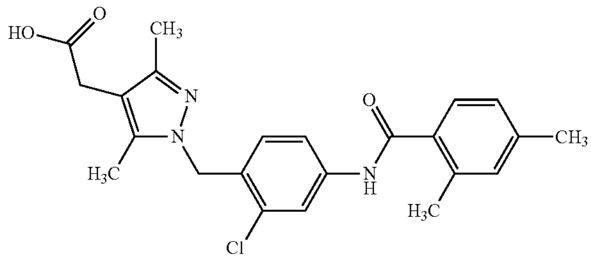 [SMILES: Cc1ccc(C(=O)Nc2ccc(Cn3nc(C)c(CC(=O)O)c3C)c(Cl)c2)c(C)c1] | 426 | 1.60 min Method C |
| 7.13 | 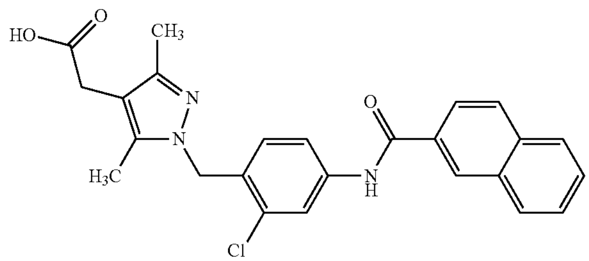 [SMILES: Cc1nn(Cc2ccc(NC(=O)c3ccc4ccccc4c3)cc2Cl)c(C)c1CC(=O)O] | 448 | 1.70 min Method C |
| 7.14 | 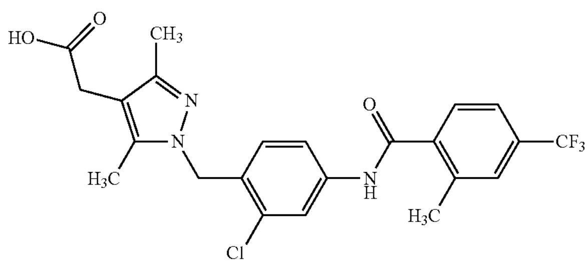 [SMILES: Cc1cc(C(F)(F)F)ccc1C(=O)Nc1ccc(Cn2nc(C)c(CC(=O)O)c2C)c(Cl)c1] | 480 | 1.73 min Method C |
| 7.15 | 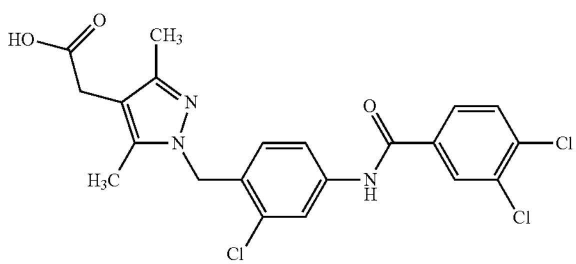 [SMILES: Cc1nn(Cc2ccc(NC(=O)c3ccc(Cl)c(Cl)c3)cc2Cl)c(C)c1CC(=O)O] | 466 | 1.80 min Method C |

Synthesis Examples 7.16-7.21

Example 7.16

Intermediate 7.16.1

[1-(2-Fluoro-4-nitro-benzyl)-3,5-dimethyl-1H-pyrazol-4-yl]-acetic acid methyl ester Intermediate 7.16.1 was prepared according to the procedure for intermediate 1.1.2, employing in the alkylation reaction 1-Bromomethyl-2-fluoro-4-nitro-benzene instead of 4-nitrobenzyl bromide.
Yield: 0.57 g
ESI mass spectrum: [M+H]$^+$=322
Retention time HPLC: 1.25 min (method D)

Intermediate 7.16.2

[1-(4-Amino-2-fluoro-benzyl)-3,5-dimethyl-1H-pyrazol-4-yl]-acetic acid methyl ester Intermediate 7.16.2 was prepared according to the procedure for intermediate 1.1.3, employing intermediate 7.16.1 instead of intermediate 1.1.2 in the hydrogenation reaction.
Yield: 0.47 g
ESI mass spectrum: [M+H]$^+$=292
Retention time HPLC: 0.92 min (method D)

Example 7.16

Example 7.16 was prepared according to the procedure for example 7.6, employing intermediate 7.16.2 instead of intermediate 1.1.3 and 2-methyl-4-trifluoromethyl-benzoic acid instead of 4-(trifluoromethyl)benzoic acid. Yield: 53 mg
The examples 7.17-7.21 were prepared according to the method described for example 7.16, employing the corresponding carboxylic acids as coupling partners.

| Example | Structure | m/z (ESI-MS) | Rt (HPLC) (method) |
|---|---|---|---|
| 7.16 | ![structure] | 464 | 1.05 min Method J |
| 7.17 | ![structure] | 450 | 1.03 min Method J |
| 7.18 | ![structure] | 450 | 1.07 min Method J |
| 7.19 | ![structure] | 430 | 1.01 min Method J |
| 7.20 | ![structure] | 432 | 1.03 min Method J |

| Example | Structure | m/z (ESI-MS) | Rt (HPLC) (method) |
|---|---|---|---|
| 7.21 | 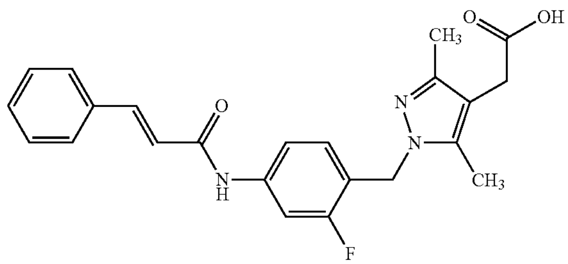 [SMILES: Cc1nn(Cc2ccc(NC(=O)/C=C/c3ccccc3)cc2F)c(C)c1CC(=O)O] | 408 | 0.98 min Method J |

Example 8.1

3-{1-[4-(4-Chloro-2-methyl-benzoylamino)-benzyl]-3,5-dimethyl-1H-pyrazol-4-yl}-propionic acid

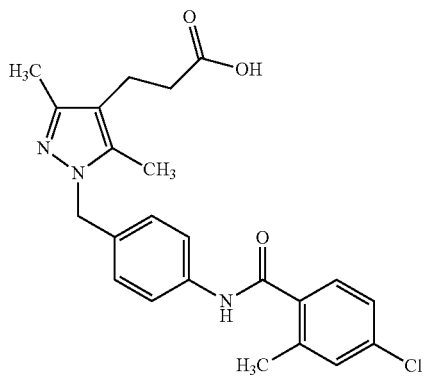 [SMILES: Cc1cc(Cl)ccc1C(=O)Nc1ccc(Cn2nc(C)c(CCC(=O)O)c2C)cc1]

Intermediate 8.1.1

3-[3,5-Dimethyl-1-(4-nitro-benzyl)-1H-pyrazol-4-yl]-propionic acid ethyl ester

Intermediate 8.1.1 can be prepared according to the method described for intermediate 1.1.2, employing in the alkylation reaction 3-(3,5-dimethyl-1H-pyrazol-4-yl)-propionic acid ethyl ester (Akos, MFCD03834497) instead of (3,5-dimethyl-1H-pyrazol-4-yl)-acetic acid methyl ester.

Intermediate 8.1.2

3-[1-(4-Amino-benzyl)-3,5-dimethyl-1H-pyrazol-4-yl]-propionic acid ethyl ester

Intermediate 8.1.2 can be prepared according to the method described for intermediate 1.1.3, employing intermediate 8.1.1 instead of intermediate 1.1.2 in the hydrogenation reaction.

ESI mass spectrum: [M+H]⁺=302

Example 8.1

3-{1-[4-(4-Chloro-2-methyl-benzoylamino)-benzyl]-3,5-dimethyl-1H-pyrazol-4-yl}-propionic acid Example 8.1 was prepared according to the method described for example 1.1, employing intermediate 8.1.2 instead of intermediate 1.1.3 and 4-chloro-2-methylbenzoic acid instead of 4-(trifluoromethyl)benzoic acid in the coupling reaction.

Yield: 144 mg (62% of theory)
ESI mass spectrum: [MA-H]⁺=426
Retention time HPLC: 1.30 min (method D)
The following examples were prepared according to the method described for example 8.1, employing the corresponding carboxylic acids as coupling partners.

| Example | Structure | m/z (ESI-MS) | Rt (HPLC) (method) |
|---|---|---|---|
| 8.2 | 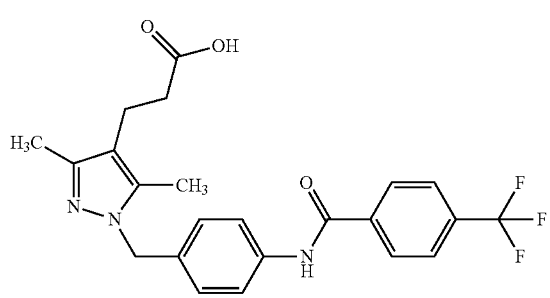 [SMILES: Cc1nn(Cc2ccc(NC(=O)c3ccc(C(F)(F)F)cc3)cc2)c(C)c1CCC(=O)O] | 446 (M + H)⁺ | 1.32 min method D |

-continued

| Example | Structure | m/z (ESI-MS) | Rt (HPLC) (method) |
|---|---|---|---|
| 8.3 | 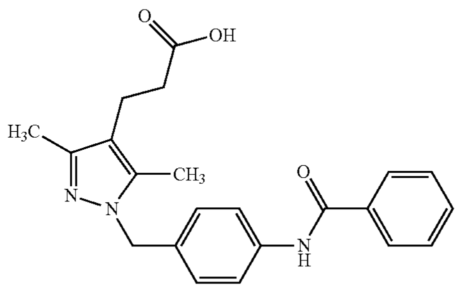 [SMILES: Cc1nn(Cc2ccc(NC(=O)c3ccccc3)cc2)c(C)c1CCC(=O)O] | 378 (M + H)+ | 0.94 min method D |
| 8.4 | 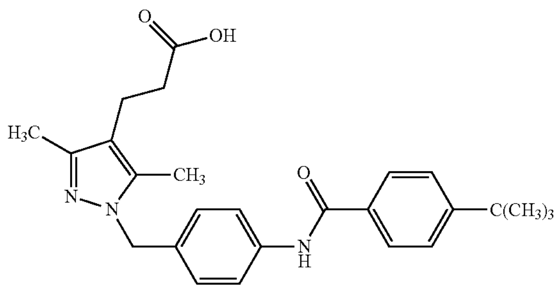 [SMILES: Cc1nn(Cc2ccc(NC(=O)c3ccc(C(C)(C)C)cc3)cc2)c(C)c1CCC(=O)O] | 434 (M + H)+ | 1.41 min method D |
| 8.5 | 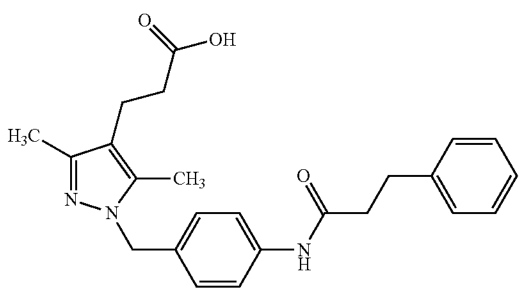 [SMILES: Cc1nn(Cc2ccc(NC(=O)CCc3ccccc3)cc2)c(C)c1CCC(=O)O] | 406 (M + H)+ | 1.23 min method D |
| 8.6 | 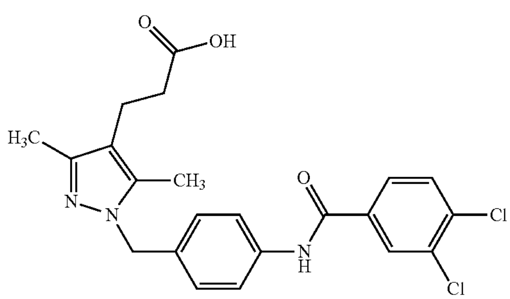 [SMILES: Cc1nn(Cc2ccc(NC(=O)c3ccc(Cl)c(Cl)c3)cc2)c(C)c1CCC(=O)O] | 446/448/450 (Cl2) (M + H)+ | 1.39 min method D |
| 8.7 | 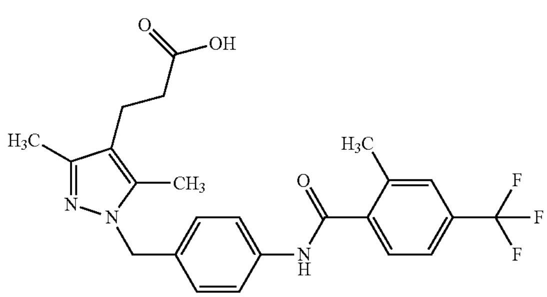 [SMILES: Cc1cc(C(F)(F)F)ccc1C(=O)Nc1ccc(Cn2nc(C)c(CCC(=O)O)c2C)cc1] | 460 (M + H)+ | 1.36 min method D |

Example 9.1

{1-[4-(3-Fluoro-phenylcarbamoyl)-benzyl]-3,5-dimethyl-1H-pyrazol-4-yl}-acetic acid

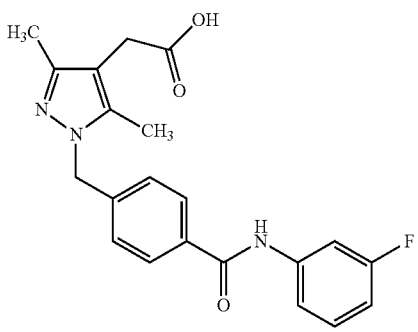 [SMILES: Cc1nn(Cc2ccc(C(=O)Nc3cccc(F)c3)cc2)c(C)c1CC(=O)O]

Intermediate 9.1.1

4-(4-Ethoxycarbonylmethyl-3,5-dimethyl-pyrazol-1-ylmethyl)-benzoic acid tert-butyl ester Intermediate 9.1.1 was prepared according to the method for intermediate 1.1.2, employing in the alkylation reaction (3,5-dimethyl-1H-pyrazol-4-yl)-acetic acid ethyl ester (Interbioscreen BB_SC-3676) instead of (3,5-dimethyl-1H-pyrazol-4-yl)-acetic acid methyl ester and 4-bromomethyl-benzoic acid tert-butyl ester instead of 4-nitrobenzyl bromide.

Yield: 4.51 g (74% of theory)
ESI mass spectrum: $[M+H]^+$=373

Intermediate 9.1.2

4-(4-Ethoxycarbonylmethyl-3,5-dimethyl-pyrazol-1-ylmethyl)-benzoic acid

To a solution of intermediate 9.1.1 (4.51 g, 12 mmol) in dichloromethane (7 mL) was added trifluoroacetic acid (25 mL) and the reaction mixture was stirred at room temperature for 18 h. The volatiles were removed under reduced pressure and the remaining oil was co-evaporated several times with toluene.

Yield: 6.60 g (contains residual trifluoroacetic acid)
ESI mass spectrum: $[M+H]^+$=317
Retention time HPLC: 1.17 min (method D)

Example 9.1

{1-[4-(3-Fluoro-phenylcarbamoyl)-benzyl]-3,5-dimethyl-1H-pyrazol-4-yl}-acetic acid Coupling: To a −10° C. solution of intermediate 9.1.2 (250 mg, 0.79 mmol) and 3-fluoroaniline (84 µL, 0.88 mmol) in dichloromethane (2 mL) was added N-methylmorpholine (0.27 mL, 2.4 mmol), followed by dropwise addition of propylphosphonic acid anhydride (0.48 mL, 1.62 mmol). After 18 h at room temperature, the volatiles were removed under reduced pressure and the remaining residue was purified by medium pressure liquid chromatography (MPLC) (silica gel, gradient 0% to 50% ethyl acetate in cyclohexane). Saponification: A solution of the ester intermediate in methanol (5 mL) was treated with aqueous NaOH solution (4 M, 0.1 mL). After 18 h, the reaction mixture was neutralized, the volatiles were removed under reduced pressure and the remaining residue was purified via preparative reversed phase HPLC (gradient of methanol in water+0.1% $NH_3$).

Yield: 18 mg
ESI mass spectrum: $[M+H]^+$=382
Retention time HPLC: 1.24 min (method D)

The following examples were prepared according to the method described for example 9.1, employing the corresponding anilines as coupling partners.

| Example | Structure | m/z (ESI-MS) | Rt (HPLC) (method) |
|---|---|---|---|
| 9.2 | 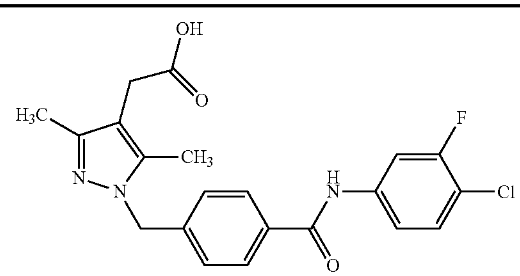 | 416/418 (Cl) $(M + H)^+$ | 1.36 min method D |
| 9.3 | 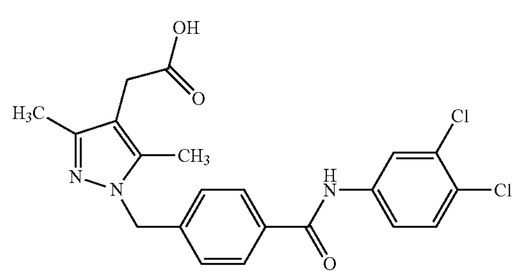 [SMILES: Cc1nn(Cc2ccc(C(=O)Nc3ccc(Cl)c(Cl)c3)cc2)c(C)c1CC(=O)O] | 432/434/436 (Cl2) $(M + H)^+$ | 1.43 min method D |

-continued

| Example | Structure | m/z (ESI-MS) | Rt (HPLC) (method) |
|---|---|---|---|
| 9.4 | 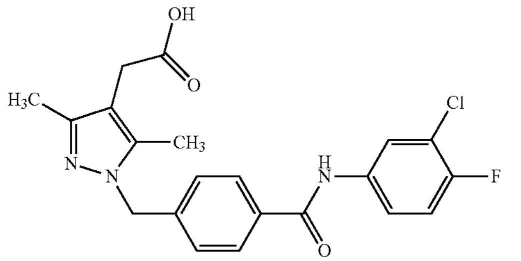 [SMILES: Cc1nn(Cc2ccc(C(=O)Nc3ccc(F)c(Cl)c3)cc2)c(C)c1CC(=O)O] | 416/418 (Cl) (M + H)+ | 1.35 min method D |
| 9.5 | 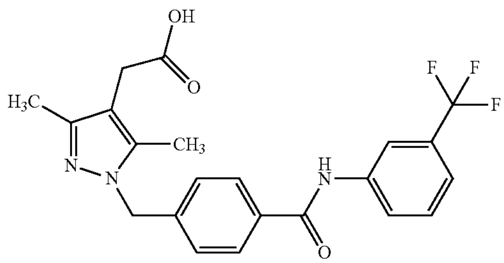 [SMILES: Cc1nn(Cc2ccc(C(=O)Nc3cccc(C(F)(F)F)c3)cc2)c(C)c1CC(=O)O] | 432 (M + H)+ | 1.35 min method D |
| 9.6 | 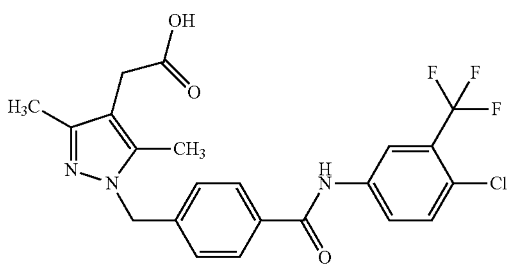 [SMILES: Cc1nn(Cc2ccc(C(=O)Nc3ccc(Cl)c(C(F)(F)F)c3)cc2)c(C)c1CC(=O)O] | 466/468 (Cl) (M + H)+ | 1.46 min method D |
| 9.7 | 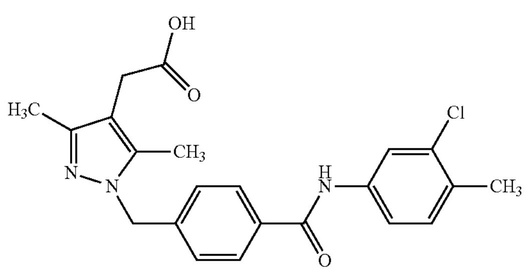 | 412/414 (Cl) (M + H)+ | 1.38 min method D |
| 9.8 | 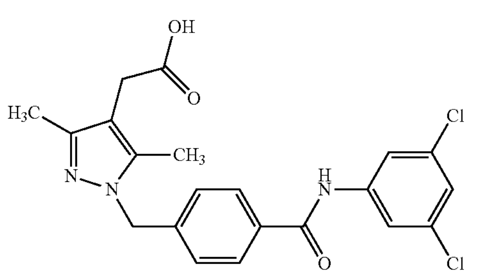 [SMILES: Cc1nn(Cc2ccc(C(=O)Nc3cc(Cl)cc(Cl)c3)cc2)c(C)c1CC(=O)O] | 432/434/436 (Cl2) (M + H)+ | 1.47 min method D |

| Example | Structure | m/z (ESI-MS) | Rt (HPLC) (method) |
|---|---|---|---|
| 9.9 | 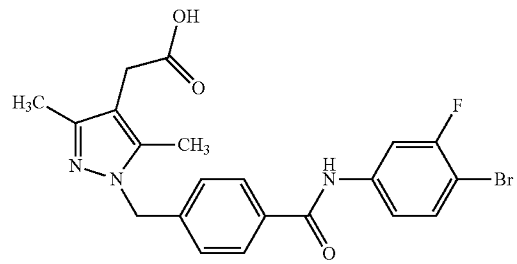 [SMILES: Cc1nn(Cc2ccc(C(=O)Nc3ccc(Br)c(F)c3)cc2)c(C)c1CC(=O)O] | 460/462 (Br) (M + H)⁺ | 1.38 min method D |

Example 9.10

{3,5-Diethyl-1-[4-(3-fluoro-phenylcarbamoyl)-benzyl]-1H-pyrazol-4-yl}-acetic acid

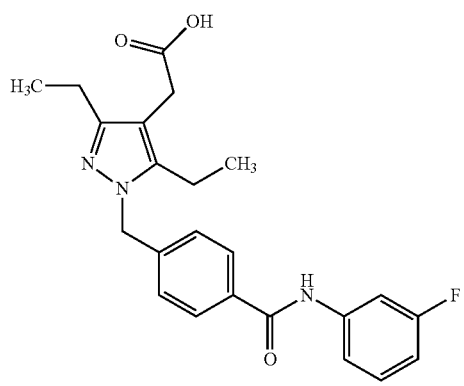 [SMILES: CCc1nn(Cc2ccc(C(=O)Nc3cccc(F)c3)cc2)c(CC)c1CC(=O)O]

Intermediate 9.10.1

4-(4-tert-Butoxycarbonylmethyl-3,5-diethyl-pyrazol-1-ylmethyl)-benzoic acid ethyl ester Intermediate 9.10.1 was prepared according to the method for intermediate 1.1.2, employing in the alkylation reaction (3,5-diethyl-1H-pyrazol-4-yl)-acetic acid tert-butyl ester instead of (3,5-dimethyl-1H-pyrazol-4-yl)-acetic acid methyl ester and 4-bromomethyl-benzoic acid ethyl ester instead of 4-nitrobenzyl bromide.

Yield: 0.67 g (40% of theory)
ESI mass spectrum: [M+H]⁺=401

Intermediate 9.10.2

4-(4-tert-Butoxycarbonylmethyl-3,5-diethyl-pyrazol-1-ylmethyl)-benzoic acid

To a solution of intermediate 9.10.1 (0.66 g, 1.65 mmol) in dioxane (25 mL) was added 1M aqueous NaOH (7 mL) and the reaction mixture was stirred at room temperature for 72 h. The reaction mixture was neutralized with 1M aqueous HCl and extracted several times with dichloromethane. The organic layer was dried over MgSO₄ and evaporated under reduced pressure.

Yield: 0.62 g (quantitative)
ESI mass spectrum: [M+H]⁺=373
Retention time HPLC: 1.43 min (method D)

Example 9.10

{3,5-Diethyl-1-[4-(3-fluoro-phenylcarbamoyl)-benzyl]-1H-pyrazol-4-yl}-acetic acid Example 9.10 was prepared according to example 2.1, employing intermediate 9.10.2 and 3-fluoroaniline in the coupling reaction.

Yield: 44 mg (32% of theory)
ESI mass spectrum: [M+H]⁺=410
Retention time HPLC: 1.34 min (method D)

The following examples were prepared in analogous fashion to example 9.10, employing the corresponding anilines as coupling partners in the last step.

| Example | Structure | m/z (ESI-MS) | Rt (HPLC) (method) |
|---|---|---|---|
| 9.11 | 3-ethyl-5-ethyl-pyrazole with CH2COOH, N-CH2-phenyl-C(O)NH-(4-chloro-3-fluorophenyl) | 444/446 (Cl) (M + H)+ | 1.43 min method D |
| 9.12 | 3-ethyl-5-ethyl-pyrazole with CH2COOH, N-CH2-phenyl-C(O)NH-(3-chloro-4-fluorophenyl) | 444/446 (Cl) (M + H)+ | 1.42 min method D |
| 9.13 | 3-ethyl-5-ethyl-pyrazole with CH2COOH, N-CH2-phenyl-C(O)NH-(4-chloro-3-trifluoromethylphenyl) | 494/496 (Cl) (M + H)+ | 1.50 min method D |
| 9.14 | 3-ethyl-5-ethyl-pyrazole with CH2COOH, N-CH2-phenyl-C(O)NH-(3-bromo-4-fluorophenyl) | 488/490 (Br) (M + H)+ | 1.42 min method D |

Example 9.15

{3,5-Di-tert-butyl-1-[4-(3-chloro-4-fluoro-phenylcarbamoyl)-benzyl]-1H-pyrazol-4-yl}-acetic acid

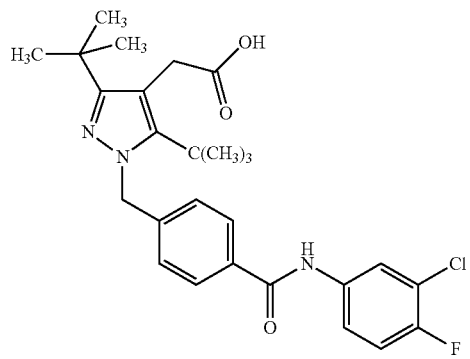 [SMILES: CC(C)(C)c1nn(Cc2ccc(C(=O)Nc3ccc(F)c(Cl)c3)cc2)c(C(C)(C)C)c1CC(=O)O]

Example 9.15 was prepared in analogous fashion to example 9.12, employing in the alkylation step (3,5-di-tert-butyl-1H-pyrazol-4-yl)-acetic acid tert-butyl ester (preparation according to the preparation of (3,5-diethyl-1H-pyrazol-4-yl)-acetic acid tert-butyl ester, WO2007/141267, employing 2,2,6,6-tetramethyl-heptane-3,5-dione instead of heptane-3,5-dione) instead of [3,5-diethyl-1H-pyrazol-4-yl]-acetic acid tert-butyl ester.

ESI mass spectrum: $[M+H]^+ = 500/502$ (Cl)
Retention time HPLC: 1.30 min (method C)

Synthesis Examples 9.16-9.26

The following examples were prepared in analogous fashion to example 9.10, employing the corresponding amine coupling partners in the last step.

| Example | Structure | m/z (ESI-MS) | Rt (HPLC) (method) |
|---|---|---|---|
| 9.16 | 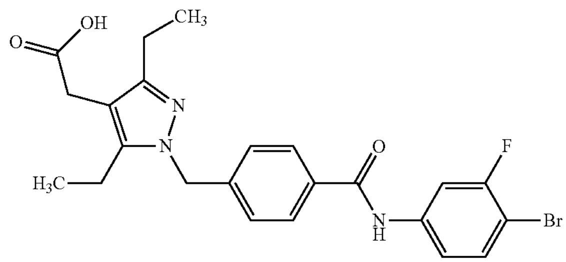 [SMILES: CCc1nn(Cc2ccc(C(=O)Nc3ccc(Br)c(F)c3)cc2)c(CC)c1CC(=O)O] | 488 | 1.10 min Method J |
| 9.17 | 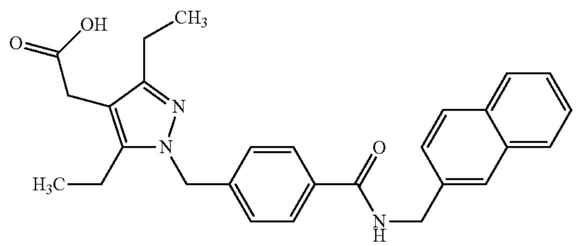 [SMILES: CCc1nn(Cc2ccc(C(=O)NCc3ccc4ccccc4c3)cc2)c(CC)c1CC(=O)O] | 456 | 1.04 min Method J |
| 9.18 | 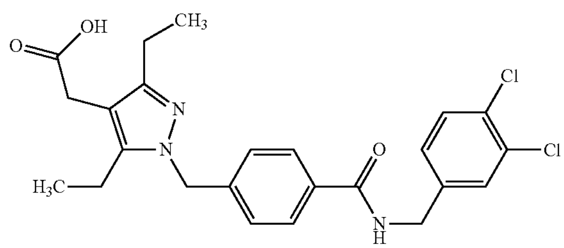 [SMILES: CCc1nn(Cc2ccc(C(=O)NCc3ccc(Cl)c(Cl)c3)cc2)c(CC)c1CC(=O)O] | 474 | 1.06 min Method J |
| 9.19 | 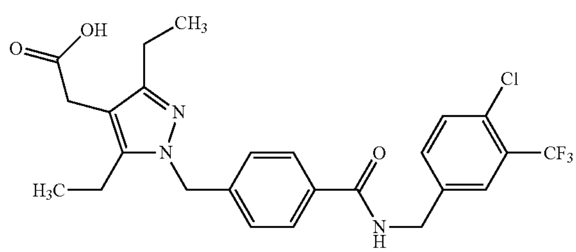 [SMILES: CCc1nn(Cc2ccc(C(=O)NCc3ccc(Cl)c(C(F)(F)F)c3)cc2)c(CC)c1CC(=O)O] | 508 | 1.10 min Method J |

-continued

| Example | Structure | m/z (ESI-MS) | Rt (HPLC) (method) |
|---|---|---|---|
| 9.20 | 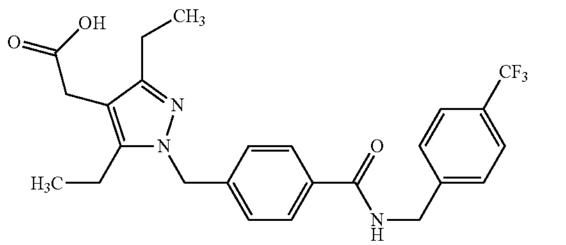 [SMILES: CCc1nn(Cc2ccc(C(=O)NCc3ccc(C(F)(F)F)cc3)cc2)c(CC)c1CC(=O)O] | 474 | 1.05 min Method J |
| 9.21 | 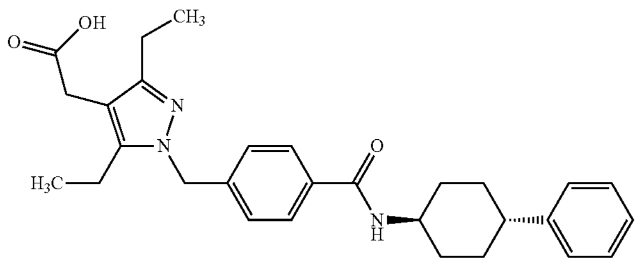 [SMILES: CCc1nn(Cc2ccc(C(=O)N[C@H]3CC[C@H](c4ccccc4)CC3)cc2)c(CC)c1CC(=O)O] | 474 | 1.12 min Method J |
| 9.22 | 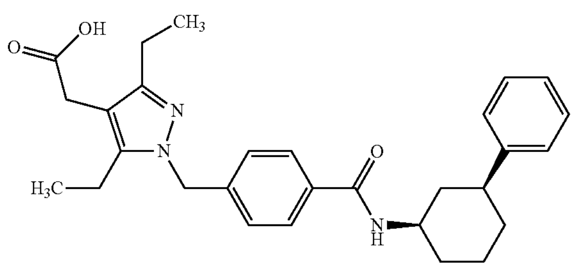 [SMILES: CCc1nn(Cc2ccc(C(=O)N[C@@H]3CCC[C@H](c4ccccc4)C3)cc2)c(CC)c1CC(=O)O] | 474 | 1.11 min Method J |
| 9.23 | 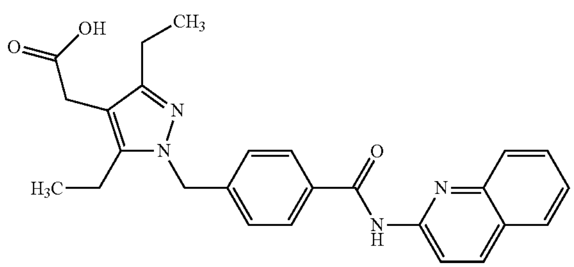 [SMILES: CCc1nn(Cc2ccc(C(=O)Nc3ccc4ccccc4n3)cc2)c(CC)c1CC(=O)O] | 443 | 0.86 min Method J |
| 9.24 | 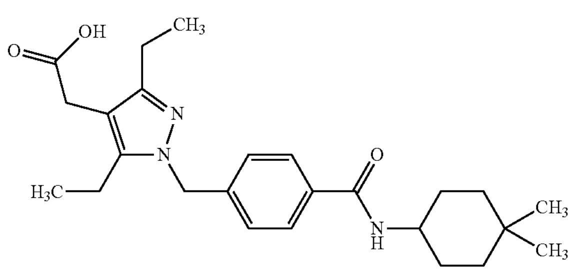 [SMILES: CCc1nn(Cc2ccc(C(=O)NC3CCC(C)(C)CC3)cc2)c(CC)c1CC(=O)O] | 426 | 1.07 min Method J |
| 9.25 | 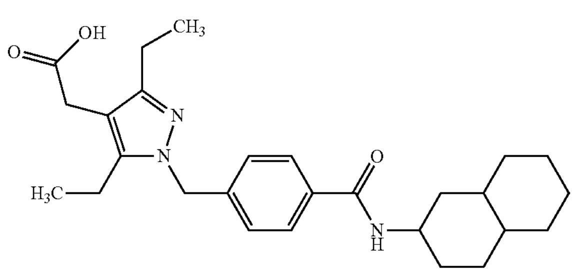 [SMILES: CCc1nn(Cc2ccc(C(=O)NC3CCC4CCCCC4C3)cc2)c(CC)c1CC(=O)O] | 452 | 1.15 min Method J |

| Example | Structure | m/z (ESI-MS) | Rt (HPLC) (method) |
|---|---|---|---|
| 9.26 | 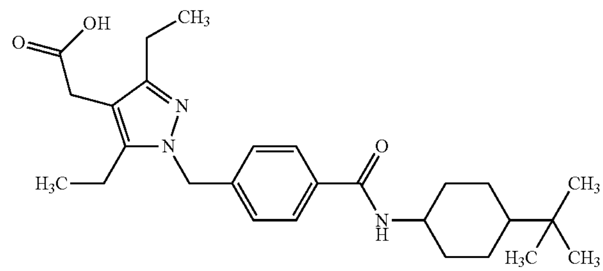 [SMILES: CCc1nn(Cc2ccc(C(=O)NC3CCC(C(C)(C)C)CC3)cc2)c(CC)c1CC(=O)O] | 454 | 1.19 min Method J |

Synthesis Examples 9.27-9.28

Intermediate 9.27.1

[1-(4-Bromo-2-fluoro-benzyl)-3,5-diethyl-1H-pyrazol-4-yl]-acetic acid tert-butyl ester To a solution of 3,5-diethyl-1H-pyrazol-4-yl)-acetic acid tert-butyl ester (prepared according to WO2007/141267) (10 g) in DMF (50 ml) at room temperature, was added 4-bromo-1-bromomethyl-2-fluoro-benzene (13.5 g) and $K_2CO_3$ (17.4 g). After overnight stirring, water was added and the mixture extracted 3 times with ethyl acetate. The organic layer was separated; washed with water and brine solution, then dried and concentrated. The residue was purified over normal phase MPLC (ethyl acetate:cyclohexane 3/97 to 30/70) to afford 13.0 g of a solid.

Retention time HPLC: 1.11 min (Method N)
ESI mass spectrum: $[M]^+=425$

Intermediate 9.27.2

4-(4-tert-Butoxycarbonylmethyl-3,5-diethyl-pyrazol-1-ylmethyl)-3-fluoro-benzoic acid To a solution of intermediate 9.27.1 (6.51 g) in dioxane (30 ml) in a microwave vial was added molybdenum hexacarbonyl (2.1 g), Hermann's catalyst (1.5 g), diisopropylethylamine (6 ml) and water (15 ml). This was heated to 150° C. in a microwave reactor. After 20 min, water was added and the mixture made alkaline with $K_2CO_3$. This was then extracted 3 times with ethyl acetate. The organic layer was separated; made acidic with glacial acetic acid, washed with water then dried and concentrated to afford 3.4 g of the title compound.

Retention time HPLC: 1.00 min (Method N)
ESI mass spectrum: $[M]^+=391$

Example 9.27

To a solution of intermediate 9.27.2 (250 mg) in DMF (5 ml) at room temperature, was added TBTU (227 mg), and diisoprpylethylamine (250 µl). After 10 min, 4-chloro-3-trifluoromethyl-phenylamine (627 mg) was added. After overnight stirring, water was added and the mixture extracted 3 times with ethyl acetate. The organic layer was separated; washed with water and brine solution, then dried and concentrated to afford 58 mg of {1-[4-(4-Chloro-3-trifluoromethyl-phenylcarbamoyl)-2-fluoro-benzyl]-3,5-diethyl-1H-pyrazol-4-yl}-acetic acid tert-butyl ester. The subsequent cleavage of the tert-butyl ester was performed under acidic conditions as described for example 2.1.

Example 9.28

Example 9.28 was prepared analogously to the method described for example 9.28, employing the corresponding carboxylic acid as coupling partner.

| Example | Structure | m/z (ESI-MS) | Rt (HPLC) (method) |
|---|---|---|---|
| 9.27 | 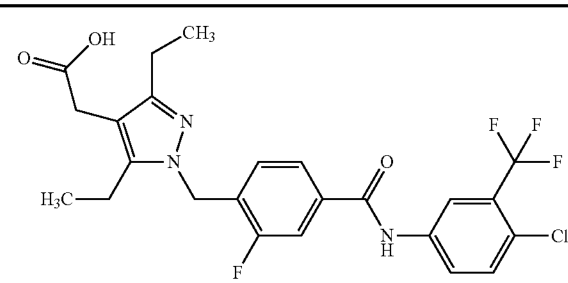 | 512 | 1.23 min Method J |

| Example | Structure | m/z (ESI-MS) | Rt (HPLC) (method) |
|---|---|---|---|
| 9.28 | 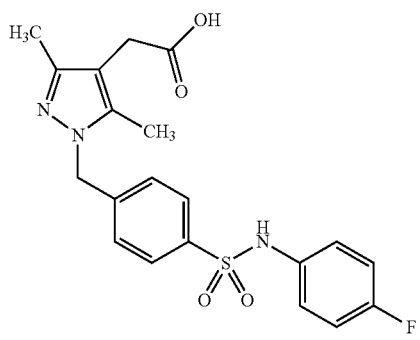 [SMILES: Cc1nn(Cc2ccc(S(=O)(=O)Nc3ccc(F)cc3)cc2)c(C)c1CC(=O)O] | 464 | 1.04 min Method J |

Example 10.1

{1-[4-(4-Fluoro-phenylsulfamoyl)-benzyl]-3,5-dimethyl-1H-pyrazol-4-yl}-acetic acid

Example 10.2

(1-{4-[2-(3,4-Dimethoxy-phenyl)-ethylsulfamoyl]-benzyl}-3,5-dimethyl-1H-pyrazol-4-yl)-acetic acid

Intermediate 10.1.1

{1-[4-(4-Fluorophenylsulfamoyl)-benzyl]-3,5-dimethyl-1H-pyrazol-4-yl}-acetic acid ethyl ester Intermediate 10.1.1 was prepared according to the method for intermediate 1.1.2, employing in the alkylation reaction (3,5-dimethyl-1H-pyrazol-4-yl)-acetic acid ethyl ester instead of (3,5-dimethyl-1H-pyrazol-4-yl)-acetic acid methyl ester and 4-bromomethyl-N-(4-fluoro-phenyl)-benzenesulfonamide (Apollo) instead of 4-nitrobenzyl bromide.

Yield: 312 mg (quantitative)
ESI mass spectrum: [M+H]$^+$=446
Retention time HPLC: 1.33 min (method D)

Example 10.1

{1-[4-(4-Fluoro-phenylsulfamoyl)-benzyl]-3,5-dimethyl-1H-pyrazol-4-yl}-acetic acid To a solution of intermediate 10.1.1 (312 mg, 0.70 mmol) in methanol (5 mL) was added aqueous NaOH solution (4 M, 1 mL) and the reaction mixture was stirred for 18 h at room temperature. The reaction mixture was neutralized, the volatiles were removed under reduced pressure and the remaining residue was purified via preparative reversed phase HPLC (gradient of methanol in water+0.1% NH$_3$).

Yield: 7 mg (2.4% of theory)
ESI mass spectrum: [M+H]$^+$=418
Retention time HPLC: 1.21 min (method D)

Example 10.2 was prepared according to the method for example 10.1, employing 4-bromomethyl-N-[2-(3,4-dimethoxy-phenyl)-ethyl]-benzenesulfonamide instead of 4-bromomethyl-N-(4-fluoro-phenyl)-benzenesulfonamide.

Yield: 105 mg (11% of theory)
ESI mass spectrum: [M+H]$^+$=488
Retention time HPLC: 1.16 min (method D)

Synthesis Examples 10.3-10.5

Intermediate 10.3.1

Di(4-bromomethylphenyl)disulfide

To a solution of di(4-tolyl)disulfide (5 g) in benzene (60 ml), was added N-bromosuccinimide (8.6 g) and the reaction heated to reflux after which azabisisobutyronitrile (0.1 g) was added. After overnight stirring, the reaction was cooled to room temperature, filtered and the filtrate concentrated. The residue was dissolved in ethyl acetate, washed successively with NaHCO$_3$(aq), water and brine solution and then concentrated. The residue was recrystallized from 9:1 cyclohexane/ethyl acetate affording 1.5 g of a solid which was used without further purification.

Intermediate 10.3.2

(1-{4-[4-(4-Ethoxycarbonylmethyl-3,5-diethyl-pyrazol-1-ylmethyl)-phenyldisulfanyl]-benzyl}-3,5-diethyl-1H-pyrazol-4-yl)-acetic acid ethyl ester To a stirred solution of (3,5-diethyl-1H-pyrazol-4-yl)-acetic acid ethyl ester (prepared according to WO2007/141267) (1.3 g) in $CH_3CN$ (25 ml), was added intermediate 10.3.2 (1.8 g) and $K_2CO_3$ (0.9 g) and the reaction heated to reflux. After 3 h, the reaction was filtered, and the filtrate concentrated. Flash chromatography (dichloromethane:methanol 100:0 to 97:3) afford 0.95 g of the title compound. ESI mass spectrum: $[M+H]^+=663$

Intermediate 10.3.3

[3,5-Diethyl-1-(4-methoxysulfinyl-benzyl)-1H-pyrazol-4-yl]-acetic acid ethyl ester To a stirred solution of intermediate 10.3.2 (840 mg) in methanol (15 ml) at 0° C., was added N-bromosuccinimide (700 mg). After 1 h, the reaction was diluted with dichloromethane filtered, and washed successively with $NaHCO_3$ (aq), and brine solution, then dried and concentrated. Flash chromatography (dichloromethane:methanol 100:0 to 99:1) afforded 1.0 g of the title compound. ESI mass spectrum: $[M+H]^+=379$.

Intermediate 10.3.4

{1-[4-(3-Chloro-4-methyl-phenylsulfinamoyl)-benzyl]-3,5-diethyl-1H-pyrazol-4-yl}-acetic acid ethyl ester To a stirred solution of 3-chloro-4-methyl aniline (170 mg) in tetrahydrofurane (15 ml) at −78° C. was added n-butyllithium (1.6M in hexane, 0.75 ml). After 30 min, this solution was added dropwise to a solution of intermediate 10.3.3 (250 mg) in tetrahydrofurane (10 ml). After 4 h, $NaHPO_4$ (aq, 0.1 M) was added and the mixture extracted 2 times with dichloromethane. The organic layer was then dried and concentrated affording 325 mg of the title compound which was used without further purification.

Example 10.3

To a stirred solution of intermediate 10.3.4 (325 mg) in dichloromethane (10 ml) at 0° C., was added m-chloroperbenzoic acid (200 mg). After 0.5 h, $NaHSO_3$(aq) was added and after a further 5 min, the organic layer was separated and washed with $NaHCO_3$(aq), then dried and concentrated affording {1-[4-(3-Chloro-4-methyl-phenylsulfamoyl)-benzyl]-3,5-diethyl-1H-pyrazol-4-yl}-acetic acid ethyl ester which was used without further purification. ESI mass spectrum: $[M+H]^+=504$. Saponification: The residue was taken up in dioxane (5 ml) and treated with aqueous NaOH solution (1 M, 1.1 ml) and heated to 50° C. After 1 h, HCl (aq) was added to an acidic pH, and the mixture was extracted with 9:1 diethylether:tetrahydrofurane. The organic layer was washed with brine solution, dried and concentrated. The residue was purified via preparative reversed phase HPLC (gradient of methanol in water+0.1% TFA) to afford 85 mg of the title compound.

Examples 10.4-10.5 were prepared according to the method described for example 10.3, employing the corresponding anilines in the sulfinic acid amide formation step.

| Example | Structure | m/z (ESI-MS) | Rt (HPLC) (method) |
|---------|-----------|--------------|--------------------|
| 10.3 | 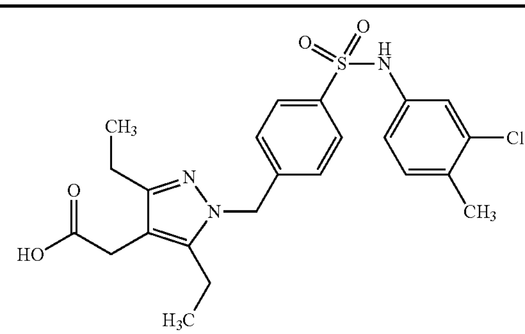 | 476 | 1.09 min Method J |
| 10.4 | 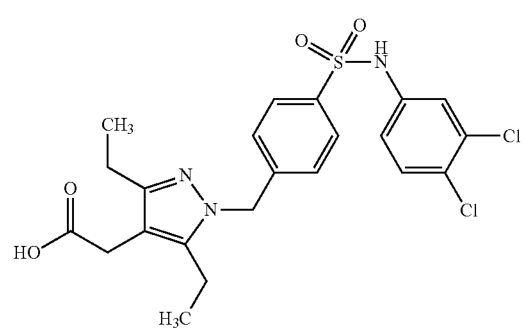 [SMILES: CCc1nn(Cc2ccc(S(=O)(=O)Nc3ccc(Cl)c(Cl)c3)cc2)c(CC)c1CC(=O)O] | 496 | 1.12 min Method J |

| Example | Structure | m/z (ESI-MS) | Rt (HPLC) (method) |
|---|---|---|---|
| 10.5 | 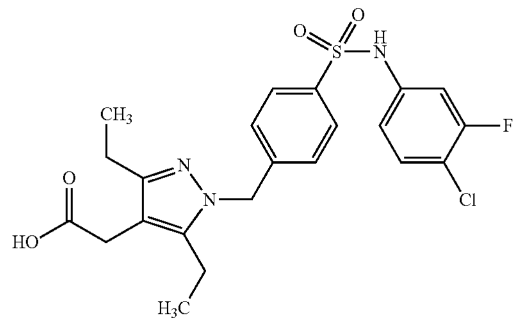 [SMILES: CCc1nn(Cc2ccc(S(=O)(=O)Nc3ccc(Cl)c(F)c3)cc2)c(CC)c1CC(=O)O] | 480 | 1.08 min Method J |

Example 11.1

N-{4-[(3,5-Dimethyl-4-{[(2-methylpropane-2-sulfonyl)carbamoyl]methyl}-1H-pyrazol-1-yl)methyl]phenyl}-4-(trifluoromethyl)benzamide

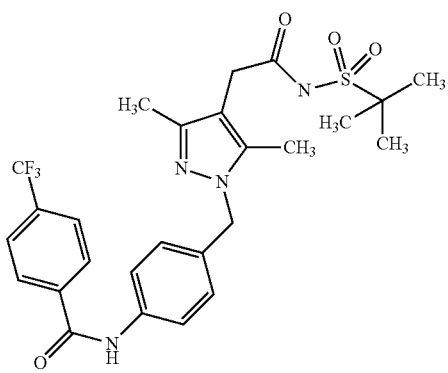 [SMILES: Cc1nn(Cc2ccc(NC(=O)c3ccc(C(F)(F)F)cc3)cc2)c(C)c1CC(=O)NS(=O)(=O)C(C)(C)C]

{3,5-Dimethyl-1-[4-(4-trifluoromethyl-benzoylamino)-benzyl]-1H-pyrazol-4-yl}-acetic acid (example 1.1, 250 mg, 0.58 mmol), 2-methylpropane-2-sulfonamide (95 mg, 0.70 mmol), 1,3-dicyclohexylcarbodiimid (143 mg, 0.70 mmol) and 4-dimethylaminopyridine (85 mg, 0.70 mmol) in 2.5 ml dichloromethane were stirred for 3 h at 30° C. The solvent was removed under reduced pressure and the residue was purified by MPLC (silica gel, CH$_2$Cl$_2$/methanol 95:5).

Yield: 51 mg
ESI mass spectrum: [M+H]$^+$=551
Retention time HPLC: 1.34 min (method D).

Example 12.1

{3,5-Dimethyl-1-[4-(4-trifluoromethyl-phenylethynyl)-benzyl]-1H-pyrazol-4-yl}-acetic acid

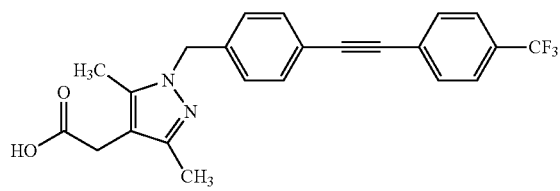

Intermediate 12.1.1

[1-(4-Bromobenzyl)-3,5-dimethyl-1H-pyrazol-4-yl]-acetic acid methyl ester

To a solution of (3,5-dimethyl-1H-pyrazol-4-yl)-acetic acid methyl ester (6 g, 36 mmol) and 4-bromobenzyl bromide (8.9 g, 36 mmol) in 80 ml acetonitrile was added K$_2$CO$_3$ (4.9 g, 36 mmol). The mixture was stirred for 12 h at room temperature, 12 h at 50° C., and after addition of an additional 1 g of K$_2$CO$_3$ the mixture was stirred for another 12 h at room temperature. The mixture was concentrated by under reduced pressure, poured into water and extracted twice with ethyl acetate, dried with MgSO$_4$ and evaporated under reduced pressure.

Yield: 7.9 g
ESI mass spectrum: [M+H]$^+$=337

Example 12.1

{3,5-Dimethyl-1-[4-(4-trifluoromethyl-phenylethynyl)-benzyl]-1H-pyrazol-4-yl}-acetic acid Heck coupling: A solution of [1-(4-bromo-benzyl)-3,5-dimethyl-1H-pyrazol-4-yl]-acetic acid methyl ester (intermediate 12.1.1, 500 mg, 1.5 mmol), 4-trifluoromethyl-phenylacetylene (0.24 ml, 1.5 mmol) and diisopropylethylamine (0.51 ml, 3 mmol) in 15 ml tetrahydrofurane was degassed, and CuI (28 mg, 0.15 mmol) and bis-(triphenylphosphin)-palladium dichloride (104 mg, 0.15 mmol) were added to the solution. The mixture was refluxed for 12 h, the solvent evaporated under reduced pressure, and the residue was purified by MPLC (silica gel, cyclohexane/ethyl acetate 98:2). Saponification: The ester intermediate (170 mg, 0.4 mmol) was dissolved in 1 ml dioxan, 1 ml water and aqueous NaOH solution (0.8 ml, 1 M) was added. After stirring for 1 h, aqueous HCl solution (0.84 ml, 1 M) was added. The mixture was extracted with ethyl acetate, the organic layer was dried with MgSO$_4$ and evaporated under reduced pressure. The residue was purified by MPLC (silica gel, CH$_2$Cl$_2$/methanol 9:1) and preparative reversed phase HPLC (gradient of methanol in water+0.1 NH$_3$).

Yield: 41 mg
ESI mass spectrum: [M+H]$^+$=413
Retention time HPLC: 1.56 min (method D).

Example 12.2

(3,5-Dimethyl-1-{4-[(E)-2-(4-trifluoromethyl-phenyl)-vinyl]-benzyl}-1H-pyrazol-4-yl)-acetic acid

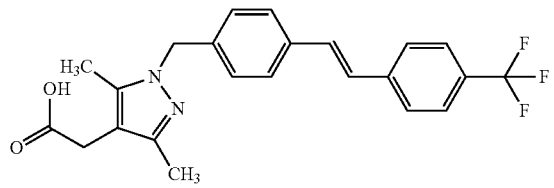 [SMILES: Cc1nn(Cc2ccc(/C=C/c3ccc(C(F)(F)F)cc3)cc2)c(C)c1CC(=O)O]

A solution of [1-(4-bromo-benzyl)-3,5-dimethyl-1H-pyrazol-4-yl]-acetic acid methyl ester (intermediate 12.1.1, 500 mg, 1.5 mmol), 4-(trifluoromethyl)styrene (0.24 ml, 1.6 mmol) and diisopropylethylamine (0.38 ml, 2.2 mmol) in 10 ml dimethylformamide was degassed, and Pd(II) acetate (33 mg, 0.15 mmol) and tri(o-tolyl)phosphine (45 mg, 0.15 mmol) were added to the solution under argon. The mixture was heated for 4 h at 90° C. and stirred for 12 h at room temperature. The mixture was poured into water and extracted twice with ethyl acetate. The organic layer was separated, dried over MgSO$_4$ and the solvent was evaporated under reduced pressure. The residue was purified by MPLC (silica gel, CH$_2$Cl$_2$/methanol 99:1). Saponification: The ester intermediate (530 mg, 1.24 mmol) was dissolved in 5 ml dioxane and aqueous NaOH solution (2.5 ml, 1 M). After stirring for 1 h and dilution with water, aqueous HCl solution (2.6 ml, 1 M) was added. The mixture was extracted with ethyl acetate, the organic layer was dried with MgSO$_4$ and evaporated under reduced pressure. The residue was purified by MPLC (silica gel, CH$_2$Cl$_2$/methanol 91:9) and preparative reversed phase HPLC (gradient of methanol in water+0.1% NH$_3$).

Yield: 173 mg
ESI mass spectrum: [M+H]$^+$=415
Retention time HPLC: 1.31 min (method D).

Synthesis Example 12.3

The following example was prepared in analogous fashion to example 12.2, employing [1-(4-bromobenzyl)-3,5-diethyl-1H-pyrazol-4-yl]-acetic acid tert-butyl ester instead of [1-(4-bromo-benzyl)-3,5-dimethyl-1H-pyrazol-4-yl]-acetic acid methyl ester. The corresponding styrene was used in the last step.

Example 13.1

{1-[4-(3,4-Dichloro-benzyloxy)-benzyl]-3,5-dimethyl-1H-pyrazol-4-yl}-acetic acid

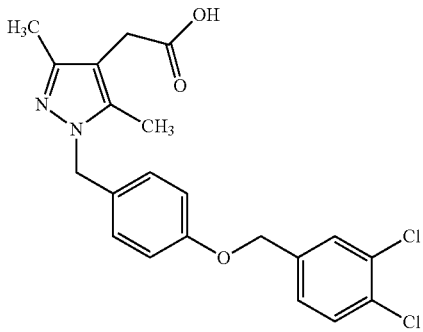 [SMILES: Cc1nn(Cc2ccc(OCc3ccc(Cl)c(Cl)c3)cc2)c(C)c1CC(=O)O]

Intermediate 13.1.1

4-(3,4-Dichloro-benzyloxy)-benzoic acid methyl ester

A mixture of methyl 4-hydroxybenzoate (0.30 g, 2.0 mmol), 3,4-dichlorobenzyl chloride (0.30 mL, 2.2 mmol) and K$_2$CO$_3$ (0.41 g, 3.0 mmol) in dimethylformamide (5 mL) was stirred at room temperature for 24 h. The reaction mixture was poured into water and extracted twice with diethyl ether. The organic layer was collected, dried over MgSO$_4$ and evaporated under reduced pressure.

Yield: 591 mg
ESI mass spectrum: [M+H]$^+$=311/313/315 (Cl$_2$)
Retention time HPLC: 2.33 min (method H)

Intermediate 13.1.2

[4-(3,4-Dichlorobenzyloxy)-phenyl]-methanol

Under nitrogen atmosphere 4-(3,4-dichloro-benzyloxy)-benzoic acid methyl ester (intermediate 13.1.1, 0.59 g, 1.90 mmol) was dissolved in dry tetrahydrofurane (10 mL) and a solution of lithiumaluminium hydride (1 M in tetrahydrofurane, 2.85 mL) was added dropwise. The reaction mixture was stirred at room temperature for 3 h. The reaction mixture was cooled to 0° C. and water was carefully added dropwise until gas evolution ceased. The reaction mixture was diluted

| Example | Structure | m/z (ESI-MS) | Rt (HPLC) (method) |
|---|---|---|---|
| 12.3 | | 409 | 1.25 min Method J | with diethyl ether and salts were filtered off. The organic layer was dried over MgSO₄ and evaporated under reduced pressure.

Yield: 470 mg
ESI mass spectrum: [M+H—H₂O]⁺=265/267/269 (Cl₂)
Retention time HPLC: 1.80 min (method H)

Intermediate 13.1.3

4-(4-Bromomethyl-phenoxymethyl)-1,2-dichlorobenzene

To a solution of [4-(3,4-dichloro-benzyloxy)-phenyl]-methanol (intermediate 13.1.2, 0.47 g, 1.24 mmol) in methyl tert-butyl ether (10 mL) was added phosphorus tribromide (1 M in dichloromethane, 1.24 mL) and the mixture was heated at 50° C. under nitrogen atmosphere for 2 h. The reaction mixture was cooled to room temperature and poured into aqueous NaHCO₃ solution. The organic layer was separated, dried over MgSO₄, and evaporated under reduced pressure.

Yield: 366 mg
ESI mass spectrum: [M+H]⁺=345/347/349/351 (Br, Cl₂)
Retention time HPLC: 2.45 min (method H)

Example 13.1

{1-[4-(3,4-Dichloro-benzyloxy)-benzyl]-3,5-dimethyl-1H-pyrazol-4-yl}-acetic acid Alkylation: To a solution of [3,5-dimethyl-1H-pyrazol-4-yl]-acetic acid tert-butyl ester (intermediate 17.1.1, 150 mg, 0.71 mmol) in dimethylformamide (3 mL) under nitrogen atmosphere was added sodium hydride (60% in mineral oil, 34 mg, 0.84 mmol) and the mixture was stirred at room temperature for 1 h. Then, a solution of 4-(4-bromomethyl-phenoxymethyl)-1,2-dichloro-benzene (intermediate 13.1.3, 270 mg, 0.78 mmol) in dimethylformamide (1 mL) was added and the reaction mixture was stirred at room temperature for 3 h. The reaction mixture was poured into water (20 mL) and extracted with ethyl acetate, the combined organic phase was dried over MgSO₄ and evaporated under reduced pressure. Ester cleavage: The crude ester intermediate was dissolved in dichloromethane (5 mL) and treated with trifluoroacetic acid (1 mL). After 4 h, the mixture was concentrated under reduced pressure and purified via preparative reversed phase HPLC (gradient of acetonitrile in water+0.1% trifluoroacetic acid).

Yield: 67 mg
ESI mass spectrum: [M+H]⁺=419/421/423 (Cl₂)
Retention time HPLC: 8.80 min (method E)

The following examples were prepared according to the method described for Example 13.1, employing in the alkylation step the corresponding bromobenzyl- or chlorobenzyl-derivatives instead of intermediate 13.1.3.

| Example | Structure | m/z (ESI-MS) | Rt (HPLC) (method) |
|---|---|---|---|
| 13.2 | 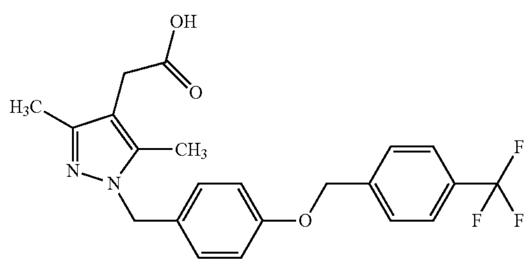 [SMILES: Cc1nn(Cc2ccc(OCc3ccc(C(F)(F)F)cc3)cc2)c(C)c1CC(=O)O] | 419 (M + H)⁺ | 8.35 min method E |
| 13.3 | 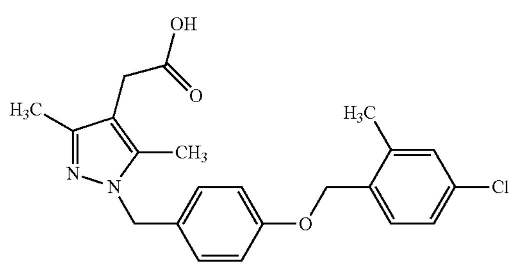 [SMILES: Cc1cc(Cl)ccc1COc1ccc(Cn2nc(C)c(CC(=O)O)c2C)cc1] | 399/401 (Cl) (M + H)⁺ | 8.30 min method E |
| 13.4 | 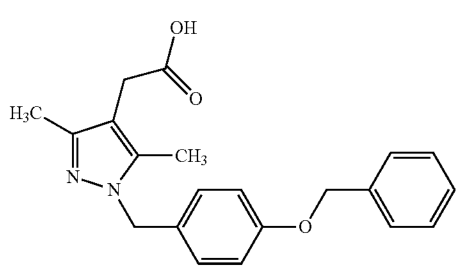 [SMILES: Cc1nn(Cc2ccc(OCc3ccccc3)cc2)c(C)c1CC(=O)O] | 351 (M + H)⁺ | 6.89 min method E |

| Example | Structure | m/z (ESI-MS) | Rt (HPLC) (method) |
|---|---|---|---|
| 13.5 | 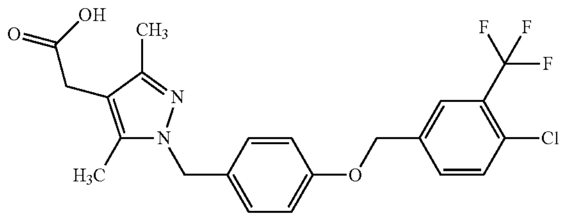 [SMILES: Cc1nn(Cc2ccc(OCc3ccc(Cl)c(C(F)(F)F)c3)cc2)c(C)c1CC(=O)O] | 453 | 1.16 min Method J |
| 13.6 | 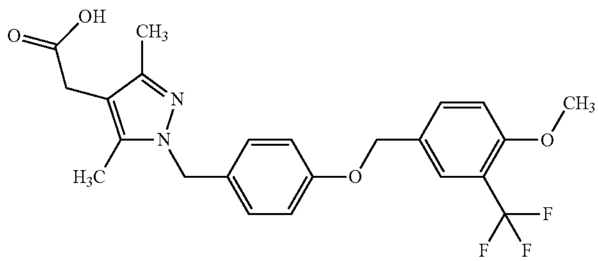 [SMILES: COc1ccc(COc2ccc(Cn3nc(C)c(CC(=O)O)c3C)cc2)cc1C(F)(F)F] | 449 | 1.50 min Method M |

Synthesis Examples 13.7-13.13

The following examples were prepared according to the method described for Example 13.1, employing (3,5-diethyl-1H-pyrazol-4-yl)-acetic acid tert-butyl ester instead of (3,5-dimethyl-1H-pyrazol-4-yl)-acetic acid tert-butyl ester. In the alkylation step, the corresponding bromobenzyl- or chlorobenzyl-derivatives instead of intermediate 13.1.3 were used.

| Example | Structure | m/z (ESI-MS) | Rt (HPLC) (method) |
|---|---|---|---|
| 13.7 | 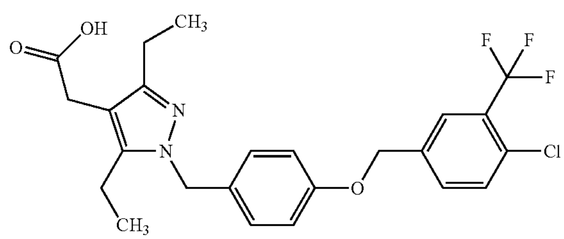 [SMILES: CCc1nn(Cc2ccc(OCc3ccc(Cl)c(C(F)(F)F)c3)cc2)c(CC)c1CC(=O)O] | 481 | 1.24 min Method J |
| 13.8 | 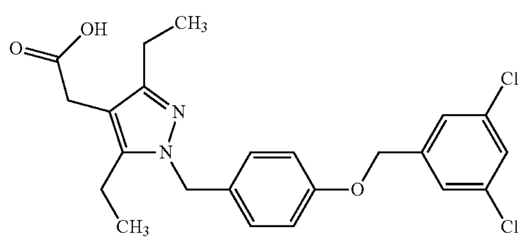 [SMILES: CCc1nn(Cc2ccc(OCc3cc(Cl)cc(Cl)c3)cc2)c(CC)c1CC(=O)O] | 447 | 1.25 min Method J |
| 13.9 | 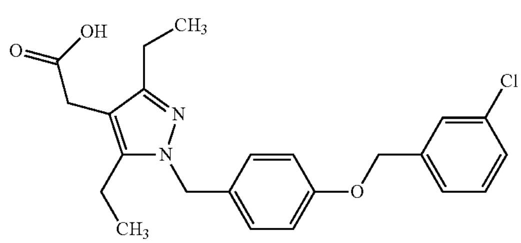 [SMILES: CCc1nn(Cc2ccc(OCc3cccc(Cl)c3)cc2)c(CC)c1CC(=O)O] | 413 | 1.15 min Method J |

-continued

| Example | Structure | m/z (ESI-MS) | Rt (HPLC) (method) |
|---|---|---|---|
| 13.10 | 3,5-diethyl-1-[4-(3-trifluoromethylbenzyloxy)benzyl]-1H-pyrazol-4-yl acetic acid | 447 | 1.80 min Method M |
| 13.11 | 1-[4-(3-chloro-4-trifluoromethoxybenzyloxy)benzyl]-3,5-diethyl-1H-pyrazol-4-yl acetic acid | 497 | 1.99 min Method M |
| 13.12 | 3,5-diethyl-1-[4-(4-methoxy-3-trifluoromethylbenzyloxy)benzyl]-1H-pyrazol-4-yl acetic acid | 477 | 1.16 min Method J |
| 13.13 | 3,5-diethyl-1-[4-(3-methylbenzyloxy)benzyl]-1H-pyrazol-4-yl acetic acid | 393 | 1.70 min Method M |

Example 14.1

{3,5-Dimethyl-1-[4-(4-trifluoromethyl-phenoxymethyl)-benzyl]-1H-pyrazol-4-yl}-acetic acid

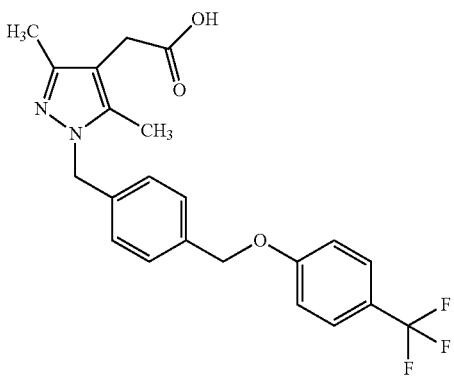 [SMILES: Cc1nn(Cc2ccc(COc3ccc(C(F)(F)F)cc3)cc2)c(C)c1CC(=O)O]

Intermediate 14.1.1

4-(4-Trifluoromethyl-phenoxymethyl)-benzoic acid methyl ester

A mixture of methyl 4-(bromomethyl)benzoate (0.31 g, 1.4 mmol), 4-hydroxy-benzotrifluoride (0.20 g, 1.2 mmol) and $K_2CO_3$ (0.26 g, 1.9 mmol) in dimethylformamide (3 mL) was stirred at 50° C. for 3 h. The reaction mixture was poured into water and extracted twice with diethyl ether. The organic layer was collected, dried over $MgSO_4$, concentrated under reduced pressure.

Yield: 430 mg (containing residual dimethylformamide)
ESI mass spectrum: $[M+H]^+=311$
Retention time HPLC: 2.18 min (method H)

Intermediate 14.1.2

[4-(4-Trifluoromethyl-phenoxymethyl)-phenyl]-methanol

[4-(4-Trifluoromethyl-phenoxymethyl)-phenyl]-methanol was prepared according to the preparation of intermediate 13.1.2 using intermediate 14.1.1 instead of intermediate 13.1.1.
Yield: 340 mg
ESI mass spectrum: $[M+H]^+=283$
Retention time HPLC: 10.2 min (method E)

Intermediate 14.1.3

4-(4-Chloromethyl-benzyloxy)-trifluoromethylbenzene

To a solution of [4-(4-trifluoromethyl-phenoxymethyl)-phenyl]-methanol (intermediate 14.1.2, 0.34 g, 1.2 mmol) in dichloromethane (10 mL) were added triethylamine (0.34 mL, 2.4 mmol) and methanesulfonyl chloride (0.19 mL, 2.4 mmol). The reaction mixture was stirred at room temperature for 36 h under nitrogen atmosphere. The reaction mixture was washed with water, the organic layer was dried over MgSO4 and the solvent was evaporated under reduced pressure.
Yield: 188 mg
ESI mass spectrum: $[M+H]^+=300/2$ (Cl)
Retention time HPLC: 12.0 min (method E)

Example 14.1

{3,5-Dimethyl-1-[4-(4-trifluoromethyl-phenoxymethyl)-benzyl]-1H-pyrazol-4-yl}-acetic acid Example 14.1 was prepared according to the procedure of Example 13.1, employing in the alkylation reaction intermediate 14.1.3 instead of intermediate 13.1.3.
Yield: 22 mg
ESI mass spectrum: $[M+H]^+=419$
Retention time HPLC: 8.07 min (method E)

The following examples were prepared according to the method described for example 14.1, employing in the alkylation step the corresponding bromobenzyl- or chlorobenzyl-derivatives instead of intermediate 14.1.3.

| Example | Structure | m/z (ESI-MS) | Rt (HPLC) (method) |
|---|---|---|---|
| 14.2 | 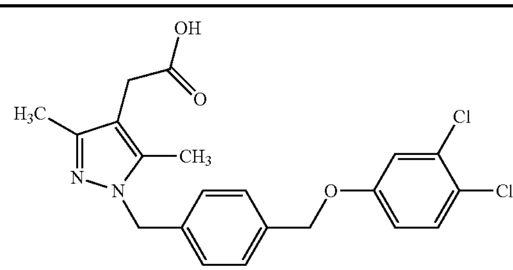 | 419/421/423 (C12) $(M+H)^+$ | 8.22 min method E |
| 14.3 | 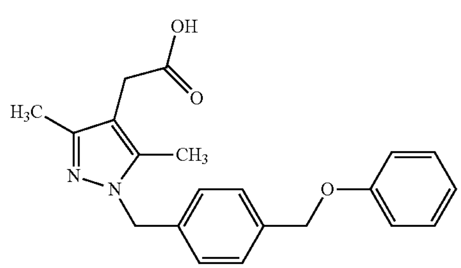 [SMILES: Cc1nn(Cc2ccc(COc3ccccc3)cc2)c(C)c1CC(=O)O] | 351 $(M+H)^+$ | 6.72 min method E |

Example 14.4

(1-{4-[1-(3,4-Dichloro-phenoxy)-ethyl]-benzyl}-3,5-dimethyl-1H-pyrazol-4-yl)-acetic acid

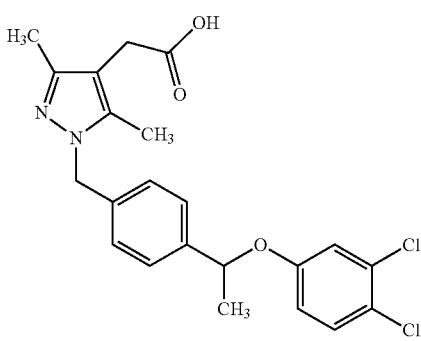 [SMILES: Cc1nn(Cc2ccc(C(C)Oc3ccc(Cl)c(Cl)c3)cc2)c(C)c1CC(=O)O]

Intermediate 14.4.1

4-(1-Bromo-ethyl)-benzoic acid methyl ester

A solution of 4-(1-bromo-ethyl)-benzoic acid (2.70 g, 11.8 mmol) in diethyl ether (20 mL) and methanol (5 mL) was cooled to 0° C. and treated with trimethylsilyldiazomethane (2 M in diethylether, 11.8 mL). After 1 h at 0° C. the solvents were removed under reduced pressure, the residue was re-dissolved in ethyl acetate (20 mL) and washed with aqueous NaHCO$_3$ solution. The organic layer was collected, dried over MgSO$_4$ and evaporated under reduced pressure.
Yield: 3.0 g
ESI mass spectrum: $[M+H]^+$=243/245 (Br)
Retention time HPLC: 2.80 min (method F)

Intermediate 14.4.2

4-[1-(3,4-Dichloro-phenoxy)-ethyl]-benzoic acid methyl ester

A mixture of 4-(1-bromo-ethyl)-benzoic acid methyl ester (intermediate 14.4.1, 0.5 g, 2.05 mmol), 3,4-dichlorophenol (0.34 g, 2.1 mmol) and Cs$_2$CO$_3$ (0.34 g, 1.0 mmol) in dimethylformamide (5 mL) was stirred at room temperature for 12 h and at 50° C. for additional 6 h. The reaction mixture was poured into water and extracted twice with diethyl ether. The organic layer was separated, dried over MgSO$_4$ and evaporated under reduced pressure.
Yield: 480 mg
ESI mass spectrum: $[M+H]^+$=325/327/329 (Cl$_2$)
Retention time HPLC: 3.04 min (method G)

Intermediate 14.4.3

{4-[1-(3,4-Dichloro-phenoxy)-ethyl]-phenyl}-methanol

Intermediate 14.4.3 was prepared according to the procedure of Example 13.1.2, employing intermediate 14.4.2.
Yield: 430 mg
ESI mass spectrum: $[M+H-H_2O]^+$=279/281/283 (Cl$_2$)
Retention time HPLC: 1.99 min (method G)

Intermediate 14.4.4

4-[1-(4-Bromomethyl-phenyl)-ethoxy]-1,2-dichloro-benzene

Intermediate 14.4.4 was prepared according to the procedure of Example 13.1.3, employing intermediate 14.4.3.
Yield: 500 mg
ESI mass spectrum: $[M+H]^+$=360/362/364/366 (Br, Cl$_2$)
Retention time HPLC: 2.10 min (method G)

Example 14.4

(1-{4-[1-(3,4-Dichloro-phenoxy)-ethyl]-benzyl}-3,5-dimethyl-1H-pyrazol-4-yl)-acetic acid Example 14.4 was prepared according to the procedure of Example 13.1, employing in the alkylation reaction intermediate 14.4.4 instead of 13.1.3. Purification was performed via preparative reversed phase HPLC (gradient of acetonitrile in water+0.1% trifluoroacetic acid).

Yield: 7 mg
ESI mass spectrum: $[M+H]^+$=433/435/437 (Cl2)
Retention time HPLC: 8.72 min (method E)

The following examples were prepared according to the method described for example 14.4, employing in the alkylation reaction the corresponding bromomethyl-phenyl derivatives instead of intermediate 14.4.4.

| Example | Structure | m/z (ESI-MS) | R$_t$ (HPLC) (method) |
|---|---|---|---|
| 14.5 | (pyrazole-acetic acid with 4-[1-(4-trifluoromethyl-phenoxy)-ethyl]-benzyl substituent) | 433 (M + H)$^+$ | 8.32 min method E |

| Example | Structure | m/z (ESI-MS) | $R_t$ (HPLC) (method) |
|---|---|---|---|
| 14.6 | 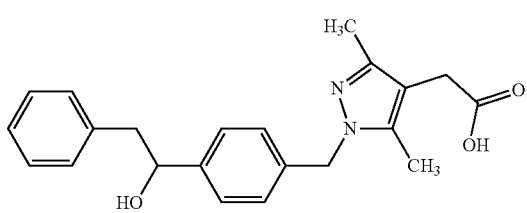 [SMILES: Cc1nn(Cc2ccc(C(O)Cc3ccccc3)cc2)c(C)c1CC(=O)O] | 365 (M + H)+ | 7.00 min method E |

Example 15.1

{1-[4-(1-Hydroxy-2-phenyl-ethyl)-benzyl]-3,5-dimethyl-1H-pyrazol-4-yl}-acetic acid

Intermediate 15.1.1

[1-(4-Formyl-benzyl)-3,5-dimethyl-1H-pyrazol-4-yl]-acetic acid methyl ester (3,5-Dimethyl-1H-pyrazol-4-yl)-acetic acid methyl ester (1 g, 6.0 mmol), 4-(bromomethyl)-benzaldehyde (1.18 g, 6.0 mmol) and $K_2CO_3$ (1.73 g, 12.5 mmol) were refluxed in 5 ml acetonitrile for 12 h. After cooling, the mixture was filtered, and the solvent was removed under reduced pressure. The residue was purified by MPLC (silica gel, $CH_2Cl_2$/methanol 99:1).

Yield: 1.6 g

ESI mass spectrum: [M+H]+=287

Intermediate 15.1.2

{1-[4-(1-Hydroxy-2-phenyl-ethyl)-benzyl]-3,5-dimethyl-1H-pyrazol-4-yl}-acetic acid methyl ester

[1-(4-Formyl-benzyl)-3,5-dimethyl-1H-pyrazol-4-yl]-acetic acid methyl ester (intermediate 15.1.1, 500 mg, 1.8 mmol) was dissolved in 5 ml tetrahydrofuran, cooled to −78° C., and benzyl magnesium chloride (1.92 ml, 2 M solution in tetrahydrofuran) was added to the solution. After 30 min at this temperature, the mixture was warmed to room temperature within 12 h, and ice and 4 N aqueous HCl was added to the solution. After dilution with ethyl acetate, the organic layer was separated and the aqueous layer was extracted twice with ethyl acetate. The combined organic layer was dried over $MgSO_4$ and the solvent was removed under reduced pressure.

The residue was purified by MPLC (silica gel, $CH_2Cl_2$/methanol 98:2).

Yield: 0.21 g

ESI mass spectrum: [M+H]+=379

Example 15.1

{1-[4-(1-Hydroxy-2-phenyl-ethyl)-benzyl]-3,5-dimethyl-1H-pyrazol-4-yl}-acetic acid {1-[4-(1-Hydroxy-2-phenyl-ethyl)-benzyl]-3,5-dimethyl-1H-pyrazol-4-yl}-acetic acid methyl ester (intermediate 15.1.2, 110 mg, 0.29 mmol) was dissolved in 3 ml dioxane and aqueous NaOH solution (0.58 ml, 1 M) was added. After stirring for 2.5 h at 60° C. and dilution with water, aqueous HCl solution (0.61 ml, 1 M) was added. The mixture was extracted with ethyl acetate, and the organic layer was dried with $MgSO_4$ and evaporated under reduced pressure. The residue was lyophilized.

Yield: 76 mg

ESI mass spectrum: [M+H]+=365

Retention time HPLC: 1.23 min (method D).

Example 15.2

[3,5-Dimethyl-1-(4-phenylacetyl-benzyl)-1H-pyrazol-4-yl]-acetic acid

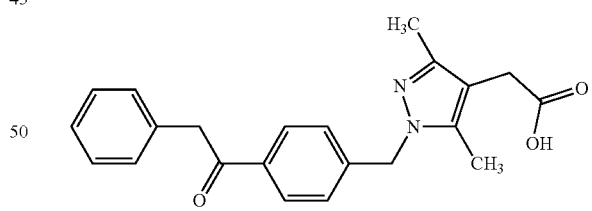

Oxidation: {1-[4-(1-Hydroxy-2-phenyl-ethyl)-benzyl]-3,5-dimethyl-1H-pyrazol-4-yl}-acetic acid methyl ester (intermediate 15.1.2, 100 mg, 0.26 mmol) was dissolved in 4 ml dichloromethane, cooled to 0° C. and Dess-Martin periodinane (135 mg, 0.32 mmol) was added to the solution. After warming to room temperature, the mixture was stirred for 3 h. The solvent was evaporated under reduced pressure. Saponification: The ester intermediate (70 mg, 0.19 mmol) was dissolved in 2 ml dioxane and aqueous NaOH solution (0.37 ml, 1 M). After stirring for 2.5 h at 60° C. and dilution with water, aqueous HCl solution (0.39 ml, 1 M) was added. The mixture was extracted with ethyl acetate, and the organic layer was dried with $MgSO_4$ and evaporated under reduced pressure. The residue was purified by preparative reversed phase HPLC (gradient of methanol in water+0.1% NH3).
Yield: 13 mg
ESI mass spectrum: [M+H]$^+$=363
Retention time HPLC: 1.28 min (method D).

Example 16.1

{3,5-Dimethyl-1-[4-(4-trifluoromethyl-phenylsulfa-nylmethyl)-benzyl]-1H-pyrazol-4-yl}-acetic acid

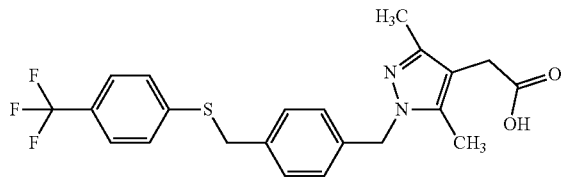 [SMILES: Cc1nn(Cc2ccc(CSc3ccc(C(F)(F)F)cc3)cc2)c(C)c1CC(=O)O]

Intermediate 16.1.1

[1-(4-Hydroxymethyl-benzyl)-3,5-dimethyl-1H-pyrazol-4-yl]-acetic acid methyl ester (3,5-dimethyl-1H-pyrazol-4-yl)-acetic acid methyl ester (3 g, 18 mmol), 4-(chloromethyl)benzyl alcohol (3.59 g, 18 mmol) and K$_2$CO$_3$ (5.18 g, 37 mmol) were refluxed in 10 ml acetonitrile for 3 h. After cooling, the mixture was filtered, and the solvent was removed under reduced pressure. The residue was purified by MPLC (silica gel, CH$_2$Cl$_2$/methanol 9:1).
Yield: 4.8 g
ESI mass spectrum: [M+H]$^+$=289

Intermediate 16.1.2

[1-(4-Chloromethyl-benzyl)-3,5-dimethyl-1H-pyrazol-4-yl]-acetic acid methyl ester

[1-(4-Hydroxymethyl-benzyl)-3,5-dimethyl-1H-pyrazol-4-yl]-acetic acid methyl ester (intermediate 16.1.1, 4.8 g, 16.7 mmol) was dissolved in 60 ml dichloromethane. Triethylamine (3.5 ml, 25 mmol) was added, followed by dropwise addition of methanesulfonyl chloride (1.29 ml, 16.7 mmol). After 12 h at room temperature, the mixture was washed with water, aqueous KHSO$_4$ solution, water, aqueous NaHCO$_3$ solution and with water. The organic layer was dried over MgSO4 and the solvent was evaporated under reduced pressure.
Yield: 3.7 g crude Intermediate 16.1.3

{3,5-Dimethyl-1-[4-(4-trifluoromethyl-phenylsulfa-nylmethyl)-benzyl]-1H-pyrazol-4-yl}-acetic acid methyl ester 4-(Trifluoromethyl)thiophenol (0.25 ml, 1.8 mmol) was dissolved in 5 ml dimethylformamide, and K$_2$CO$_3$ (337 mg, 2.4 mmol) was added to the solution. A solution of [1-(4-chloromethyl-benzyl)-3,5-dimethyl-1H-pyrazol-4-yl]-acetic acid methyl ester (intermediate 16.1.2, 1 g, 1.6 mmol) in dimethylformamide was added to the mixture within 5 min, and the mixture was stirred for 1 h at room temperature. Ethyl acetate and water were added, the mixture was washed with aqueous NaOH solution (1 M) and with water. The organic layer was dried over MgSO$_4$ and the solvent was evaporated under reduced pressure. The residue was purified by MPLC (silica gel, CH$_2$Cl$_2$/methanol 99:1) and preparative reversed phase HPLC (gradient of methanol in water+0.1% NH$_3$).
Yield: 0.26 g
ESI mass spectrum: [M+H]$^+$=449

Example 16.1

{3,5-Dimethyl-1-[4-(4-trifluoromethyl-phenylsulfa-nylmethyl)-benzyl]-1H-pyrazol-4-yl}-acetic acid {3,5-Dimethyl-1-[4-(4-trifluoromethyl-phenylsulfanylmethyl)-benzyl]-1H-pyrazol-4-yl}-acetic acid methyl ester (intermediate 16.1.3, 80 mg, 0.18 mmol) was dissolved in 2 ml dioxane and aqueous NaOH solution (0.36 ml, 1 M) was added. After stirring for 2.5 h at 60° C. and dilution with water, aqueous HCl solution (0.37 ml, 1 M) was added. The product was isolated by filtration, washed with water and dried under reduced pressure.
Yield: 56 mg
ESI mass spectrum: [M+H]$^+$=435
Retention time HPLC: 1.51 min (method D).

Example 16.2

{3,5-Dimethyl-1-[4-(4-trifluoromethyl-benzenesulfi-nylmethyl)-benzyl]-1H-pyrazol-4-yl}-acetic acid

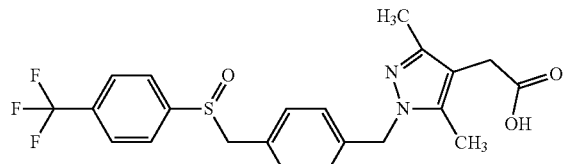

Intermediate 16.2.1

{3,5-Dimethyl-1-[4-(4-trifluoromethyl-benzenesulfi-nylmethyl)-benzyl]-1H-pyrazol-4-yl}-acetic acid methyl ester {3,5-Dimethyl-1-[4-(4-trifluoromethyl-phenylsulfanylmethyl)-benzyl]-1H-pyrazol-4-yl}-acetic acid methyl ester (intermediate 16.1.3, 170 mg, 0.38 mmol) was dissolved in 3 ml dichloromethane and 3-chloroperbenzoic acid (79 mg, 0.45 mmol) was added at 5° C. After 1 h at that temperature, the mixture was diluted with dichloromethane and washed with aqueous NaHCO$_3$ solution. The organic layer was dried over MgSO$_4$ and the solvent was evaporated under reduced pressure.
Yield: 120 mg
ESI mass spectrum: [M+H]$^+$=465

Example 16.2

{3,5-Dimethyl-1-[4-(4-trifluoromethyl-benzenesulfi-nylmethyl)-benzyl]-1H-pyrazol-4-yl}-acetic acid {3,5-Dimethyl-1-[4-(4-trifluoromethyl-benzenesulfinyl-methyl)-benzyl]-1H-pyrazol-4-yl}-acetic acid methyl ester (intermediate 16.2.1, 60 mg, 0.13 mmol) was dissolved in 2 ml dioxane and 1 ml water and aqueous NaOH solution (0.26 ml, 1 M) was added. After stirring for 1 h at 60° C. and dilution with water, aqueous HCl solution (0.39 ml, 1 M) was added. The mixture was extracted twice with ethyl acetate, the organic layer was dried over MgSO$_4$ and evaporated under reduced pressure.

Yield: 52 mg
ESI mass spectrum: [MA-H]$^+$=451
Retention time HPLC: 1.25 min (method D).

Example 16.3

{3,5-Dimethyl-1-[4-(4-trifluoromethyl-benzene-sulfonylmethyl)-benzyl]-1H-pyrazol-4-yl}-acetic acid

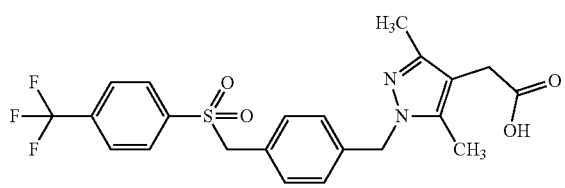 [SMILES: Cc1nn(Cc2ccc(CS(=O)(=O)c3ccc(C(F)(F)F)cc3)cc2)c(C)c1CC(=O)O]

Oxidation: {3,5-Dimethyl-1-[4-(4-trifluoromethyl-benzenesulfinylmethyl)-benzyl]-1H-pyrazol-4-yl}-acetic acid methyl ester (intermediate 16.2.1, 60 mg, 0.13 mmol) was dissolved in 3 ml dichloromethane and 3-chloroperbenzoic acid (26.8 mg, 0.16 mmol) was added at 5° C. After 1 h at that temperature, the mixture was diluted with dichloromethane and washed with aqueous NaHCO$_3$ solution. The organic layer was dried over MgSO$_4$ and evaporated under reduced pressure. Saponification: The ester intermediate (50 mg, 0.1 mmol) was dissolved in 2 ml dioxane and 1 ml water and aqueous NaOH solution (0.37 ml, 1 M) was added. After stirring for 1 h at 60° C. and dilution with water, aqueous HCl solution (0.65 ml, 1 M) was added. The precipitate was filtered off, washed with water and dried under reduced pressure.

Yield: 35 mg
ESI mass spectrum: [M+H]$^+$=467
Retention time HPLC: 1.25 min (method D).

The following examples 16.4, 16.5, 16.6 were prepared according to the methods described for examples 16.1, 16.2, 16.3 and the corresponding intermediates using 3,4-dichlorothiophenol as starting material.

Example 16.4

{1-[4-(3,4-Dichloro-phenylsulfanylmethyl)-benzyl]-3,5-dimethyl-1H-pyrazol-4-yl}-acetic acid

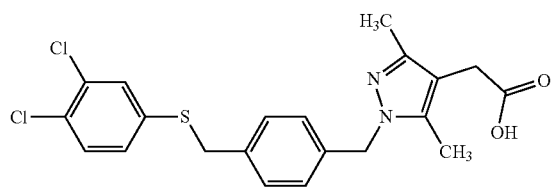 [SMILES: Cc1nn(Cc2ccc(CSc3ccc(Cl)c(Cl)c3)cc2)c(C)c1CC(=O)O]

ESI mass spectrum: [M+H]$^+$=435/437/439
Retention time HPLC: 1.57 min (method D).

Example 16.5

{1-[4-(3,4-Dichloro-benzenesulfinylmethyl)-benzyl]-3,5-dimethyl-1H-pyrazol-4-yl}-acetic acid

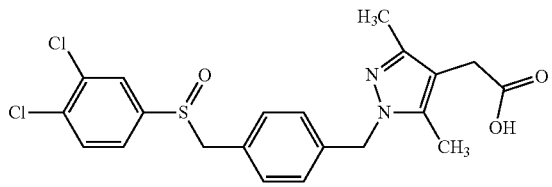 [SMILES: Cc1nn(Cc2ccc(CS(=O)c3ccc(Cl)c(Cl)c3)cc2)c(C)c1CC(=O)O]

ESI mass spectrum: [M+H]$^+$=451/453/455
Retention time HPLC: 1.30 min (method D).

Example 16.6

{1-[4-(3,4-Dichloro-benzenesulfonylmethyl)-benzyl]-3,5-dimethyl-1H-pyrazol-4-yl}-acetic acid

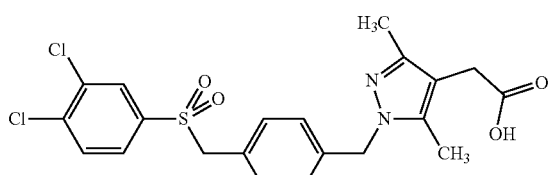

ESI mass spectrum: [M+H]$^+$=467/469/471
Retention time HPLC: 1.31 min (method D).

Synthesis Example 17.1-17.2

Intermediate 17.1.1

{1-[1-(4-Bromo-phenyl)-ethyl]-3,5-diethyl-1H-pyrazol-4-yl}-acetic acid ethyl ester To a solution of 4-oxo-3-propionyl-hexanoic acid ethyl ester (500 mg) (preparation analagous to that of 1,1-dimethylethyl 4-oxo-3-propanoylhexanoate in WO2007/141267) in methanol (20 ml) at room temperature was added [1-(4-bromo-phenyl)-ethyl]-hydrazine (0.75 g). After overnight stirring, water was added and the mixture extracted 3 times with ethyl acetate. The organic layer was separated; washed with water and brine solution, then dried and concentrated to afford 792 mg of the title compound. Retention time HPLC: 1.58 min (Method D), ESI mass spectrum: (Br) [M]$^+$=393/395.

Example 17.1

To a degassed, stirred solution of intermediate 17.1.1 (200 mg) in toluene (2 ml) was added 4-trifluoromethylbenzamide (0.15 g), K$_3$PO$_4$ (248 mg), N,N'-dimethyl-cyclohexane-1,2-diamine (11 mg), copper iodide (15 mg) and the reaction heated to 100° C. After 3 days, the reaction was cooled to room temperature, water was added and the mixture was extracted 3 times with ethyl acetate. The organic layer was separated; washed with water and brine solution, then dried and concentrated to afford 140 mg of the title compound.

Retention time HPLC: 1.54 min (Method D), ESI mass spectrum: [M+H]$^+$=502. Saponification: A solution of the ester intermediate in methanol (5 mL) was treated with aqueous NaOH solution (4 M, 0.5 mL). After 18 h, the reaction mixture was neutralized, the volatiles were removed under reduced pressure and the remaining residue was purified via preparative reversed phase HPLC (gradient of methanol in water+0.1% NH$_3$). Yield: 46 mg.

| Example | Structure | m/z (ESI-MS) | R$_t$ (HPLC) (method) |
|---|---|---|---|
| 17.1 | [structure] | 474 | 1.09 min Method J |
| 17.2 | [structure] | 474 | 1.16 min Method J | ture was neutralized, the volatiles were removed under reduced pressure and the remaining residue was purified via preparative reversed phase HPLC (gradient of methanol in water+0.1% NH$_3$). Yield: 46 mg.

Intermediate 17.2.1

4-[1-(4-Ethoxycarbonylmethyl-3,5-diethyl-pyrazol-1-yl)-ethyl]-benzoic acid

To a solution of intermediate 17.1.1 (200 mg) in dioxane (0.35 ml) in a microwave vial was added molybdenum hexacarbonyl complex (68 mg), Herrmann's catalyst (25 mg), diisopropylamide (175 µl) and water (0.73 ml). The mixture was heated in the microwave reactor at 130° C. for 30 min. After cooling to room temperature, water was added and the suspension filtered. The filtrate was concentrated and purified over reversed phase HPLC (gradient of acetonitrile in methanol in water+0.13% TFA) to afford 123 mg of the title compound.

Example 17.2

To a stirred solution of intermediate 17.2.1. (123 mg) in DMF (5 ml) at room temperature was added diisopropylethylamine (0.15 ml) and TBTU (0.22 g). After 20 min, p-trifluoroaniline (0.061 g) was added and the reaction stirred overnight. Water was added and the mixture extracted 3 times with ethyl acetate. The organic layer was separated; washed with water and brine solution, then dried and concentrated. The residue was purified over normal phase MPLC (gradient of EtOAc in cyclohexane) to afford 145 mg of the title compound. Retention time HPLC: 1.58 min (Method D), ESI mass spectrum: [M+H]$^+$=502. Saponification: A solution of the ester intermediate in methanol (5 mL) was treated with aqueous NaOH solution (4 M, 0.6 mL). After 18 h, the reaction mixture was neutralized, the volatiles were removed under reduced pressure and the remaining residue was purified via preparative reversed phase HPLC (gradient of methanol in water+0.1% NH$_3$). Yield: 46 mg.

Synthesis Example 18.1

Intermediate 18.1.1

5-Bromo-2-(tert-butyl-dimethyl-silanyloxymethyl)-pyridine

To a stirred solution of (5-bromo-pyridin-2-yl)-methanol (500 mg) in DMF (2 ml) at room temperature, was added tert-butyl-chloro-dimethyl-silane (0.48 g) and imidazole (0.36 g). After overnight stirring, ethyl acetate was added followed by water and mixture extracted 3 times with ethyl acetate. The organic layer was separated; washed with water and brine solution, then dried and concentrated to afford 800 mg of the title compound. ESI mass spectrum: [M]$^+$=302.

Intermediate 18.1.2

N-[6-(tert-Butyl-dimethyl-silanyloxymethyl)-pyridin-3-yl]-3,4-dichloro-benzamide To a degassed, stirred solution of intermediate 18.1.1 (2 g) in toluene (5 ml) was added 3,4-dichloro-benzamide (1.51 g), N,N'-dimethyl-cyclohexane-1,2-diamine (141 mg), K$_3$PO$_4$ (3.2 g) and copper iodide (189 mg) and the reaction heated to 100° C. overnight. The reaction was allowed to cool to room temperature and water was added. This was extracted with ethyl acetate 3 times and the organic layer was separated; washed with water and brine solution, then dried and concentrated. The residue was purified over normal phase MPLC (gradient of ethyl acetate in cyclohexane) to afford 1.34 g of the title compound. Retention time HPLC: 1.64 min (Method K), ESI mass spectrum: [M]$^+$=411.

Intermediate 18.1.3

3,4-Dichloro-N-(6-hydroxymethyl-pyridin-3-yl)-benzamide

To a stirred solution of intermediate 18.1.2 (0.34 g) in tetrahydrofurane (5 ml) at room temperature was added tetrabutyl-ammonium fluoride (1.24 ml) dropwise. After overnight stirring, water was added. This was extracted with ethyl acetate 3 times and the organic layer was separated; washed with water and brine solution, then dried and concentrated to afford 1.17 g of the title compound. Retention time HPLC: 1.34 min (Method K), ESI mass spectrum: $[M]^+=297$.

Intermediate 18.1.4

3,4-Dichloro-N-(6-chloromethyl-pyridin-3-yl)-benzamide

To a solution of intermediate 18.1.3 (200 mg) in $CH_3CN$ (5 ml) at room temperature was added thionyl chloride (0.15 ml) and DMF (few drops) and the reaction stirred overnight.

Ice/water was carefully added and the reaction extracted with ethyl acetate 3 times. The organic layer was separated; washed with water and brine solution, then dried and concentrated. The residue was purified over normal phase MPLC (gradient of ethyl acetate in cyclohexane) to afford 209 mg of the title compound. Retention time HPLC: 1.40 min (Method P), ESI mass spectrum: $[M]^+=315$.

Example 18.1

To a solution of (3,5-dimethyl-1H-pyrazol-4-yl)-acetic acid tert-butyl ester (150 mg) (preparation according to WO2007/141267) in DMF (2 ml) in a microwave vial was added intermediate 18.1.4 (248 mg), $K_2CO_3$ (148 mg) and a few crystals of sodium iodide. This was heated at 100° C. in a microwave reactor for 1 h. The reaction was allowed to cool to rt, water was added and the reaction extracted with ethyl acetate 3 times. The organic layer was separated; washed with water and brine solution, then dried and concentrated. The residue was purified over normal phase MPLC (gradient of ethyl acetate in cyclohexane) to afford 176 mg of a solid. Retention time HPLC: 1.40 min (Method K), ESI mass spectrum: $[M]^+=1.52$. Hydrolysis: a solution of the ester intermediate in DCM (5 mL) was treated with TFA (0.44 mL). After 18 h, water was added to the reaction mixture and this extracted 3 times with dichloromethane. The organic layer was separated, dried and concentrated. The residue was triturated with diethylether to afford 24 mg of the title compound.

Synthesis Examples 19.1-19.4

Intermediate 19.1.1

Naphthalen-2-yl-methanethiol

To a stirred solution of 2-(bromomethyl)naphthalene (10 g) in ethanol (40 ml) was added thiourea (3.79 g) and the reaction heated to reflux. After 6 h, the reaction was cooled in an ice bath, the precipitate was filtered off and washed with ice-cold ethanol. This was then added to NaOH solution (25%, 30 ml) and heated to reflux. After 2 h, the reaction was cooled to room temperature and water (200 ml) was added. The mixture was extracted with diethylether 3 times, the organic phase was separated, dried and concentrated to afford 5 g of the title compound.

ESI mass spectrum: $[M-H]^-=173$.

Intermediate 19.1.2

[1-(4-Bromo-benzyl)-3,5-dimethyl-1H-pyrazol-4-yl]-acetic acid methyl ester

To a solution of (3,5-dimethyl-1H-pyrazol-4-yl)-acetic acid methyl ester (30.7 g) (preparation according to WO2007/141267) in $CH_3CN$ (500 ml) was added $K_2CO_3$ (43.5 g) and 4-bromobenzylbromide (38.6 g) and the reaction heated to reflux. After 15 h, the reaction was cooled and filtered, the filtrate was then concentrated. The residue was recrystallized from cyclohexane to afford 37.3 g of the title compound.

Intermediate 19.1.3

{3,5-Dimethyl-1-[4-(naphthalen-2-ylmethylsulfanyl)-benzyl]-1H-pyrazol-4-yl}-acetic acid

To a solution of intermediate 19.1.2 (5.4 g) in NMP (2 ml) in a microwave vial was added intermediate 19.1.1 (2.8 g) and sodium methoxide (1.7 g). This was heated at 220° C. in a microwave reactor for 3 h. The reaction was allowed to cool to room temperature, water was added and the reaction neutralized with glacial acetic acid. The precipitate was filtered off and the solid washed with acetone and diisopropylether. The filtrate was concentrated to give 170 mg of the title compound. Retention time HPLC: 1.52 min (Method D), ESI mass spectrum: $[M+H]^+=417$.

| Example | Structure | m/z (ESI-MS) | $R_t$ (HPLC) (method) |
|---|---|---|---|
| 18.1 | (structure) | 433 | 1.09 min Method K |

Example 19.1

To a stirred solution of intermediate 19.1.3 (170 mg) in dichloromethane (10 ml) at 0° C. was added m-chloroperbenzoic acid (77 mg). After 2 h, the reaction was concentrated and the residue purified by HPLC (Method Q). This afforded 10 mg of the title compound.

Examples 19.2-19.4 were prepared in analogous fashion to example 19.1, preparing the required arylmethanethiols from the corresponding bromides and employing 3,5-diethyl-1H-pyrazol-4-yl)-acetic acid methyl ester instead of 3,5-dimethyl-1H-pyrazol-4-yl)-acetic acid methyl ester in the case of examples 19.3 and 19.4.

| Example | Structure | m/z (ESI-MS) | $R_t$ (HPLC) (method) |
|---|---|---|---|
| 19.1 | 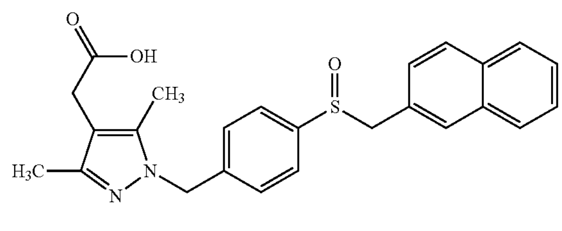 [SMILES: Cc1nn(Cc2ccc(S(=O)Cc3ccc4ccccc4c3)cc2)c(C)c1CC(=O)O] | 433 | 0.93 min Method J |
| 19.2 | 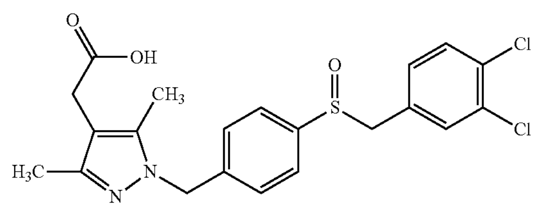 [SMILES: Cc1nn(Cc2ccc(S(=O)Cc3ccc(Cl)c(Cl)c3)cc2)c(C)c1CC(=O)O] | 451 | 0.93 min Method J |
| 19.3 | 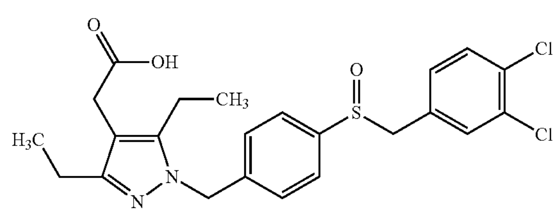 [SMILES: CCc1nn(Cc2ccc(S(=O)Cc3ccc(Cl)c(Cl)c3)cc2)c(CC)c1CC(=O)O] | 479 | 1.01 min Method J |
| 19.4 | 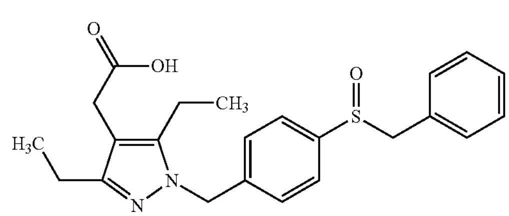 [SMILES: CCc1nn(Cc2ccc(S(=O)Cc3ccccc3)cc2)c(CC)c1CC(=O)O] | 411 | 0.88 min Method J |

HPLC-methods:

Method A:

HPLC-MS: Waters ZMD, Alliance 2790/2695 HPLC, Waters 2996 diode array detector

Mobile Phase:

A: water with 0.1% trifluoroacetic acid

B: methanol with 0.1% trifluoroacetic acid

| time in min | % A | % B | flow rate in ml/min |
|---|---|---|---|
| 0.00 | 95 | 5 | 1.50 |
| 2.00 | 0 | 100 | 1.50 |
| 2.50 | 0 | 100 | 1.50 |
| 2.60 | 95 | 5 | 1.50 |
| 2.90 | 95 | 5 | 1.50 |

Column: Waters Sunfire C 18, 3.5 μm, 4.6×50 mm (column temperature: constant at 40° C.).

Detection by diode array detector at 210-500 nm wavelength.

Method B:

HPLC-MS: Agilent 1100

Mobile Phase:

A: water with 0.032% $NH_4OH$

B: methanol

| time in min | % A | % B | flow rate in ml/min |
|---|---|---|---|
| 0.00 | 95 | 5 | 1.50 |
| 2.00 | 0 | 100 | 1.50 |
| 2.50 | 0 | 100 | 1.50 |
| 2.60 | 95 | 5 | 1.50 |
| 2.90 | 95 | 5 | 1.50 |

Column: XBridge C18, 3.5 μm, 4.6×50 mm (column temperature: constant at 40° C.).

Detection by diode array detector at 210-500 nm wavelength.

Method C:

HPLC-MS-1 and HPLC-MS-2:

Waters ZQ MS, Alliance 2690/2695 HPLC, Waters 996/2996 diode array detector

Mobile Phase:

A: water with 0.10% $NH_3$

B: methanol

| time in min | % A | % B | flow rate in ml/min |
|---|---|---|---|
| 0.00 | 95 | 5 | 4.00 |
| 0.20 | 95 | 5 | 4.00 |
| 1.60 | 0 | 100 | 4.00 |
| 1.90 | 0 | 100 | 4.00 |
| 2.00 | 0 | 100 | 0.30 |

Column: Waters XBridge™ C18 3.5 μm, 4.6×20 mm IS™ (column temperature: constant at 40° C.).

Detection by diode array detector at 210-400 nm wavelength.

Method D

HPLC-MS-1 and HPLC-MS-2:

Waters ZQ MS, Alliance 2690/2695 HPLC, Waters 996/2996 diode array detector

Mobile Phase:

A: water with 0.10% trifluoroacetic acid

B: methanol

| time in min | % A | % B | flow rate in ml/min |
|---|---|---|---|
| 0.00 | 95 | 5 | 4.00 |
| 0.20 | 95 | 5 | 4.00 |
| 1.60 | 0 | 100 | 4.00 |
| 2.10 | 0 | 100 | 4.00 |

Column: Waters XBridge™ C18 3.5 μm, 4.6×20 mm IS™ (column temperature: constant at 40° C.).

Detection by diode array detector at 210-400 nm wavelength.

Method E

Instrument: LC/MS ThermoFinnigan HPLC Surveyor DAD, MSQ single quadrupole

Column: Synergi Hydro RP80A, 4 μm, 4.6×100 mm

Mobile phase: A=90% $H_2O$+10% $H_3CCN$+$NH_4COOH$ 10 mM

B=90% $H_3CCN$+10% $H_2O$+$NH_4COOH$ 10 mM

Flow rate: 1200 μL/min

Gradient: A (100%) for 1.5 min. then to B (100%) in 10 min, hold for 3 min.

Detection: UV, 254 nm

Detection: Finnigan MSQ, quadrupole

Ion source: APCl

Scan range: 110-900

Method F

Instrument: LC/MS Waters. Hplc Alliance 2695 DAD, ZQ Quadrupole.

Column: Gemini C18, 3 μm, 4.6×50 mm

Mobile phase: A=90% $H_2O$+0.1% $F_3CCO_2H$+10% $H_3CCN$

B=$H_3CCN$

Flow rate: 1300 μL/min

Gradient: A/B (70:30), then to A/B (10:90) in 3.50 minutes, hold for 1 minute

Detection: UV, 254 nm

Detection: Waters ZQ, Quadrupole

Ion source: ESI

Scan range: 120-900

Method G

Instrument: LC/MS Waters. Hplc Alliance 2695 DAD, ZQ Quadrupole.

Column: Gemini C18, 3 μm, 4.6×50 mm

Mobile phase: A=90% $H_2O$+0.1% $F_3CCO_2H$+10% $H_3CCN$

B=$H_3CCN$

Flow rate: 1300 μL/min

Gradient: A/B (50:50), then to A/B (10:90) in 3.50 minutes, hold for 1 minute

Detection: UV, 254 nm

Detection: Waters ZQ, Quadrupole

Ion source: ESI

Scan range: 120-900

Method H

Instrument: LC/MS Waters Acquity SQD HPLC System.

Column: BEH C18, 1.7 um, 2.1×50 mm

Mobile phase: A=90% $H_2O$+0.1% $F_3CCO_2H$+10% $H_3CCN$

B=$H_3CCN$

Flow rate: 480 pt/min

Gradient: A/B (70:30), then to NB (10:90) in 1.2 minutes, hold for 0.46 minutes

Detection: UV, 254 nm
Detection: Waters SQD, Quadrupole
  Ion source: ESI
  Scan range: 120-900
HPLC Method J
HPLC-MS: Waters LCTclassic MS, Agilent HP1200, Waters 2996 diode array detector
Column: Supelco Ascentis Express C18_2.1×30 mm, 2.7 µm (column temperature: constant at 60° C.).
Mobile Phase: A: acetonitrile with 0.08% trifluoroacetic acid
  B: water with 0.1% trifluoroacetic acid

| time in min | % A | % B | flow rate in ml/min |
|---|---|---|---|
| 0.00 | 2 | 98 | 1.50 |
| 0.20 | 2 | 98 | 1.50 |
| 1.70 | 100 | 0 | 1.50 |
| 1.90 | 100 | 0 | 1.50 |
| 2.00 | 2 | 98 | 1.50 |

Detection by diode array detector at 210-500 nm wavelength.
HPLC Method K
HPLC-MS: Waters 2695 HPLC, ZQ MS, 2996 diode array detector, 2695 autosampler
Column: Waters XBridge C18, 4.6×30 mm, 3.5 µm (column temperature: constant at 60° C.).
Mobile Phase: A: water with 0.1% $NH_3$
  B: methanol with 0.1% $NH_3$

| time in min | % A | % B | flow rate in ml/min |
|---|---|---|---|
| 0.00 | 95 | 5 | 4.0 |
| 0.20 | 95 | 5 | 4.0 |
| 1.50 | 0 | 100 | 4.0 |
| 1.75 | 0 | 100 | 4.0 |

Detection by diode array detector at 210-400 nm wavelength.
HPLC Method L
HPLC-MS: Agilent 1200 HPLC, 6140 Quadropole MS, 1200 diode array detector
Column: Waters XBridge C18, 3.0×30 mm, 2.5 µm (column temperature: constant at 40° C.).
Mobile Phase: A: water with 0.2% $NH_3$
  B: methanol with 3% water

| time in min | % A | % B | flow rate in ml/min |
|---|---|---|---|
| 0.00 | 95 | 5 | 1.3 |
| 0.20 | 95 | 5 | 1.3 |
| 2.20 | 5 | 95 | 1.3 |
| 2.30 | 5 | 95 | 1.3 |
| 2.40 | 0 | 100 | 1.3 |
| 2.60 | 0 | 100 | 1.3 |

Detection by diode array detector at 210-500 nm wavelength.
HPLC Method M
HPLC: Acquity HPLC/MS Waters, Waters PDA (total scan), Waters ELSD, Waters SQD
Column: Acquity HPLC BEH C18, 1.7 um, 2.1×50 mm
Ion source: ESI Mobile phase: A=($NH_4COOH$ 5 mM)+10% $CH_3CN$
  B=$CH_3CN$+10% water
Flow rate: 700 µL/min
Gradient: from A/B (100/0%) to NB (0/100%) in 2.4 min, then NB (0/100%)) for 0.3 min
HPLC Method N
HPLC: Waters Acquity, MS: SOD
Column: XBridge BEH C18, 2.1×30 mm, 1.7 µm (column temperature: constant at 60° C.).
Mobile Phase: A: water with 0.13% trifluoroacetic acid
  B: methanol with 0.08% TFA

| time in min | % A | % B | flow rate in ml/min |
|---|---|---|---|
| 0.00 | 99 | 1 | 1.3 |
| 0.05 | 99 | 1 | 1.3 |
| 0.35 | 0 | 100 | 1.3 |
| 0.50 | 0 | 100 | 1.3 |

HPLC Method P
HPLC: Waters Alliance, MS: ZQ
Column: Waters XBridge C18, 4.6×30 mm, 3.5 µm (column temperature: constant at 60° C.).
Mobile Phase: A: water with 0.1% trifluoro acetic acid
  B: methanol with 0.1% trifluoro acetic acid

| time in min | % A | % B | flow rate in ml/min |
|---|---|---|---|
| 0.00 | 95 | 5 | 4.0 |
| 0.20 | 95 | 5 | 4.0 |
| 1.50 | 0 | 100 | 4.0 |
| 1.90 | 0 | 100 | 4.0 |
| 2.00 | 95 | 5 | 4.0 |

HPLC Method Q
Preparative HPLC-MS Gilson
Column: Septech 100 g.
Mobile Phase: A: water with 0.13% trifluoro acetic acid
  B: methanol

| time in min | % A | % B | flow rate in ml/min |
|---|---|---|---|
| 0.00 | 95 | 5 | 80.0 |
| 1.30 | 95 | 5 | 165.0 |
| 8.90 | 2 | 98 | 165.0 |
| 10.00 | 2 | 98 | 165.0 |
| 10.50 | 95 | 5 | 165.0 |
| 11.80 | 95 | 5 | 165.0 |

Biological Assays
The compounds of formula (I) according to the invention were tested using the following biological test methods to determine their ability to displace $PGD_2$ from the CRTH2 receptor and for their ability to antagonise the functional effects of $PGD_2$ at the CRTH2 receptor in a whole system.
Preparation of Human CRTH2 Receptor Membranes and Radioligand Binding Assay
The binding of CRTH2 antagonists is determined using membranes prepared from Chinese hamster ovary cells (CHO-K1 cells) transfected with the human CRTH2 receptor (CHO-K1-hCRTH2 cells, Perkin Elmer, Cat No ES-561-C). To produce cell membranes the CHO-K1-hCRTH2 cells are cultured in suspension in CHO SFMII medium supplemented with 400 µg/ml G418. The cells are harvested by centrifugation at 300 g for 10 min at room temperature. The cell pellet is resuspended in Phosphate Buffer Saline (PBS) including a protease inhibitor mix (Complete, Roche) and adjusted to a concentration of 10E7 cells/ml. The CHO-K1-hCRTH2 cells are disrupted by nitrogen decomposition to obtain the membrane preparation. Cell debris is removed by centrifugation (500 g at 4° C., 30 min) and the supernatant is transferred into fresh tubes followed by a second centrifugation at 40000 g for 1 h at 4° C. to sediment the membranes. The membranes are suspended in SPA incubation buffer (50 mM Tris HCl, 10 mM $MgCl_2$, 150 mM NaCl, 1 mM EDTA, pH 7.4) without bovine serum albumin, homogenized by passing through a single use needle (Terumo, 23G×1"), and stored in aliquots at −80° C.

The CRTH2 receptor binding assay is performed in a scintillation proximity assay (SPA) format with the radioligand $[^3H]$-$PGD_2$ (Perkin Elmer, NET616000MC). CHO-K1-hCRTH2 cell membranes are again homogenized by passing through a single use needle (Terumo, 23G×1") and diluted in SPA incubation buffer in suitable concentrations (0.5-10 µg protein/well). The SPA assay is set up in 96 well microtiter plates (Perkin Elmer, CatNo. 6005040) in SPA incubation buffer with a final volume of 200 µl per well and final concentration of 50 mM Tris-HCl, 10 mM $MgCl_2$, 150 mM NaCl, 1 mM EDTA pH 7.4, 0.1% bovine serum albumin). The SPA assay mixture contains 60 µl of the membrane suspension, 80 µl of Wheat Germ Agglutinin coated PVT beads (GE Healthcare, RPNQ-0001, 0.3 mg/well), 40 µl of $[3H]$-$PGD_2$ diluted in SPA buffer to a final concentration of 1 nM (50 000 dpm) and 20 µl of the test compound (dissolved in dimethylsulfoxid). The SPA assay mixture is incubated for 3 h at room temperature. Bound radioactivity is determined with a scintillation counter (Micro Beta Trilux, Wallac).

The binding of $[^3H]$-$PGD_2$ to CHO-K1-hCRTH2 cell membranes is determined in the absence (total binding, Bo) and presence (non-specific binding, NSB) of unlabelled $PGD_2$ (1 µM, Cayman Chemical, Cat No 12010) or a reference CRTH2 antagonist (10 µM CAY10471, Cayman Chemical, Cat No 10006735).

Determination of the affinity of a test compound is calculated by subtraction of the non-specific binding (NSB) from the total binding (Bo) or the binding in the presence of the test compound (B) at a given compound concentration. The NSB value is set to 100% inhibition. The Bo-NSB value is set to 0% inhibition.

% inhibition values were obtained at a defined compound concentration, e.g. at 1 µM, inhibition of the test compound was calculated by the formula 100−((B−NSB)*100/(Bo−NSB)). % inhibition values above 100% are founded by assay variance.

The dissociation constant $K_i$ was calculated by iterative fitting of experimental data obtained at several compound concentrations over a dose range from 0.1 to 30 000 nM using the law of mass action based program "easy sys" (Schittkowski, Num Math 68, 129-142 (1994)).

CRTH2 Camp Functional Assay Protocol

The assay is conducted in CHO-K1-hCRTH2 cells. Intracellular cAMP is generated by stimulating the cells with 10 µM Forskolin, an adenylate cyclase activator. PGD2 is added to activate the CRTH2 receptor which results in the attenuation of the forskolin-induced cAMP generation. Test compounds are tested for their ability to inhibit the PGD2-mediated attenuation of the Forskolin-induced cAMP generation in CHO-K1-hCRTH2 cells. CHO-K1-hCRTH2 cells are cultured in roller bottles in CHO SFMII medium supplemented with 400 ug/ml G418. The cells are harvested by centrifugation at 300 g for 10 min at room temperature. The cell pellet is washed and suspended in PBS. The cells are adjusted to a final concentration of 4×10E6 cells/ml.

Test compounds are diluted in dimethylsulfoxid and tested at several compound concentrations over a dose range from 0.1 to 3 000 nM.

The cAMP levels are determined by an AlphaScreen cAMP assay (Perkin Elmer CatNo. 6760625M) in 384 well optiplates (PerkinElmer, CatNo. 6007290) with a total assay volume of 50 µl. 10 µl of cells (40.000 cells per well) are incubated for 30 min at 37° C. with 10 µl of a stimulation mix containing a final concentration of 10 µM Forskolin, 30 nM PGD2, 0.5 mM IBMX, 5 mM HEPES, 1×HBSS buffer, 0.1% BSA, adjusted to pH 7.4, and the test compound at various concentrations. Thereafter, 30 µl of a lysis and detection mix is added containing SA donor beads, biotinylated cAMP, anti-cAMP acceptor beads, 0.3% Tween-20, 5 mM HEPES, 0.1% BSA, adjusted to pH 7.4. After 2 h incubation time the AlphaScreen signal is read on an AlphaQuest-HTS instrument. The $IC_{50}$ values are calculated by using the Prism software.

Other CRTH2 Functional Assay Protocols

The ability of the tested compounds to antagonise the functional effects of PGD2 at the CRTH2 receptor may also be demonstrated by methodology known in the art, such as by a whole cell binding assay, a GTPgS assay, a BRET assay, an inositol phosphate accumulation assay, an CRTH2 cell surface expression assay, a $Ca^{2+}$ influx assay, an ERK phosphorylation assay, an cell migration assay, an eosinophil shape change assay, a Th2 cell degranulation assay, or a basophil activation assay as described by Mathiesen et al., Mol Pharmacol. 2005, 68:393-402; Mimura et al., J Pharmacol Exp Ther, 2005, 314:244-51; Sandham et al., Bioorg Med Chem Lett, 2007, 17:4347-50; Sandham Bioorg Med Chem Lett, 2009, 19:4794-8; Crosignani et al., J Med Chem, 2008, 51:2227-43; Royer et al., Eur J Clin Invest, 2008, 38:663-71; Boehme et al., Int Immunol, 2009, 21:621-32; Sugimoto et al., Pharmacol Exp Ther, 2003, 305:347-52; Monneret et al., J Pharmacol Exp Ther, 2005, 312:627-34; Xue et al., J Immunol, 2005, 175:6531-6.

Cell lines for expressing the CRTH2 receptor include those naturally expressing the CRTH2 receptor, such as AML14.3D10 and NCI-H292 cells (Sawyer et al., Br J Pharmacol, 2002, 137:1163-72; Chiba et al., Int Arch Allergy Immunol, 2007, 143 Suppl 1:23-7), those induced to express the CRTH2 receptor by the addition of chemicals, such as HL-60 or AML14.3D10 cells treated with, for example, butyric acid (Sawyer et al., Br J Pharmacol, 2002, 137:1163-72) or a cell line engineered to express a recombinant CRTH2 receptor, such as L1.2, CHO, HEK-293, K562 or CEM cells (Liu et al., Bioorg Med Chem Lett, 2009, 19:6840-4; Sugimoto et al., Pharmacol Exp Ther, 2003, 305:347-52; Hata et al., Mol Pharmacol, 2005, 67:640-7; Nagata et al., FEBS Lett, 1999, 459:195-9).

Finally, blood or tissue cells, for example human peripheral blood eosinophils, isolated using methods as described by Hansel et al., J Immunol Methods, 1991, 145, 105-110, or human Th2 cells isolated and treated as described by Xue et al., J Immunol, 2005, 175:6531-6, or human basophils isolated and characterized as described by Monneret et al., J Pharmacol Exp Ther, 2005, 312:627-34 can be utilized in such assays.

In particular, the compounds of the present invention have activity in binding to the CRTH2 receptor in the aforementioned assays and inhibit the activation of CRTH2 by CRTH2 ligands. As used herein, "activity" is intended to mean a compound demonstrating an inhibition of 50% at 1 µM or higher in inhibition, or a $K_i$ value <1 µM, when measured in the aforementioned assays. Such a result is indicative of the intrinsic activity of the compounds as inhibitor of CRTH2 receptor activity. Antagonistic activities of selected compounds are shown in table 1 below.

TABLE 1

| Example | CRTH2 Ki (nM) |
|---|---|
| 1.1 | 2.9 |
| 1.2 | 16.3 |
| 1.3 | 30.8 |
| 1.4 | 7.7 |
| 1.5 | 12.9 |
| 1.6 | 3.5 |
| 1.7 | 2.5 |
| 1.8 | 2.6 |
| 1.9 | 28.3 |
| 1.10 | 7.4 |
| 1.11 | 2.7 |
| 1.12 | 12.9 |
| 1.13 | 4.0 |
| 1.14 | 1.1 |
| 1.15 | 0.2 |
| 1.16 | 3.9 |
| 1.17 | 2.5 |
| 1.18 | 17.9 |
| 1.19 | 16.2 |
| 1.20 | 29.3 |
| 1.21 | 80.2 |
| 1.22 | 3319 |
| 1.23 | 5.7 |
| 1.24 | 553 |
| 1.25 | 3.1 |
| 1.26 | 36.0 |
| 1.27 | 9.3 |
| 1.28 | 12.4 |
| 1.29 | 2.5 |
| 1.30 | 14.6 |
| 1.31 | 18.9 |
| 1.32 | 32.5 |
| 1.33 | 29.8 |
| 1.34 | 4.0 |
| 1.35 | 44.6 |
| 2.1 | 0.2 |
| 2.2 | 1.1 |
| 2.3 | 3.4 |
| 2.4 | 1.3 |
| 2.5 | 0.75 |
| 2.6 | 0.25 |
| 2.7 | 12.9 |
| 2.8 | 1.3 |
| 2.9 | 1.8 |
| 2.10 | 0.8 |
| 2.11 | 1.2 |
| 2.12 | 2.3 |
| 2.13 | 2.9 |
| 2.14 | 0.2 |
| 2.15 | 1.4 |
| 2.16 | 23.9 |
| 2.17 | 0.7 |
| 2.18 | 2.8 |
| 2.19 | 5.8 |
| 2.20 | 13.9 |
| 2.21 | 0.5 |
| 2.22 | 1.9 |
| 2.23 | 6.1 |
| 2.24 | 2.8 |
| 2.25 | 46.6 |
| 2.26 | 3.6 |
| 2.27 | 4.3 |
| 2.28 | 17.1 |
| 2.29 | 6.3 |
| 2.30 | 5.8 |
| 2.31 | 5.0 |
| 2.32 | 2.6 |
| 2.33 | 0.8 |
| 2.34 | 4.3 |
| 2.35 | 11.6 |
| 2.36 | 0.7 |
| 2.37 | 0.4 |
| 2.38 | 1.0 |
| 2.39 | 1.6 |

TABLE 1-continued

| Example | CRTH2 Ki (nM) |
|---|---|
| 2.40 | 0.2 |
| 2.41 | 0.2 |
| 2.42 | 0.1 |
| 2.43 | 17.4 |
| 2.44 | 10.2 |
| 2.45 | 8.9 |
| 2.46 | 0.6 |
| 2.47 | 0.1 |
| 2.48 | 1.8 |
| 2.49 | 0.6 |
| 2.50 | 0.1 |
| 2.51 | 3.5 |
| 2.52 | 0.5 |
| 2.53 | 0.2 |
| 2.54 | 0.1 |
| 2.55 | 21.6 |
| 2.56 | 27.8 |
| 2.57 | 19.3 |
| 2.58 | 24.6 |
| 2.59 | 17.4 |
| 2.60 | 4.2 |
| 3.1 | 3.8 |
| 3.2 | 785.7 |
| 3.3 | 0.3 |
| 3.4 | 0.5 |
| 3.5 | 16.8 |
| 3.6 | 14.9 |
| 3.7 | 0.6 |
| 3.8 | 28.6 |
| 3.9 | 0.1 |
| 3.10 | 5.2 |
| 3.11 | 3.5 |
| 3.12 | 0.1 |
| 3.13 | 4.7 |
| 3.14 | 8.9 |
| 4.1 | 16.8 |
| 5.1 | 43.9 |
| 5.2 | 33.7 |
| 5.3 | 30.6 |
| 5.4 | 230.2 |
| 6.1 | 437.8 |
| 6.2 | 311.4 |
| 6.3 | 261.1 |
| 7.1 | 406.6 |
| 7.2 | 161.6 |
| 7.3 | 13.5 |
| 7.4 | 2.2 |
| 7.5 | 0.3 |
| 7.6 | 1.2 |
| 7.7 | 3.4 |
| 7.8 | 0.8 |
| 7.9 | 2.5 |
| 7.10 | 5.5 |
| 7.11 | 0.9 |
| 7.12 | 4.7 |
| 7.13 | 1.3 |
| 7.14 | 1.6 |
| 7.15 | 0.6 |
| 7.16 | 3.5 |
| 7.17 | 1.1 |
| 7.18 | 2.4 |
| 7.19 | 5.8 |
| 7.20 | 2.2 |
| 7.21 | 1.9 |
| 8.1 | 1664.4 |
| 8.2 | 124.7 |
| 8.3 | 3760.8 |
| 8.4 | 26.1 |
| 8.5 | 427.1 |
| 8.6 | 125.5 |
| 8.7 | 668.6 |
| 9.1 | 1480.3 |
| 9.2 | 24.5 |
| 9.3 | 8.7 |
| 9.4 | 18.6 |
| 9.5 | 13.7 |
| 9.6 | 3 |
| 9.7 | 7.5 |

TABLE 1-continued

| Example | CRTH2 Ki (nM) |
|---|---|
| 9.8 | 31 |
| 9.9 | 19.4 |
| 9.11 | 7.1 |
| 9.10 | 39.1 |
| 9.12 | 4.8 |
| 9.13 | 0.9 |
| 9.14 | 3.1 |
| 9.15 | 32 |
| 9.16 | 6.7 |
| 9.17 | 34.9 |
| 9.18 | 24.9 |
| 9.19 | 30.5 |
| 9.20 | 38.0 |
| 9.21 | 7.8 |
| 9.22 | 15.6 |
| 9.23 | 4.0 |
| 9.24 | 49.1 |
| 9.25 | 32.1 |
| 9.26 | 39.4 |
| 9.27 | 0.5 |
| 9.28 | 10.4 |
| 10.1 | 2.6 |
| 10.2 | 742 |
| 10.3 | 16.1 |
| 10.4 | 21.6 |
| 10.5 | 27.8 |
| 11.1 | 29.4 |
| 12.1 | 127.0 |
| 12.2 | 56.3 |
| 12.3 | 12.3 |
| 13.1 | 30 |
| 13.2 | 1070 |
| 13.3 | 619 |
| 13.4 | 325 |
| 13.5 | 36.0 |
| 13.6 | 28.9 |
| 13.7 | 4.8 |
| 13.8 | 15.5 |
| 13.9 | 39.1 |
| 13.10 | 19.6 |
| 13.11 | 48.8 |
| 13.12 | 5.0 |
| 13.13 | 49.9 |
| 14.1 | 1532 |
| 14.2 | 43 |
| 14.3 | 742 |
| 14.4 | 29 |
| 14.5 | 253 |
| 14.6 | 428 |
| 15.1 | 785 |
| 15.2 | 552 |
| 16.1 | 992 |
| 16.2 | 324 |
| 16.3 | 2288 |
| 16.4 | 875 |
| 16.5 | 325 |
| 16.6 | 853 |
| 17.1 | 0.1 |
| 17.2 | 4.3 |
| 18.1 | 1.6 |
| 19.1 | 43.5 |
| 19.2 | 12.0 |
| 19.3 | 12.2 |
| 19.4 | 48.8 |

The invention claimed is:

1. A compound of formula (I)

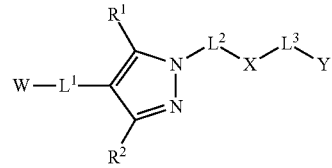

or a pharmaceutically acceptable salt thereof, wherein:

W is selected from hydroxycarbonyl, —C(O)—NH—S(O)$_2$—R$^a$, tetrazol-5-yl, 1,2,4-oxadiazol-5(4H)-on-3-yl, and 1,3,4-oxadiazol-2(3H)-on-5-yl, wherein R$^a$ is selected from $C_1$-$C_6$-alkyl, $C_1$-$C_6$-haloalkyl, cyclopropyl, phenyl, and tolyl;

L$^1$ is methylene, ethylene, ethenylene, or acetylene, wherein each carbon atom in the L$^1$ methylene or ethylene is unsubstituted or carries 1 or 2 radicals selected independently from hydroxy, halogen, $C_1$-$C_6$-alkyl, $C_1$-$C_6$-haloalkyl, $C_1$-$C_6$-alkoxy, $C_1$-$C_6$-haloalkoxy, and $C_3$-$C_8$-cycloalkyl, and wherein two radicals bound to the same carbon atom of the L$^1$ methylene or ethylene together with the carbon atom optionally forms a 3- to 8-membered ring, wherein the ring optionally contains 1 or 2 heteroatoms selected from O, N, and S as ring member and wherein the ring members of the ring are optionally independently substituted by hydroxy, halogen, $C_1$-$C_6$-alkyl, $C_1$-$C_6$-haloalkyl, $C_1$-$C_6$-alkoxy, $C_1$-$C_6$-haloalkoxy, and $C_3$-$C_8$-cycloalkyl, and/or wherein two radicals bound to the same carbon atom of the L$^1$ methylene or ethylene together with the carbon atom optionally forms a carbonyl group;

L$^2$ is methylene or ethylene, wherein each carbon atom in L$^2$ methylene or ethylene is unsubstituted or carries 1 or 2 radicals selected independently from hydroxy, halogen, $C_1$-$C_6$-alkyl, $C_1$-$C_6$-haloalkyl, and $C_3$-$C_8$-cycloalkyl and wherein two radicals bound to the same carbon atom of the L$^2$ methylene or ethylene together with the carbon atom optionally forms a carbonyl group and wherein two radicals bound to the same carbon atom of the L$^2$ methylene or ethylene together with the carbon atom optionally forms a 3- to 8-membered ring, wherein the ring optionally contains 1 or 2 heteroatoms selected from O, N, and S as ring member and wherein the ring members of the ring are optionally independently substituted by hydroxy, halogen, $C_1$-$C_6$-alkyl, $C_1$-$C_6$-haloalkyl, $C_1$-$C_6$-alkoxy, $C_1$-$C_6$-haloalkoxy, or $C_3$-$C_8$-cycloalkyl;

X is a 6-membered carbocyclic or heterocyclic moiety selected from phen-1,4-ylene, pyridin-2,5-ylene, pyridazin-3,6-ylene, pyrimidin-2,5-ylene, and pyrazin-2,5-ylene, each optionally unsubstituted or substituted with 1, 2, or 3 radicals selected independently from hydroxy, halogen, $C_1$-$C_6$-alkyl, $C_1$-$C_6$-haloalkyl, $C_1$-$C_6$-alkoxy, $C_1$-$C_6$-haloalkoxy, and $C_3$-$C_8$-cycloalkyl;

L$^3$ is selected from —CH=CH—, —C≡C—, —CR$^b$R$^c$—CH(OH)—, —CR$^b$R$^c$—C(O)—, —CR$^b$R$^c$—O—, —CR$^b$R$^c$—NR$^d$—, —CR$^b$R$^c$—S(O)$_m$—, —CH(OH)—, —C(O)—, —C(O)—NR$^d$—, —O—, —NR$^d$—, —NR$^d$—C(O)—, —NR$^d$C(O)—O—, —NR$^d$—C(O)—NR$^e$—, —NR$^d$—S(O)$_p$—, —S(O)$_p$—, and —S(O)$_q$—NR$^d$—, wherein m, n, and p are each independently 0, 1, or 2 and q is 1 or 2, and wherein R$^b$ and R$^c$ are independently selected from H, $C_1$-$C_6$-alkyl, and $C_3$-$C_8$-cycloalkyl and wherein two radicals $R^b$ and $R^c$ bound to the same carbon atom together with the carbon atom optionally form a 3- to 8-membered ring, wherein the ring optionally contains 1 or 2 heteroatoms selected from O, N, and S as ring member and wherein the ring members of the ring are optionally independently substituted by hydroxy, halogen, $C_1$-$C_6$-alkyl, $C_1$-$C_6$-haloalkyl, $C_1$-$C_6$-alkoxy, $C_1$-$C_6$-haloalkoxy, and $C_3$-$C_8$-cycloalkyl, and wherein $R^d$ and $R^e$ are each independently H or $C_1$-$C_6$-alkyl;

Y is selected from $C_3$-$C_8$-cycloalkyl, $C_3$-$C_8$-cycloalkyl-$C_1$-$C_6$-alkyl, $C_3$-$C_8$-cycloalkyl-$C_2$-$C_6$-alkenyl, phenyl, phenyl-$C_1$-$C_6$-alkyl, phenyl-$C_2$-$C_6$-alkenyl, naphthyl, naphthyl-$C_1$-$C_6$-alkyl, naphthyl-$C_2$-$C_6$-alkenyl, heterocyclyl, heterocyclyl-$C_1$-$C_6$-alkyl, and heterocyclyl-$C_2$-$C_6$-alkenyl, wherein the $C_1$-$C_6$-alkyl and $C_2$-$C_6$-alkenyl moieties thereof are unsubstituted or carry at least one substituent selected from hydroxy, halogen, cyano, nitro, $C_1$-$C_6$-alkoxy, $C_1$-$C_6$-haloalkoxy, $C_1$-$C_6$-alkylamino, di-$C_1$-$C_6$-alkylamino, and $C_1$-$C_6$-alkylsulfonyl and wherein two of the substituents bound to the same carbon atom of the $C_1$-$C_6$-alkyl moieties together with the carbon atom optionally forms a 3- to 8-membered ring, wherein the ring optionally contains 1 or 2 heteroatoms selected from O, N, and S as ring member, and wherein the $C_3$-$C_8$-cycloalkyl, phenyl, naphthyl, or heterocyclyl moieties thereof are unsubstituted or carry at least one substituent selected from hydroxy, halogen, cyano, nitro, $SF_5$, —C(O)$NR^fR^g$, $C_1$-$C_6$-alkyl, hydroxy-$C_1$-$C_6$-alkyl, $C_1$-$C_6$-alkoxy-$C_1$-$C_6$-alkyl, $C_3$-$C_8$-cycloalkyl, $C_1$-$C_6$-haloalkyl, $C_1$-$C_6$-alkoxy, $C_1$-$C_6$-alkoxy-$C_1$-$C_6$-alkoxy, $C_1$-$C_6$-haloalkoxy, $C_3$-$C_8$-cycloalkoxy, $C_1$-$C_6$-alkylamino, di-$C_1$-$C_6$-alkylamino, $C_1$-$C_6$-alkylsulfonyl, phenyl, phenoxy, 5- or 6-membered heterocyclyl, and 5- or 6-membered heterocyclyloxy, wherein $R^f$ and $R^g$ are independently selected from H, $C_1$-$C_6$-alkyl, $C_1$-$C_6$-haloalkyl, $C_3$-$C_8$-cycloalkyl, $C_3$-$C_8$-cycloalkenyl and 5- or 6-membered heterocyclyl or $R^f$ and $R^g$ together with the nitrogen atom to which they are bound form a cyclic amine, which optionally comprises a further heteroatom selected from O, N, and S as a ring member, and/or wherein two radicals bound to the same carbon atom of the $C_3$-$C_8$-cycloalkyl or heterocyclyl moieties thereof together with the carbon atom optionally forms a carbonyl group, and/or wherein the $C_3$-$C_8$-cycloalkyl, phenyl, naphthyl, or heterocyclyl moieties thereof optionally carry a fused carbocyclic or heterocyclic moiety, wherein the fused carbocyclic or heterocyclic moiety is unsubstituted or carries at least one substituent selected from hydroxy, halogen, cyano, nitro, $C_1$-$C_6$-alkyl, $C_3$-$C_8$-cycloalkyl, $C_1$-$C_6$-haloalkyl, $C_1$-$C_6$-alkoxy, $C_1$-$C_6$-haloalkoxy, $C_1$-$C_6$-alkylamino, di-$C_1$-$C_6$-alkylamino, $C_1$-$C_6$-alkylsulfonyl, phenyl, and 5- or 6-membered hetaryl, and/or wherein two radicals bound to the same carbon atom of the fused carbocyclic or heterocyclic moiety together with the carbon atom optionally forms a carbonyl group; and $R^1$ and $R^2$ are each independently selected from H, halogen, $C_1$-$C_6$-alkyl, $C_2$-$C_6$-alkenyl, $C_2$-$C_6$-alkynyl, $C_1$-$C_6$-alkoxy, $C_1$-$C_6$-alkylthio, —$NR^fR^g$, $C_3$-$C_8$-cycloalkyl, $C_3$-$C_8$-cycloalkyl-$C_1$-$C_6$-alkyl, $C_3$-$C_8$-cycloalkyl-$C_2$-$C_6$-alkenyl, $C_3$-$C_8$-cycloalkenyl, $C_3$-$C_8$-cycloalkenyl-$C_1$-$C_6$-alkyl, $C_3$-$C_8$-cycloalkenyl-$C_2$-$C_6$-alkenyl, phenyl, phenyl-$C_1$-$C_6$-alkyl, phenyl-$C_2$-$C_6$-alkenyl, naphthyl, naphthyl-$C_1$-$C_6$-alkyl, naphthyl-$C_2$-$C_6$-alkenyl, heterocyclyl, heterocyclyl-$C_1$-$C_6$-alkyl, and heterocyclyl-$C_2$-$C_6$-alkenyl, wherein the $C_1$-$C_6$-alkyl, $C_2$-$C_6$-alkenyl and $C_2$-$C_6$-alkynyl moieties in $R^1$ and $R^2$ are unsubstituted or carry at least one substituent selected from hydroxy, halogen, cyano, nitro, $C_1$-$C_6$-alkoxy, $C_1$-$C_6$-haloalkoxy, $C_1$-$C_6$-alkylamino, di-$C_1$-$C_6$-alkylamino, and $C_1$-$C_6$-alkylsulfonyl, and/or wherein two radicals bound to the same carbon atom of the $C_1$-$C_6$-alkyl, $C_2$-$C_6$-alkenyl, and $C_2$-$C_6$-alkynyl moieties in $R^1$ and $R^2$ together with the carbon atom optionally forms a carbonyl group, and the $C_3$-$C_8$-cycloalkyl, cycloalkenyl, phenyl, naphthyl, and heterocyclyl moieties in $R^1$ and $R^2$ are unsubstituted or carry at least one substituent selected from hydroxy, halogen, cyano, nitro, $C_1$-$C_6$-alkyl, $C_3$-$C_8$-cycloalkyl, $C_1$-$C_6$-haloalkyl, $C_1$-$C_6$-alkoxy, $C_1$-$C_6$-haloalkoxy, $C_1$-$C_6$-alkylamino, di-$C_1$-$C_6$-alkylamino, $C_1$-$C_6$-alkylsulfonyl, phenyl, and 5- or 6-membered hetaryl, and/or wherein two radicals bound to the same carbon atom of the $C_3$-$C_8$-cycloalkyl, $C_3$-$C_8$-cycloalkenyl, and heterocyclyl moieties of $R^1$ and $R^2$ together with the carbon atom optionally forms a carbonyl group, and $R^f$ and $R^g$ are independently selected from H, $C_1$-$C_6$-alkyl, $C_1$-$C_6$-haloalkyl, $C_3$-$C_8$-cycloalkyl, $C_3$-$C_8$-cycloalkenyl, and heterocyclyl, or $R^f$ and $R^g$ together with the nitrogen atom to which they are bound form a cyclic amine, which optionally comprises a further heteroatom selected from O, N, and S as a ring member.

2. The compound of formula (I) according to claim 1, or a pharmaceutically acceptable salt thereof, wherein W is hydroxycarbonyl.

3. The compound of formula (I) according to claim 1, or a pharmaceutically acceptable salt thereof, wherein $L^1$ is methylene.

4. The compound of formula (I) according to claim 3, or a pharmaceutically acceptable salt thereof, wherein $L^1$ is unsubstituted methylene.

5. The compound of formula (I) according to claim 1, or a pharmaceutically acceptable salt thereof, wherein $L^2$ is methylene.

6. The compound of formula (I) according to claim 5, or a pharmaceutically acceptable salt thereof, wherein $L^2$ is unsubstituted methylene.

7. The compound of formula (I) according to claim 1, or a pharmaceutically acceptable salt thereof, wherein X is phen-1,4-ylene or pyridin-2,5-ylene.

8. The compound of formula (I) according to claim 7, or a pharmaceutically acceptable salt thereof, wherein X is phen-1,4-ylene.

9. The compound of formula (I) according to claim 8, or a pharmaceutically acceptable salt thereof, wherein X is unsubstituted phen-1,4-ylene.

10. The compound of formula (I) according to claim 1, or a pharmaceutically acceptable salt thereof, wherein $L^3$ is selected from —CH═CH—, —C≡C—, —$CR^bR^c$—O—, —$CR^bR^c$—S(O)$_m$—, —CH(OH)—, —C(O)—, —C(O)—$NR^d$—, —O—, —$NR^d$—, —$NR^d$—C(O)—, —$NR^d$C(O)O—, —$NR^d$—C(O)—$NR^e$—, —$NR^d$—S(O)$_p$—, —S(O)$_p$—, and —S(O)$_q$—$NR^d$—.

11. The compound of formula (I) according to claim 10, or a pharmaceutically acceptable salt thereof, wherein $L^3$ is selected from —$CR^bR^c$—O—, —C(O)—$NR^d$—, —O—, —$NR^d$—C(O)—, —$NR^d$C(O)O—, —$NR^d$C(O)—$NR^e$—, —$NR^d$—S(O)$_p$—, and —S(O)$_q$—$NR^d$—.

12. The compound of formula (I) according to claim 11, or a pharmaceutically acceptable salt thereof, wherein $L^3$ is —C(O)—NR$^d$— and R$^d$ is H or $C_1$-$C_6$-alkyl.

13. The compound of formula (I) according to claim 11, or a pharmaceutically acceptable salt thereof, wherein $L^3$ is —NR$^d$—C(O)— and R$^d$ is H or $C_1$-$C_6$-alkyl.

14. The compound of formula (I) according to claim 11, or a pharmaceutically acceptable salt thereof, wherein $L^3$ is —NR$^d$C(O)O- and R$^d$ is H or $C_1$-$C_6$-alkyl.

15. The compound of formula (I) according to claim 11, or a pharmaceutically acceptable salt thereof, wherein $L^3$ is —S(O)$_2$—NR$^d$—.

16. The compound of formula (I) according to claim 1, or a pharmaceutically acceptable salt thereof, wherein Y is selected from phenyl, phenyl-$C_1$-$C_6$-alkyl, phenyl-$C_2$-$C_6$-alkenyl, naphthyl, naphthyl-$C_1$-$C_6$-alkyl, and naphthyl-$C_2$-$C_6$-alkenyl, wherein the phenyl or naphthyl moieties thereof are unsubstituted or carry at least one substituent selected from hydroxy, halogen, cyano, nitro, SF$_5$, —C(O)NR$^f$R$^g$, $C_1$-$C_6$-alkyl, hydroxy-$C_1$-$C_6$-alkyl, $C_1$-$C_6$-alkoxy-$C_1$-$C_6$-alkyl, $C_3$-$C_8$-cycloalkyl, $C_1$-$C_6$-haloalkyl, $C_1$-$C_6$-alkoxy, $C_1$-$C_6$-alkoxy-$C_1$-$C_6$-alkoxy, $C_1$-$C_6$-haloalkoxy, $C_3$-$C_8$-cycloalkoxy, $C_1$-$C_6$-alkylamino, di-$C_1$-$C_6$-alkylamino, $C_1$-$C_6$-alkylsulfonyl, phenyl, phenoxy, 5- or 6-membered heterocyclyl, and 5- or 6-membered heterocyclyloxy, and/or
wherein the phenyl or naphthyl moieties thereof optionally carry a fused carbocyclic or heterocyclic moiety, wherein the fused carbocyclic or heterocyclic moiety is unsubstituted or carries at least one substituent selected from hydroxy, halogen, cyano, nitro, $C_1$-$C_6$-alkyl, $C_3$-$C_8$-cycloalkyl, $C_1$-$C_6$-haloalkyl, $C_1$-$C_6$-alkoxy, $C_1$-$C_6$-haloalkoxy, $C_1$-$C_6$-alkylamino, di-$C_1$-$C_6$-alkylamino, $C_1$-$C_6$-alkylsulfonyl, phenyl, and 5- or 6-membered hetaryl, and/or
wherein two radicals bound to the same carbon atom of the fused carbocyclic or heterocyclic moiety together with the carbon atom optionally forms a carbonyl group.

17. The compound of formula (I) according to claim 16, or a pharmaceutically acceptable salt thereof, wherein Y is selected from phenyl, benzyl, phenethyl, phenethenyl, naphthyl, naphthylmethyl, naphthylethyl, and naphthylethenyl.

18. The compound of formula (I) according to claim 16, or a pharmaceutically acceptable salt thereof, wherein Y is selected from phenyl and naphthyl.

19. The compound of formula (I) according to claim 1, or a pharmaceutically acceptable salt thereof, wherein R$^1$ and R$^2$ are each independently selected from $C_1$-$C_6$-alkyl, $C_3$-$C_8$-cycloalkyl, phenyl, and naphthyl.

20. The compound of formula (I) according to claim 19, or a pharmaceutically acceptable salt thereof, wherein R$^1$ and R$^2$ are each independently selected from $C_1$-$C_4$-alkyl, $C_3$-$C_6$-cycloalkyl, and phenyl.

21. The compound of formula (I) according to claim 1, or a pharmaceutically acceptable salt thereof, wherein at least one of R$^1$ and R$^2$ is $C_1$-$C_4$-alkyl.

22. A method of treating a CRTH2-activity disorder selected from a respiratory or gastrointestinal diseases; an inflammatory diseases of the joints; and an allergic diseases of the nasopharynx, eyes, and skin, the method comprising administering to a patient in need thereof of a pharmaceutically effective amount of the compound of formula (I) according to claim 1, or a pharmaceutically acceptable salt thereof.

23. The method of claim 22, wherein the CRTH2-activity disorder is a respiratory or gastrointestinal disease.

24. A pharmaceutical formulation comprising the compound of formula (I) according to claim 1, or a pharmaceutically acceptable salt thereof.

25. A pharmaceutical formulation comprising the compound of formula (I) according to claim 1, or a pharmaceutically acceptable salt thereof, and one or more active substances selected from among betamimetics, anticholinergics, corticosteroids, PDE4 inhibitors, LTD4 antagonists, EGFR inhibitors, CCR3 antagonists, CCR5 antagonists, CCR9 antagonists, 5-LO inhibitors, histamine-receptor antagonists, SYK inhibitors, and sulfonamides.

26. The compound of formula (I) according to claim 1, wherein the compound is {3,5-dimethyl-1-[4-(4-trifluoromethylbenzoylamino)benzyl]-1H-pyrazol-4-yl}acetic acid or a pharmaceutically acceptable salt thereof.

27. The compound of formula (I) according to claim 1, wherein the compound is {3,5-dimethyl-1-[4-(4-chloro-2-methylbenzoylamino)benzyl]-1H-pyrazol-4-yl}acetic acid or a pharmaceutically acceptable salt thereof.

28. The compound of formula (I) according to claim 1, wherein the compound is {3,5-dimethyl-1-[4-(benzoylamino)benzyl]-1H-pyrazol-4-yl}acetic acid or a pharmaceutically acceptable salt thereof.

29. The compound of formula (I) according to claim 1, wherein the compound is {3,5-dimethyl-1-[4-(4-methylbenzoylamino)benzyl]-1H-pyrazol-4-yl}acetic acid or a pharmaceutically acceptable salt thereof.

30. The compound of formula (I) according to claim 1, wherein the compound is {3,5-dimethyl-1-[4-(4-methoxybenzoylamino)benzyl]-1H-pyrazol-4-yl}acetic acid or a pharmaceutically acceptable salt thereof.

31. The compound of formula (I) according to claim 1, wherein the compound is {3,5-dimethyl-1-[4-(4-chloromethylbenzoylamino)benzyl]-1H-pyrazol-4-yl}acetic acid or a pharmaceutically acceptable salt thereof.

32. The compound of formula (I) according to claim 1, wherein the compound is {3,5-Dimethyl-1-[4-(naphtalene-2-carbonylamino)-benzyl]-1H-pyrazol-4-yl}-acetic acid or a pharmaceutically acceptable salt thereof.

33. The compound of formula (I) according to claim 1, wherein the compound is {3,5-dimethyl-1-[4-(3,4-dichloromethylbenzoylamino)benzyl]-1H-pyrazol-4-yl}acetic acid or a pharmaceutically acceptable salt thereof.

34. The compound of formula (I) according to claim 1, wherein the compound is {3,5-dimethyl-1-[4-(2-methyl-4-trifluoromethylbenzoylamino)benzyl]-1H-pyrazol-4-yl}acetic acid or a pharmaceutically acceptable salt thereof.

35. The compound of formula (I) according to claim 1, wherein the compound is {3,5-dimethyl-1-[4-(2,4-dimethylbenzoylamino)benzyl]-1H-pyrazol-4-yl}acetic acid or a pharmaceutically acceptable salt thereof.

36. The compound of formula (I) according to claim 1, wherein the compound is {3,5-dimethyl-1-[4-(4-tert-butylbenzoylamino)benzyl]-1H-pyrazol-4-yl}acetic acid or a pharmaceutically acceptable salt thereof.

37. The compound of formula (I) according to claim 1, wherein the compound is {3,5-dimethyl-1-[4-(4-bromo-2-methylbenzoylamino)benzyl]-1H-pyrazol-4-yl}acetic acid or a pharmaceutically acceptable salt thereof.

38. The compound of formula (I) according to claim 1, wherein the compound is {3,5-dimethyl-1-[4-(4-bromo-2,5-dimethylbenzoylamino)benzyl]-1H-pyrazol-4-yl}acetic acid or a pharmaceutically acceptable salt thereof.

39. The compound of formula (I) according to claim 1, wherein the compound is {3,5-dimethyl-1-[4-(2,4-dichlorobenzoylamino)benzyl]-1H-pyrazol-4-yl}acetic acid or a pharmaceutically acceptable salt thereof.

40. The compound of formula (I) according to claim 1, wherein the compound is {3,5-dimethyl-1-[4-(4-chloro-2- fluorobenzoylamino)benzyl]-1H-pyrazol-4-yl}acetic acid or a pharmaceutically acceptable salt thereof.

41. The compound of formula (I) according to claim 1, wherein the compound is {3,5-dimethyl-1-[4-(2-fluoro-4-methylbenzoylamino)benzyl]-1H-pyrazol-4-yl}acetic acid or a pharmaceutically acceptable salt thereof.

42. The compound of formula (I) according to claim 1, wherein the compound is {3,5-dimethyl-1-[4-(4-methyl-2-trifluoromethylbenzoylamino)benzyl]-1H-pyrazol-4-yl}acetic acid or a pharmaceutically acceptable salt thereof.

43. The compound of formula (I) according to claim 1, wherein the compound is {3,5-dimethyl-1-[4-(2-fluoro-4-trifluoromethylbenzoylamino)benzyl]-1H-pyrazol-4-yl}acetic acid or a pharmaceutically acceptable salt thereof.

44. The compound of formula (I) according to claim 1, wherein the compound is {3,5-dimethyl-1-[4-(3-chloronaphtalene-2-carbonylamino)benzyl]-1H-pyrazol-4-yl}acetic acid or a pharmaceutically acceptable salt thereof.

45. The compound of formula (I) according to claim 1, wherein the compound is {3,5-dimethyl-1-[4-(2,4,6-trimethylbenzoylamino)benzyl]-1H-pyrazol-4-yl}acetic acid or a pharmaceutically acceptable salt thereof.

46. The compound of formula (I) according to claim 1, wherein the compound is {3,5-dimethyl-1-[4-(3-methyl-naphtalene-2-carbonylamino)benzyl]-1H-pyrazol-4-yl}acetic acid or a pharmaceutically acceptable salt thereof.

47. The compound of formula (I) according to claim 1, wherein the compound is {3,5-dimethyl-1-[4-(1-methyl-naphtalene-2-carbonylamino)benzyl]-1H-pyrazol-4-yl}acetic acid or a pharmaceutically acceptable salt thereof.

48. The compound of formula (I) according to claim 1, wherein the compound is {3,5-dimethyl-1-[4-(4-bromo-2-chlorobenzoylamino)benzyl]-1H-pyrazol-4-yl}acetic acid or a pharmaceutically acceptable salt thereof.

49. The compound of formula (I) according to claim 1, wherein the compound is {3,5-dimethyl-1-[4-(2-bromo-4-chlorobenzoylamino)benzyl]-1H-pyrazol-4-yl}acetic acid or a pharmaceutically acceptable salt thereof.

50. The compound of formula (I) according to claim 1, wherein the compound is {3,5-dimethyl-1-[4-(1-bromonaphtalene-2-carbonylamino)benzyl]-1H-pyrazol-4-yl}acetic acid or a pharmaceutically acceptable salt thereof.

51. The compound of formula (I) according to claim 1, wherein the compound is {3,5-dimethyl-1-[4-(2-bromo-5-methylbenzoylamino)benzyl]-1H-pyrazol-4-yl}acetic acid or a pharmaceutically acceptable salt thereof.

\* \* \* \* \*